US006207832B1

(12) United States Patent
Curran et al.

(10) Patent No.: US 6,207,832 B1
(45) Date of Patent: *Mar. 27, 2001

(54) CAMPTOTHECIN ANALOGS AND METHODS OF PREPARATION THEREOF

(75) Inventors: Dennis P. Curran; Bom David, both of Pittsburgh, PA (US); Thomas G. Burke, Lexington, KY (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/290,019

(22) Filed: Apr. 9, 1999

(51) Int. Cl.[7] ....................... C07D 491/14; C07D 491/22

(52) U.S. Cl. ............................. 546/14; 546/41; 546/48; 514/279; 514/283

(58) Field of Search .................... 514/279, 283; 546/14, 41, 48

(56) References Cited

U.S. PATENT DOCUMENTS

| 5,468,859 | 11/1995 | Fortunak . | |
|---|---|---|---|
| 5,700,939 | 12/1997 | Fortunak . | |
| 5,910,491 | 6/1999 | Hausheer . | |
| 5,935,967 | 8/1999 | Hausheer . | |
| 5,981,542 | * 11/1999 | Bigg et al. ........................ | 514/283 |
| 6,057,303 | 10/1998 | Haridas . | |

FOREIGN PATENT DOCUMENTS

| WO97/00876 | 1/1997 | (WO) . |
|---|---|---|
| WO98/07727 | 2/1998 | (WO) . |
| WO98/28305 | 7/1998 | (WO) . |
| WO98/35940 | 8/1998 | (WO) . |
| WO99/11646 | 3/1999 | (WO) . |
| WO00/50427 | 8/2000 | (WO) . |

OTHER PUBLICATIONS

Curran, D.P. and Liu, H., "New 4+1 Radical Annulations—A Formal Total Synthesis of (+/−)–Camptothecin," J. Am. Chem Soc., 114, 5863–5864 (1992). Published Jul. 1, 1992.
Curran, D.P., "The Camptothecins—A reborn Family of Antitumor Agents", J. Chin. Chem. Soc., 40, 1–6 (1993). Published Feb. 1993.
Curran, D.P. et al., "Recent Applications of Radical Reactions in Natural Product Synthesis," Pure Appl. Chem., 65, 1153–1159 (1993). Published Jun. 1993.
Curran, D.P. et al., "Cascade Radical Reactions of Isonitriles: A Second–Generation Synthesis of (20S)–Camptothecin, Topotecan, Irinotecan, and GI–147211C," Agnew. Chem. Int. Ed, 34, 2683–2684 (1995). Published Jan. 5, 1996.
Curran, D.P., Liu, H.; Josien, H; Ko, S.B., "Tandem Radical Reactions of Isonitriles with 2–pyrdonyl and other aryl radicals: Scope and Limitations, and a First Generation Sunthesis of (+/−)–Camptothecin," Tetrahedron, 52, 11385–11404 (1996). Published Aug. 1996.

Josien, H. et al., "Synthesis of (S)–mappicine and Mappicine Ketone Via Radical Cascade Reaction of Isonitirles," Tetrahedron, 53, 8881–8886 (1997). Published Jun. 30, 1997.
Josien, H. et al., "7–Silylcamptothecins (Silatecans): A New Family of Camptothecin Antitumor Agents," Bioorg. Med. Chem. Lett. 7, 3189–3295 (1997).
Josien, H. et al., "A General Synthetic Approach to the (20S)–Camptothecin Family of Antitumor Agents by a Regiocontrolled Cascade Radical Cyclization of Aryl Isonitriles," Chem. Eur. J. 4, 67–83 (1998). Published Jan. 1998.
Zihou, M. et al., "Reduced Albumin Binding Promotes the Stability and Activity of Topotecan in Human Blood," Biochemistry, 34, 13722–13727 (1995).
Burke, T.G. and Zihou, M., "The Structural Basis of Camptothecin Interaction with Human Serum Albumin: Impact on Drug Stability," J. Med. Chemistry, 37, 40–46 (1994).
Zihou, M. and Burke, T.G., "Marked Interspecies Variations Concerning the Interactions of Camptothecin with Serum Albumins: A Frequency–Domain fluorescence Spectroscopic Study," Biochemistry, 33, 12540–12545 (1994).
Zihou, M. and Burke, T.G., "Differential Interactions of Camptothecin Lactone and Carboxylate Forms with Human Blood Components," Biochemistry, 33, 10325–10336 (1994).

(List continued on next page.)

Primary Examiner—Charanjit S. Aulakh
(74) Attorney, Agent, or Firm—Bartony & Hare

(57) ABSTRACT

A compound has the formula

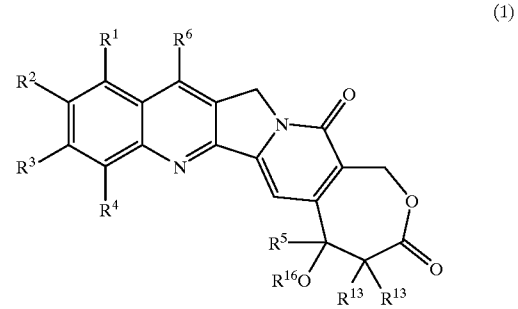

(1)

in racemic form, enantiomerically enriched form or enantiomerically pure form. $R^6$ is preferably $-Si(R^8R^9R^{10})$ or $-(R^7)Si(R^8R^9R^{10})$, wherein $R^7$ is an alkylene group, an alkenylene group, or an alkynylene group; and $R^8$, $R^9$ and $R^{10}$ are independently a $C_{1-10}$ alkyl group, a $C_{2-10}$ alkenyl group, a $C_{2-10}$ alkynyl group, an aryl group or a $-(CH_2)_N R^{11}$ group, wherein N is an integer within the range of 1 through 10 and $R^{11}$ is a hydroxy group, alkoxy group, an amino group, an alkylamino group, a dialkylamino group, a halogen atom, a cyano group, $-SR^c$ or a nitro group. $R^1$-$R$ can be broadly substituted. $R^5$ is preferably a $C_{1-10}$ alkyl group, an alkenyl group, an alkynyl group, or a benzyl group. $R^{13}$ is preferably H, F or $-CH_3$. $R^{16}$ is $R^{16}$ is $-C(O)R^f$ or H. The E-ring (the lactone ring) may be opened. A method of synthesis of compound (1) and intermediates in the synthesis thereof are provided.

9 Claims, 18 Drawing Sheets

OTHER PUBLICATIONS

Burke, T.G., and Zihou, M., "Ethyl Substitution at the 7 Position Extends the Half–Life of 10–Hydroxycamptothecin in the Presence of Human Serum Albumin," J. Med. Chemistry, 37:17, 2580–2582 (1993).

Burke, T.G. et al., "Lipid Bilayer Partitioning and Stability of Camptothecin Drugs," Biochemistry, 32:20, 5352–5364 (1993).

Zihou, M. and Burke, T.G., Preferential Binding of the Carboxylate Form of Camptothecin by Human Serum Albumin, Anal. Biochem., 212, 285–287 (1993).

Burke, T.G. and Tritton, T.R., "Structural Basis of Anthracycline Selectivity for Unilamellar Phosphatidylcholine Vesicles: An Equilibrium Binding Study," Biochemistry, 24, 1768–1776 (1985).

Burke, T.G. and Tritton, T.R., "Location and Dynamics of Anthracycline Bound to Unilamellar Phosphatidylcholine Vesicles," Biochemistry, 24, 5972–5980 (1985).

Burke, T.G. et al., "The Important Role of Albumin in Determining the Relative Human Blood Stabilities of the Camptothecin Anticancer Drugs," J. Parm. Sciences, 84:4 (1995).

* cited by examiner

Synthesis of Precursers for the Radical Cascade Reaction

*Synthesis of New AB-Ring Modified Homosilatecan Derivitives*

|    | R⁶       | R²    | Yield |
|----|----------|-------|-------|
| 1a | SiMe₂ᵗBu | NHBoc | 15%   |
| 1b | SiMe₂ᵗBu | NH₂   | 89%   |
| 1c | SiMe₃    | NHBoc | 53%   |
| 1d | SiMe₃    | NH₂   | 45%   |
| 1e | SiMe₂ᵗBu | OAc   | 20%   |
| 1f | SiMe₂ᵗBu | OH    | 79%   |
| 1g | SiMe₂ᵗBu | H     | 27%   |
| 1h | SiMe₃    | H     | 37%   |

CAMPTOTHECIN ANALOGS AND METHODS OF PREPARATION THEREOF

GOVERNMENT INTERESTS

This invention was made with government support under grant no. RO1 GM031678 awarded by the National Institutes of Health. The government has certain rights in this invention.

RELATED APPLICATIONS

Field of the Invention

The present invention relates to novel compounds and methods of preparation thereof and, particularly, to E-ring expanded camptothecin derivatives or analogs and to methods of preparation of such camptothecin analogs.

BACKGROUND OF THE INVENTION

Camptothecins are DNA topoisomerase I inhibitors now being used as anticancer drugs. Topotecan (tpt) and CPT-11 are the first two members in the camptothecin family to gain Food and Drug Administration full approval status (topotecan in 1996 as second-line therapy for advanced epithelial ovarian cancer, topotecan again in 1998 for the treatment of small cell lung cancer, CPT-11 in 1998 as first-line therapy for colon cancer). Several other analogs of the camptothecin family such as GI-147211C, DX8951f, 9-aminocamptothecin (9-AC) and 9-nitrocamptothecin are in various stages of pre-clinical and clinical evaluation. Each of the campothecins in clinical use undergoes relatively rapid hydrolysis in the bloodsteam resulting in a marked loss of anticancer activity. It is the key α-hydroxylactone pharmacophore within clinically relevant camptothecins that hydrolyzes at physiological pH to yield a biologically-inactive and potentially toxic hydroxy carboxylate form. Fassberg, J. and Stella, V. J., "A Kinetic and Mechanistic Study of the Hydrolysis of Camptothecin and Some Analogues", *J. Pharm. Sci.* 81: 676–684 (1992); Hertzberg, R. P., Caranfa, M. J., and Hecht, S. M., "On the Mechanism of Topoisomerase I Inhibition by Camptothecin: Evidence for Binding to an Enzyme-DNA Complex", *Biochemistry* 28: 4629–4638 (1989); Hsiang, Y-H., and Liu, L. F., "Identification of Mammalian DNA Topoisomerase I as an Intracellular Target of the Anticancer Drug Camptothecin", *Cancer Res.* 48: 1722–1726 (1988); and Jaxel, C., Kohn, K. W., Wani, M. C., Wall, M. E., and Pommier, Y., "Structure-Activity Study of Camptothecin Derivatives on Mammalian Topoisomerase I: Evidence for a Specific Receptor Site and a Relation to Antitumor Activity", *Cancer Res.* 49: 5077–5082 (1989). References set forth herein, including those set forth above, may facilitate understanding of the present invention. Inclusion of a reference herein is not intended to an does no constitute an admission that the reference is prior art with respect to the present invention.

The structures of camptothecin and some of its important analogs are shown below:

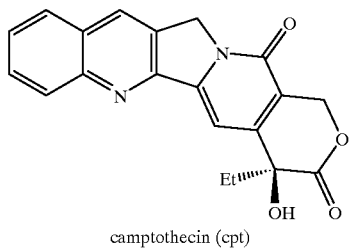

camptothecin (cpt)

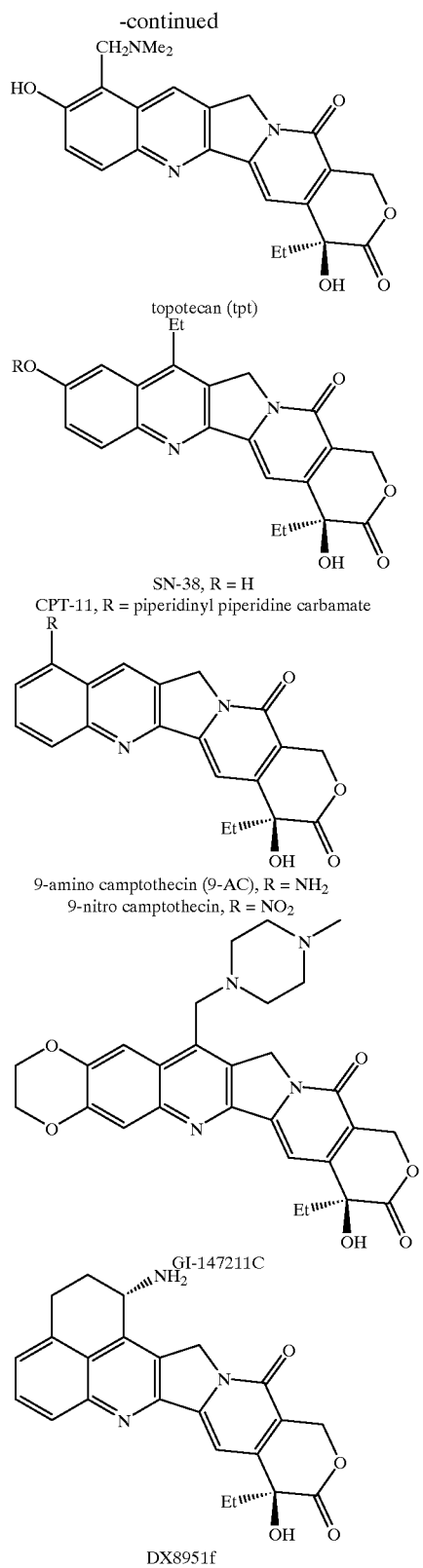

Recent research efforts have shown that agents such as 9-aminocamptothecin and camptothecin (cpt) display very poor stabilities in human blood due to high affinity binding interactions between their carboxylate forms and human serum albumin (HSA). Burke, T. G, Mi, Z., Jiang, Y., and Munshi, C. B. "The Important Role of Albumin in Determining the Relative Human Blood Stabilities of the Camptothecin Anticancer Drugs", *Journal of Pharmaceutical Sciences*, 84: 518–519 (1995); Burke, T. G. and Mi, Z. "The Structural Basis of Camptothecin Interactions with Human Serum Albumin: Impact on Drug Stability", *Journal of Medicinal Chemistry*, 37: 40–46 (1994); Mi, Z. and Burke, T. G., "Differential interactions of Camptothecin Lactone and Carboxylate Forms with Human Blood Components", *Biochemistry*, 33: 10325–10336 (1994); and Mi, Z., Malak, H., and Burke, T. G. "Reduced Albumin Binding Promotes the Stability and Activity of Topotecan in Human Blood", *Biochemistry*, 34: 13722–13728 (1995), the disclosures of which are incorporated herein by reference. Frequency-domain lifetime fluorometry experiments revealed that human serum albumin (HSA) preferentially binds camptothecin carboxylate with over a 100-fold higher affinity compared to camptothecin lactone. Mi, Z. and Burke, T. G. "Marked Interspecies Variations Concerning the Interactions of Camptothecin with Serum Albumins: A Frequency-Domain Fluorescence Spectroscopic Study", *Biochemistry*, 33: 12540–12545 (1994), the disclosure of which is incorporated herein by reference. This differential binding of carboxylate over lactone results in camptothecin and 9-AC opening more rapidly and completely in the presence of HSA than in the absence of the protein. In human plasma, pH 7.4 and 37° C., camptothecin and 9-AC both open rapidly and essentially completely to almost negligible 0.2% lactone levels at equilibrium. While the presence of HSA promotes lactone ring opening for camptothecin and 9-AC, red blood cells and lipid bilayers in general preferentially bind the electroneutral lactone forms of camptothecins over their respective negatively-charged carboxylate lactone forms. Burke, T. G., Staubus, A. E., Mishra, A. K., and Malak, H., "Liposomal Stabilization of Camptothecin's Lactone Ring", *J. Am. Chem. Soc.* 114: 8318–8319 (1992); and Burke, T. G., Mishra, A. K., Wani, M., and Wall, M., "Lipid Bilayer Partitioning and Stability of Camptothecin Drugs", *Biochemistry*, 32: 5352–5364 (1993), the disclosures of which are incorporated herein by reference. Drug interactions with erythrocytes thereby promote active lactone levels in blood.

Activity of Novel E-Ring Modified Camptothecin Analogs", *J. Med. Chem.*, 41, 5410–5419 (1998); and Lavergne, O., Lesueur-Ginot, L., Rodas, F. P., and Bigg, D., "An E-Ring Modified Camptothecin With Potent Antiproliferative and Topoisomerase I inhibitory Activities. Bioorg. Med. Chem. Lett. 7, 2235–2238 (1997). The modification to the E-ring in the studies of Lavergne et al. involved insertion of a methylene spacer between the 20-OH functionality and the carboxyl group of the naturally occurring six-membered α-hydroxylactone of camptothecin. Incorporation of the new 7-membered β-hydroxylactone ring into camptothecin was found to improve the solution and plasma stability of the agent.

The structure of the homocamptothecin of Lavergne et al. and the numbering system used to describe such compounds are shown below:

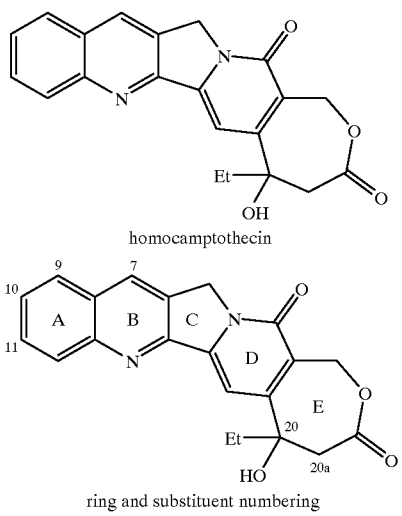

Although substantial strides have been made in the development of the camptothecin family of drugs, it remains very desirable to develop improved compounds in this family of drugs and to develop improved synthetic routes for producing such drugs.

Lactone/Carboxylate Equilibrium

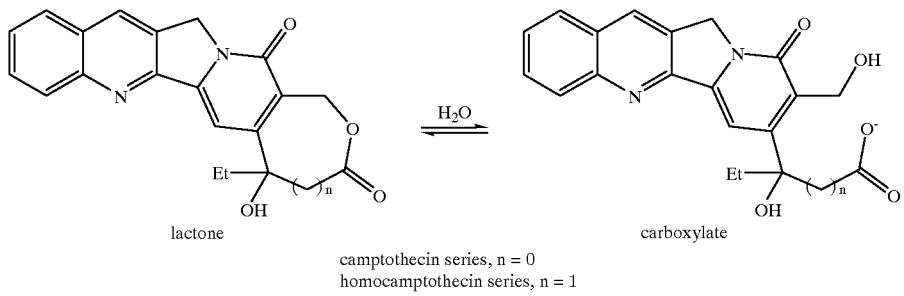

camptothecin series, n = 0
homocamptothecin series, n = 1

Recently, Lavergne et al. have shown that expansion of the E-ring of camptothecin to produce a "homocamptothecin" enhances the solution stability of camptothecin while maintaining anticancer activity. Lavergne, O., Lesueur-Ginot, L., Rodas, F. P., Kasprzyk, P. G., Pommier, J., Demarquay, D., Prevost, G., Ulibarri, G., Rolland, A., Schiano-Liberatore, A.-M., Harnett, J., Pons, D., Camara, J., Bigg, D., "Homocamptothecins: Synthesis and Antitumor

SUMMARY OF THE INVENTION

The present invention provides generally for a compound having the following formula (1):

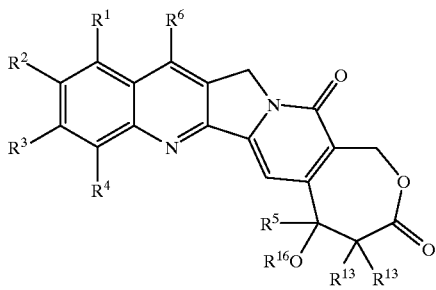

(1)

in racemic form, enantiomerically enriched form or enantiomerically pure form;

wherein $R^1$ and $R^2$ are independently the same or different and are hydrogen, —C(O)$R^f$ wherein $R^f$ is an alkyl group, an alkoxy group, an amino group or a hydroxy group, an alkyl group, an alkenyl group, an alkynyl group, an alkoxy group, an aryloxy group, an acyloxy group, —OC(O)O$R^d$, wherein $R^d$ is an alkyl group, —OC(O)N$R^a R^b$ wherein $R^a$ and $R^b$ are independently the same or different, H, —C(O)$R^f$, an alkyl group or an aryl group, a halogen, a hydroxy group, a nitro group, a cyano group, an azido group, a formyl group, a hydrazino group, an amino group, —S$R^c$, wherein $R^c$ is hydrogen, —C(O)$R^f$, an alkyl group or an aryl group; or $R^1$ and $R^2$ together form a chain of three or four members selected from the group of CH, CH$_2$, O, S, NH, or N$R^{15}$, wherein $R^{15}$ is an $C_1$–$C_6$ alkyl group;

$R^3$ is H, a halogen atom, a nitro group, an amino group, a hydroxy group, or a cyano group; or $R^2$ and $R^3$ together form a chain of three or four members selected from the group of CH, CH$_2$, O, S, NH, or N$R^{15}$, wherein $R^{15}$ is an $C_1$–$C_6$ alkyl group;

$R^4$ is H, F, an amino group, a $C_{1-3}$ alkyl group, a $C_{2-3}$ alkenyl group, a $C_{2-3}$ alkynyl group, a trialkylsilyl group or a $C_{1-3}$ alkoxy group;

$R^5$ is a $C_{1-10}$ alkyl group, an alkenyl group, an alkynyl group, or a benzyl group;

$R^6$ is —Si($R^8 R^9 R^{10}$) or —($R^7$)Si($R^8 R^9 R^{10}$), wherein $R^7$ is an alkylene group, an alkenylene group, or an alkynylene group;

and $R^8$, $R^9$ and $R^{10}$ are independently a $C_{1-10}$ alkyl group, a $C_{2-10}$ alkenyl group, a $C_{2-10}$ alkynyl group, an aryl group or a —(CH$_2$)$_N R^{11}$ group, wherein N is an integer within the range of 1 through 10 and $R^{11}$ is a hydroxy group, an alkoxy group, an amino group, an alkylamino group, a dialkylamino group, a halogen atom, a cyano group, —S$R^c$ or a nitro group;

$R^{13}$ is H, F or —CH$_3$;

$R^{16}$ is —C(O)$R^f$ or H; and pharmaceutically acceptable salts thereof.

$R^1$ and $R^2$ together may, for example, form a group of the formula —O(CH$_2$)$_n$O— wherein n represents the integer 1 or 2. Likewise, $R^2$ and $R^3$ together may, for example, form a group of the formula —O(CH$_2$)$_n$O— wherein n represents the integer 1 or 2.

$R^5$ is preferably an ethyl group, an allyl group, a benzyl group or a propargyl group. Most preferably, $R^5$ is an ethyl group. Preferably, $R^4$ is H.

In one embodiment, $R^8$ and $R^9$ are methyl groups, $R^{10}$ is a tert-butyl group or a methyl group, $R^1$ is H and $R^3$ is H. In this embodiment, $R^2$ may, for example, be H, NH$_2$ or OH.

$R^{13}$ is preferably H. $R^{16}$ is preferably H or an alkyl group. Most preferably, $R^{16}$ is H or —C(O)$R^f$, wherein $R^f$ is an alkyl group. Most preferably, $R^{16}$ is H.

The present invention also provides a method of synthesizing a compound having the formula

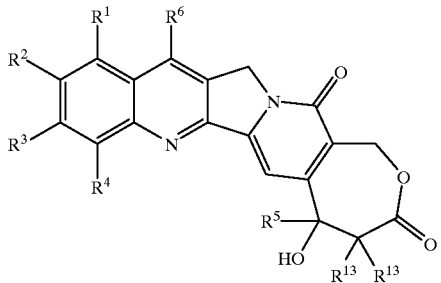

via a cascade radical 4+1 annulation wherein the precursor

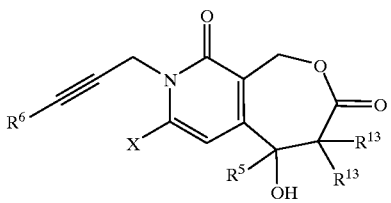

or the precursor

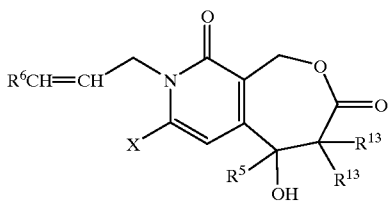

is reacted with an arylisonitrile having the formula

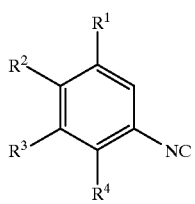

wherein X is a radical precursor. Preferably, X is Cl, Br or I. Most preferably, X is Br or I.

The present invention also provides a compound having the formula

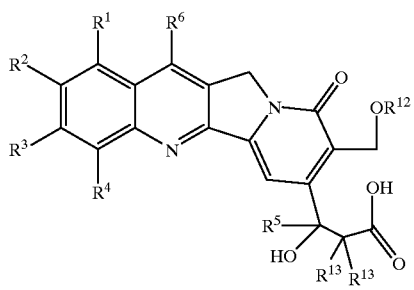
(2)

in racemic form, enantiomerically enriched form or enantiomerically pure form, wherein $R^{12}$ is preferably H or —C(O)$R^f$, —C(O)O$R^d$ or —C(O)N$R^aR^b$; and pharmaceutically acceptable salts thereof.

The present invention further provides compounds having the formulas

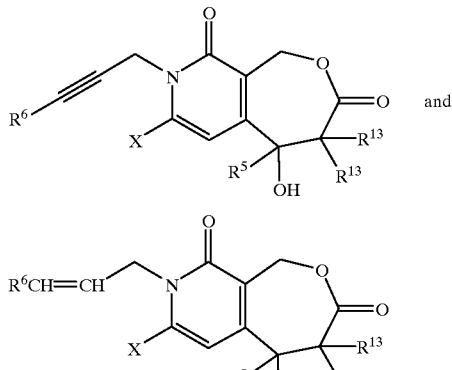

and in racemic form, enantiomerically enriched form or enantiomerically pure form;

Still further, the present invention provides a compound having the formula

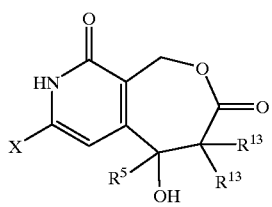

in racemic form, enantiomerically enriched form or enantiomerically pure form

The present invention also provides a compound having the formula

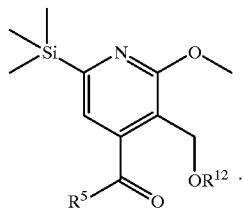

The present invention also provides a compound having the formula

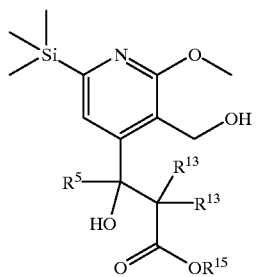

wherein $R^{15}$ is a $C_1$–$C_6$ alkyl group.

The present invention further provides a compound having the formula

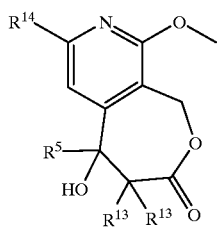

in racemic form, enantiomerically enriched form or enantiomerically pure form, wherein $R^{14}$ is SiMe$_3$, I, or Br.

Still further, the present invention provides a method of synthesizing a compound having the following formula:

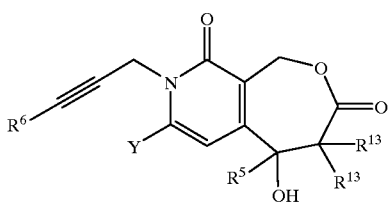

wherein Y is chlorine, bromine or iodine;

comprising the steps of a) treating an enol ether of the structure:

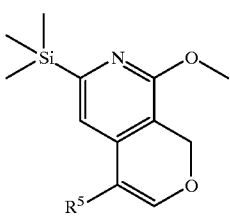

under suitable oxidative cleavage conditions to form a compound having the structure:

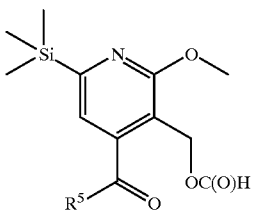

(b) treating the compound formed in step (a) with an organometallic reagent having the structure:

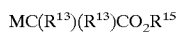

$MC(R^{13})(R^{13})CO_2R^{15}$ wherein M is Li, Na, K, MgY, or ZnY under suitable conditions to form a compound having the structure:

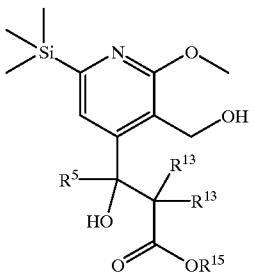

(c) treating the compound formed in step (b) under suitable conditions with acid to form a compound having the structure:

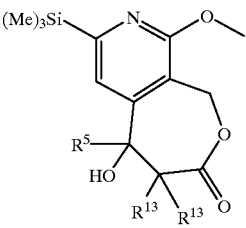

(d) treating the compound formed in step (c) under suitable conditions of halogenative desilylation to form a compound having the structure:

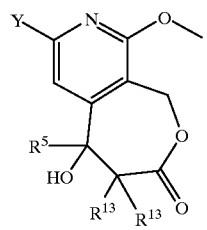

(e) treating the compound in step (d) with acid or iodotrimethylsilane under suitable conditions for demethylation to provide a compound of the following structure:

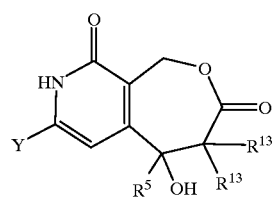

(f) treating the compound in step (e) with a lithium base or a sodium base in the presence of an inorganic lithium salt to deprotonate the nitrogen atom, (g) reacting of the resulting deprotonated species of step (f) with a compound of the following structure:

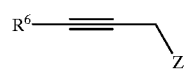

wherein Z is I, Br, Cl, a mesylate group or a tosylate group, and under suitable conditions to cause the formation of the compound of the following structure:

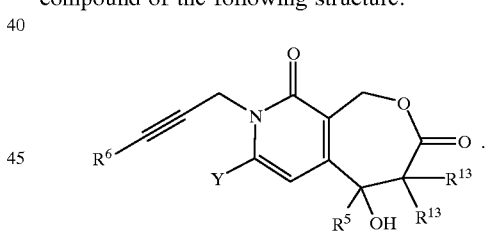

As indicated above, all compounds of the present invention including the β-hydroxylactone group can exist in racemic form, enantiomerically enriched form, or enantiomerically pure form. The formulas of such compounds as set forth herein cover and/or include each such form.

The term "radical precursor(s)" as used herein and as well known to those skilled in the art refers generally to those functional groups that cleave to generate radicals under standard conditions of chain or non-chain radical reactions. Common radical precursors are the halogens (except fluorine), carboxylic acids and derivatives thereof (such as thiohydroxamates), selenophenyl groups, diazonium salts, and the like. See, for example, Giese, B. *Radicals in Organic Synthesis: Formation of Carbon—Carbon Bonds*; Pergamon, Oxford (1986), the disclosure of which is incorporated herein by reference.

The terms "alkyl", "aryl" and other groups refer generally to both unsubstituted and substituted groups unless specified to the contrary. Unless otherwise specified, alkyl groups are hydrocarbon groups and are preferably $C_1$–$C_{15}$ (that is, having 1 to 15 carbon atoms) alkyl groups, and more preferably $C_1$–$C_{10}$ alkyl groups, and can be branched or unbranched, acyclic or cyclic. The above definition of an alkyl group and other definitions apply also when the group is a substituent on another group (for example, an alkyl group as a substituent of an alkylamino group or a dialkylamino group). The term "aryl" refers to phenyl or naphthyl. As used herein, the terms "halogen" or "halo" refer to fluoro, chloro, bromo and iodo.

The term "alkoxy" refers to —$OR^d$, wherein $R^d$ is an alkyl group. The term "aryloxy" refers to —$OR^e$, wherein $R^e$ is an aryl group. The term acyl refers to —$C(O)R^f$. The term "alkenyl" refers to a straight or branched chain hydrocarbon group with at least one double bond, preferably with 2–15 carbon atoms, and more preferably with 2–10 carbon atoms (for example, —CH=$CHR^g$ or —$CH_2$CH=$CHR^g$). The term "alkynyl" refers to a straight or branched chain hydrocarbon group with at least one triple bond, preferably with 2–15 carbon atoms, and more preferably with 2–10 carbon atoms (for example, —C≡$CR^h$ or —$CH_2$—C≡$CR^h$). The terms "alkylene," "alkenylene" and "alkynylene" refer to bivalent forms of alkyl, alkenyl and alkynyl groups, respectively.

The groups set forth above, can be substituted with a wide variety of substituents to synthesize homocamptothecin analogs retaining activity. For example, alkyl groups may preferably be substituted with a group or groups including, but not limited to, a benzyl group, a phenyl group, an alkoxy group, a hydroxy group, an amino group (including, for example, free amino groups, alkylamino, dialkylamino groups and arylamino groups), an alkenyl group, an alkynyl group and an acyloxy group. In the case of amino groups (—$NR^aR^b$), $R^a$ and $R^b$ are preferably independently hydrogen, an acyl group, an alkyl group, or an aryl group. Acyl groups may preferably be substituted with (that is, $R^f$ is) an alkyl group, a haloalkyl group (for example, a perfluoroalkyl group), an alkoxy group, an amino group and a hydroxy group. Alkynyl groups and alkenyl groups may preferably be substituted with (that is, $R^g$ and Rh are preferably) a group or groups including, but not limited to, an alkyl group, an alkoxyalkyl group, an amino alkyl group and a benzyl group.

The term "acyloxy" as used herein refers to the group —$OC(O)R^d$.

The term "alkoxycarbonyloxy" as used herein refers to the group —$OC(O)OR^d$.

The term "carbamoyloxy" as used herein refers to the group —$OC(O)NR^aR^b$.

Amino and hydroxy groups may include protective groups as known in the art. Preferred protective groups for amino groups include tert-butyloxycarbonyl, formyl, acetyl, benzyl, p-methoxybenzyloxycarbonyl, trityl. Other suitable protecting groups as known to those skilled in the art are disclosed in Greene, T., Wuts, P. G. M., *Protective Groups in Organic Synthesis*, Wiley (1991), the disclosure of which is incorporated herein by reference.

In general, $R^1$, $R^2$, $R^3$, $R^6$, $R^7$ and $R^8$ are preferably not excessively bulky to maintain activity of the resultant camptothecin analog. Preferably, therefore, $R^1$, $R^2$, $R^3$, $R^6$, $R^7$ and $R^8$ independently have a molecular weight less than approximately 250. More preferably $R^1$, $R^2$, $R^3$, $R^6$, $R^7$ and $R^8$ independently have a molecular weight less than approximately 200.

Some of the camptothecin analogs of the present invention can be prepared for pharmaceutical use as salts with inorganic acids such as, but not limited to, hydrochloride, hydrobromide, sulfate, phosphate, and nitrate. The camptothecin analogs can also be prepared as salts with organic acids such as, but not limited to, acetate, tartrate, fumarate, succinate, citrate, methanesulfonate, p-toluenesulfonate, and stearate. Other acids can be used as intermediates in the preparation of the compounds of the present invention and their pharmaceutically acceptable salts.

For purification, administration or other purposes, the E-ring (the lactone ring) may be opened with alkali metal such as, but not limited to, sodium hydroxide or calcium hydroxide, to form opened E-ring analogs of compounds of formula (1) as set forth in the compounds of formula (2). The intermediates thus obtained are more soluble in water and may be purified to produce, after treatment with an acid, a purified form of the camptothecin analogs of the present invention.

The E-ring may also be modified to produce analogs of compounds of formula (1) with different solubility profiles in water or other solvents. Methods to achieve this goal include, but are not limited to, opening the E-ring with hydroxide or a water-soluble amino group or functionalizing the hydroxy group at position 20 of the E-ring with a water-soluble group such as a polyethylene glycol group or an acyl group. Such groups can be introduced either on the homocamptothecin derivative or at an earlier stage in the synthesis. The analogs thus prepared act as pro-drugs. In other words, these analogs regenerate the compounds of formula (1) (with the closed E-ring structure) when administered to a living organism. See, Greenwald, R. B. et al., *J. Med. Chem.*, 39, 1938 (1996). Alkyl esters resulting from acylation at C20, for example, will result in more lipophilic pro-drugs that may not hydrolyze until the alkyl group is enzymatically cleaved.

The present invention also provides a method of treating a patient, which comprises administering a pharmaceutically effective amount of a compound of formulas (1) and/or (2) or a pharmaceutically acceptable salt thereof. The compound may, for example, be administered to a patient afflicted with cancer and/or leukemia. The compounds of the present invention may also act as antiviral (for example, anti-HIV) agents and antiparasitic agents. The compounds of formulas (1) and/or (2) may be administered by any conventional route of administration, including, but not limited to, intravenously, intramuscularly, orally, subcutaneously, intratumorally, intradermally, and parenterally. The pharmaceutically effective amount or dosage is preferably between 0.01 to 60 mg of one of the compounds of formulas (1) and (2) per kg of body weight. More preferably, the pharmaceutically effective amount or dosage is preferably between 0.1 to 40 mg of one of the compounds of formulas (1) and (2) per kg of body weight. In general, a pharmaceutically effective amount or dosage contains an amount of one of the compounds of formulas (1) and/or (2) effective to display antileukemic, antitumor (anticancer), antiviral and/or antiparisitic behavior. Pharmaceutical compositions containing as an active ingredient one of the compounds of formulas (1) and/or (2) or a pharmaceutically acceptable salt thereof in association with a pharmaceutically acceptable carrier or diluent are also within the scope of the present invention.

The present invention also provides a pharmaceutical composition comprising any of the compounds of formulas (1) and (2) and a pharmaceutically acceptable carrier. The composition may, for example, contain between 0.1 mg and 3 g, and preferably between approximately 0.1 mg and 500 mg of the compounds of formulas (1) and/or (2), and may be constituted into any form suitable for the mode of administration.

The structural modifications of the present invention were found to prevent high affinity binding between the carboxylate form of a camptothecin analog and HSA, while at the same time promoting lactone interactions with erythrocytes. An additional consideration in the design of plasma and blood-stable camptothecins concerns the structure of the E-ring. The A,B,E- or B,E-ring modified camptothecins of the present invention: 1) display enhanced stability in the presence of HSA through elimination or minimization of the highly preferential binding by HSA of carboxylate over lactone forms; 2) display high levels of lipophilicity which promote reversible associations of the lactone forms of the drugs with red blood cells, thereby slowing and restricting the extent of drug hydrolysis; and 3) display improved stability in aqueous solution.

We further discovered that the novel blood-stable silyl-substituted homocamptothecin (referred to herein as β-hydroxylactone silatecans or homosilatecans (hST)) derivatives of the present invention can be prepared by significant modification of a total synthesis approaches set forth in U.S. patent application Ser. No. 09/212,178, entitled CAMPTOTHECIN ANALOGS AND METHODS OF PREPARATION THEREOF and filed Dec. 15, 1998 and U.S. patent application Ser. No. 09/007,872, entitled NOVEL INTERMEDIATES IN THE SYNTHESIS OF CAMPTOTHECIN AND RELATED COMPOUNDS AND SYNTHESIS THEREOF and filed Jan. 15, 1998 the disclosure of which are incorporated herein by reference. Novel intermediates were synthesized to carry out the cascade radical annulation of the present invention.

Several model compounds of the present invention, as described in the formula below, were studied extensively.

| | $R^6$ | $R^2$ | name |
|---|---|---|---|
| 1b | SiMe$_2$$^t$Bu | NH$_2$ | DB-90 |
| 1d | SiMe$_3$ | NH$_2$ | DB-38 |
| 1f | SiMe$_2$$^t$Bu | OH | DB-91 |
| 1g | SiMe$_2$$^t$Bu | H | DB-81 |
| 1h | SiMe$_3$ | H | DB-33 |

The novel homocamptothecins of the present invention contain A,B- or B-ring modifications which decrease the preferential carboxylate over lactone binding by human albumin. These modifications in the A,B-rings also markedly enhance lipophilicity and promote lactone associations with lipid bilayers present in blood. The new compounds also contain an expanded β-hydroxylactone E-ring which improved the overall stability of the agents without loss of potency. In cytotoxicity assays using MDA-MB-435 breast cancer cells, the E-ring expanded β-hydroxylactone silatecans of the present invention display IC$_{50}$ values in the range of 2 to 115 nM. The compounds of the present invention (several of which are described in the formula above), as a result of their novel structural substitutions, have superior human plasma and human blood stabilities than the agents described by Lavergne et al.

Synthesis of the novel A,B,E-ring modified and B,E-ring modified camptothecins of the present invention has led to the identification of the most blood-stable camptothecins displaying intrinsic potency yet to be identified. An additional benefit of these new agents is that they do not display any significant interspecies variations in blood stabilities such as those of 9-AC and camptothecin described in Mi, Z. and Burke, T. G. "Marked Interspecies Variations Concerning the Interactions of Camptothecin with Serum Albumins: A Frequency-Domain Fluorescence Spectroscopic Study", Biochemistry, 33: 12540–12545 (1994). This very attractive feature should greatly facilitate the drug development process and the translation of experimental observations and dosing schedules developed in animal models to the clinic.

DETAILED DESCRIPTION OF THE INVENTION

Method of Preparation

Figure 1:
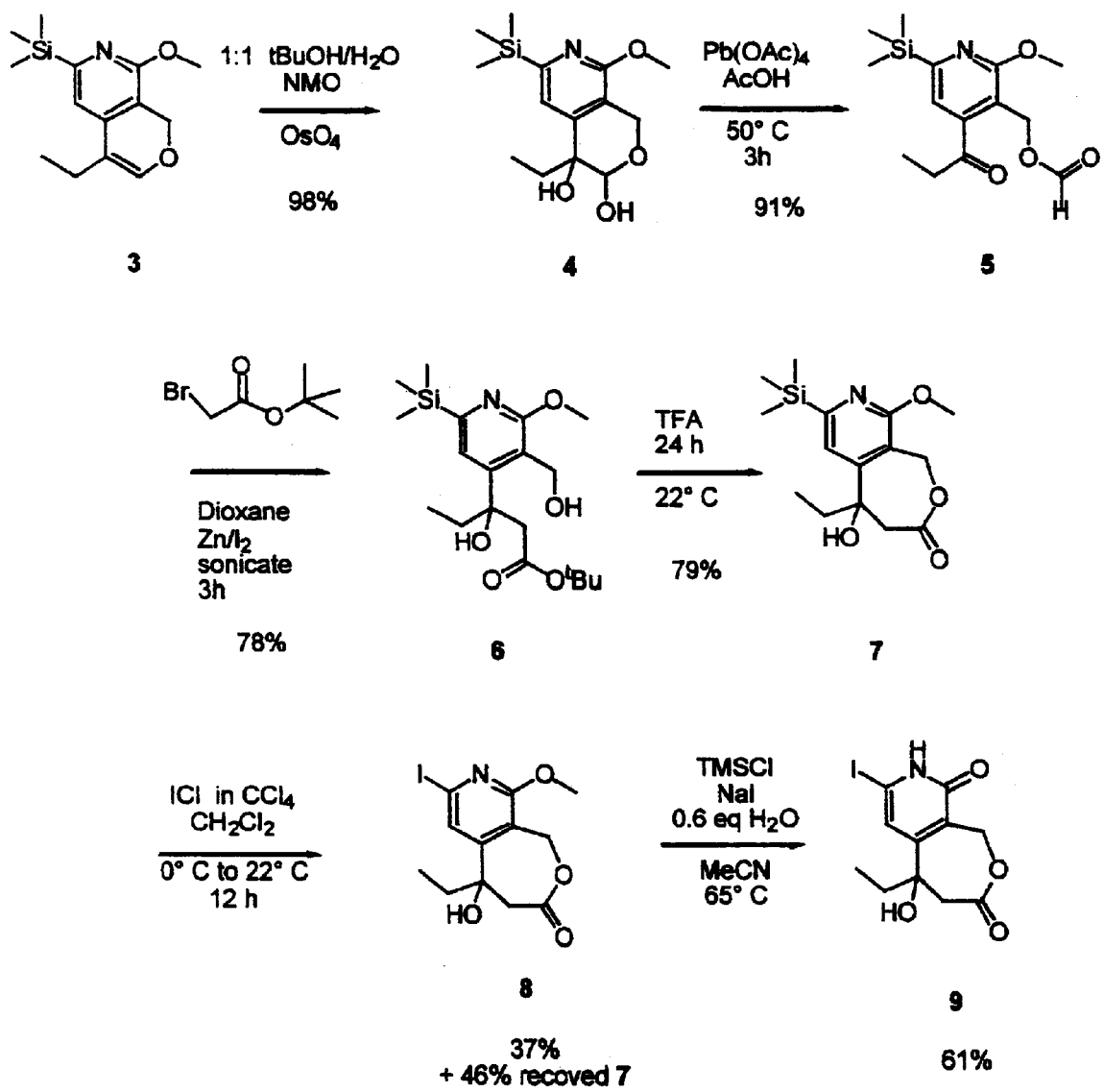
FIG. 1 illustrates synthesis of precursors for the cascade radical reactions.
Figure 2A:
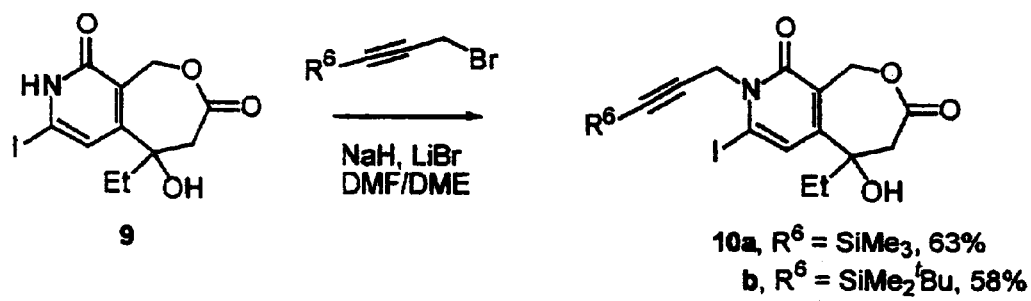
FIGS. 2a and 2b illustrate synthesis of new AB-ring modified homocamptothecin/homosilatecan derivatives.
Figure 2A:
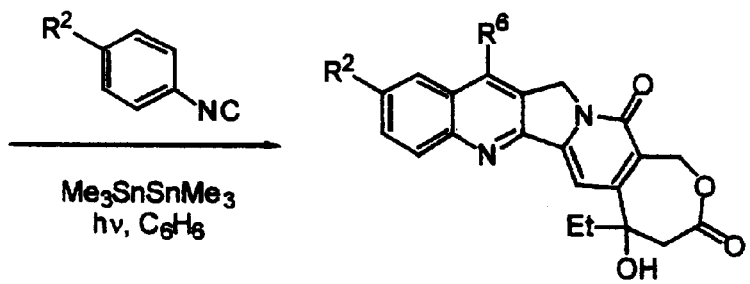

The compounds of formula 1 in the present invention can be prepared according to the synthetic schemes outlined in FIGS. 1 and 2. FIG. 1 shows the synthesis of a key iodopyridone 9, which can be used to make the compounds of formula 1. The synthesis of 9 starts from enol ether 3, an intermediate in the synthesis of camptothecin and analogs. See U.S. patent application Ser. No. 09/007,872, the disclosure of which is incorporated herein by reference. Dihydroxylation followed by oxidative cleavage provides the keto formate 5, which is then extended by a Reformatsky reaction to give 6. Conveniently, the formyl group is cleaved in this reaction, and acid promoted cleavage of the t-butyl ester directly results in β-hydroxylactone 7. This compound is then converted to the iodopyridone 9 by a sequence of 1) iodinative desilylation, and 2) demethylation.

FIG. 2a shows the conversion of iodopyridone 9 to several model AB modified homocamptothecin derivatives. N-Propargylation of 9 under optimized conditions provides radical precursors 10a,b. The cascade radical annulations of these precursors with the indicated isonitriles give products 1a,c,e,g,h. Products 1a,c,e were then deprotected by standard means to provide the target drug candidates 1b,d,f in the indicated overall yields. Compounds 1g and 1h do not require deprotection. The synthesis of additional novel compounds of the present invention are described in the Examples section of the present application.

Lavergne and coworkers disclose two ways to make homosilatecan derivatives, but both have serious limitations. The first involves the conversion of a standard camptothecin derivative to a homocamptothecin derivative by a series of steps involving disassembly of the normal lactone and reassembly of the homologated lactone. This route is limited because it requires an existing camptothecin to start. Furthermore, many existing camptothecin derivatives bear substituents that would not be expected to survive the harsh conditions of the refashioning of the lactone. This process requires reducing, oxidizing, strong acid, and strong base steps. The second route involves a total synthesis using a palladium catalyzed cyclization to form ring C. This route is limited by the availability of A-ring precursors and by the ability of the substituents thereon to survive the many subsequent steps of the synthesis. Furthermore, the synthesis does not appear to offer the possibility to introducing many B ring substituents, including the substituents described herein.

Figure 2B:
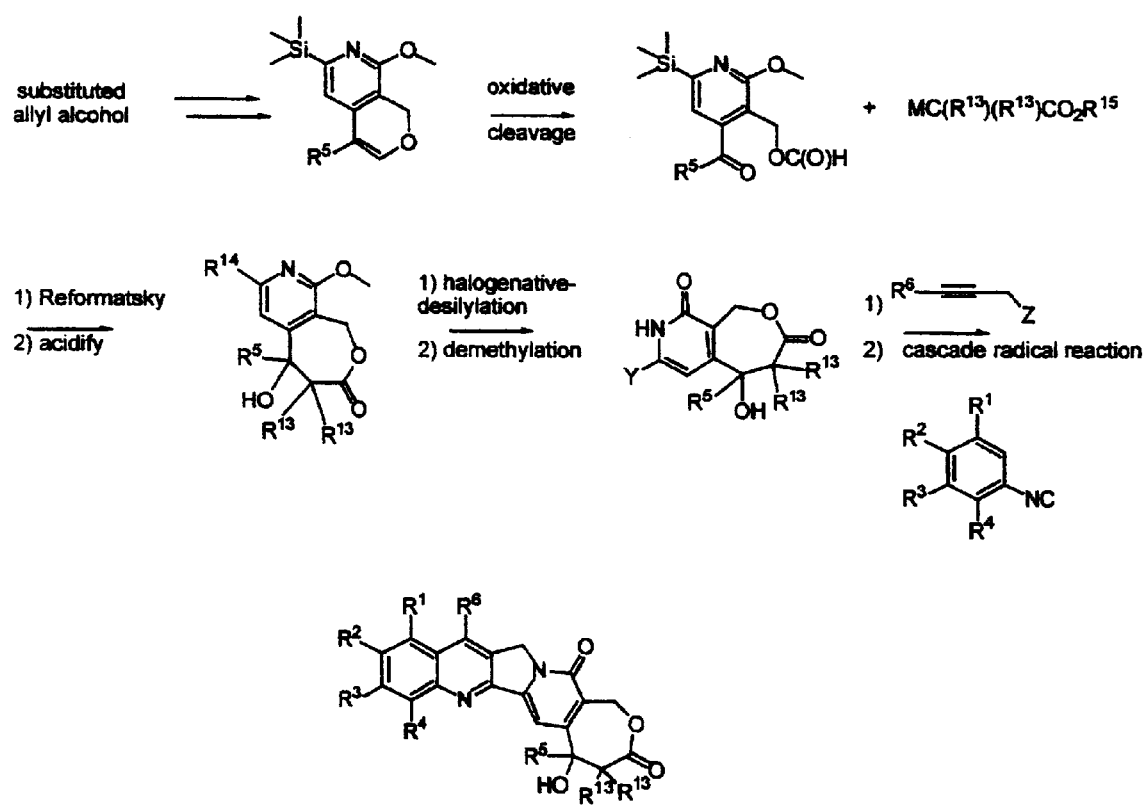

In contrast, the radical cascade synthetic schemes of the present invention are much more tolerant and flexible and can be used to make homocamptothecin derivatives with many A-, B-, or A/B substitution patterns, as shown, for example, in FIG. 2b. Generally, various reagents can be used in the radical cascade including, but not limited to, hexamethylditin, hexamethyldisilane, or tetrakis (trimethylsilyl)silane. The source of energy for this reaction can be a sun lamp or an ultraviolet lamp. The temperature is preferably set between approximately 25 and 150° C. More preferably, the temperature is set at approximately 70° C. There are generally no limitations upon the choice of solvent used other than inertness to the radical cascade. Preferred solvents include benzene, toluene, benzotrifluoride, acetonitrile, THF and tert-butanol. Also, there is very broad latitude in the choice of substituents on the alkyne ($R^6$) and the isonitrile ($R^1$–$R^4$) in the synthetic schemes of the present invention because of the mildness of the reaction conditions. In addition, in rare cases where suitable propargyl derivatives are not readily prepared, allyl derivatives can be substituted instead and the same final products are formed, albeit in lower yield.

The substituent on C20 ($R^5$) can also be widely varied since it derives from readily available allyl alcohols. Substituted esters can also be used in the Reformatsky reaction to provide compounds with subsitutents on C20a ($R^{13}$). While the compounds of this invention might be used in racemic form for chemotherapy, it is more preferable to use samples that are exclusively or predominately the biologically active enantiomer at C20. Because of a change in priorities in the Cahn-Ingold-Prelogs Rules for assignment of absolute configuration, the C20 S enantiomer of a standard camptothecin generally has the same relative configuration as the C20 R enantiomer of the corresponding homocamptothecin. Racemic or enantiomerically enriched samples of homocamptothecin derivatives can be separated into their individual components by standard methods of liquid chromatography using commercially available chiral columns. See Lavergne, O.; et al., "Homocamptothecins: Synthesis and Antitumor Activity of Novel E-Ring Modified Camptothecin Analogs," *J. Med. Chem.*, 41, 5410-5419 (1998).

Human Blood Stabilities of Camptothecins and the Basis for the Rational Design of Blood-Stable Homosilatecans With High Potency Recently the intrinsic fluorescent emissions from the lactone and carboxylate forms of camptothecin and related analogs have been studied in order to elucidate their markedly different interactions with human blood components. Burke, T. G. and Mi, Z., "Ethyl substitution at the 7 position extends the half-life of 10-hydroxycamptothecin in the presence of human serum albumin," *J. Med. Chem.* 36: 2580–2582 (1993); Burke, T. G., Mishra, A. K., Wani, M. C. and Wall, M. E., "Lipid bilayer partitioning and stability of camptothecin drugs," *Biochemistry.* 32: 5352–5364 (1993); Burke, T. G. and Mi, Z.: "Preferential Binding of the Carboxylate Form of Camptothecin by Human Serum Albumin," (1993a) *Anal. Biochem.* 212, 285–287; Burke, T. G. and Mi, Z., "The Structural Basis of Camptothecin Interactions with Human Serum Albumin: Impact on Drug Stability," (1994) *J. Med. Chem.* 37, 40–46; Burke, T. G. Munshi, C. B., Mi, Z., and Jiang, Y., "The Important Role of Albumin in Determining the Relative Human Blood Stabilities of the Camptothecin Anticancer Drugs," (1995) *J. Pharma. Sci.* 84, 518–519; Mi, Z. and Burke, T. G., "Differential Interactions of Camptothecin Lactone and Carboxylate Forms with Human Blood Components," (1994a)

Biochemistry, 33, 10325–10336; Mi, Z. and Burke, T. G., "Marked Interspecies Variations Concerning the Interactions of Camptothecin with Serum Albumins: A Frequency-Domain Fluorescence Spectroscopic Study," (1994b) Biochemistry 33, 12540–12545; and Mi, Z., Malak, H., and Burke, T. G., "Reduced Albumin Binding Promotes the Stability and Activity of Topotecan in Human Blood," (1995) Biochemistry, 34, 13722–13728, the disclosures of which are incorporated herein by reference.

In phosphate buffered saline (PBS) at pH 7.4, frequency-domain fluorescence lifetime spectroscopy reveals that human serum albumin (HSA) preferentially binds the carboxylate form of camptothecin with a 200-fold higher affinity than the lactone form. These interactions result in camptothecin opening more rapidly and completely in the presence of HSA than in the absence of the protein. In human plasma, pH 7.4 and 37° C., camptothecin lactone opens rapidly and completely to the carboxylate form with a $t_{1/2}$ value of 11 min and an almost negligible percentage of lactone at equilibrium value of 0.2%. In whole blood versus plasma, camptothecin displayed enhanced stability ($t_{1/2}$ value of 22 min and a percentage of lactone at equilibrium value of 5.3%). The enhanced stability of camptothecin lactone in human blood was found to be a result of drug associations with the lipid bilayers of red blood cells. Camptothecin binds erythrocyte membranes, the drug localizes within the acyl chain region, and accordingly remains protected from hydrolysis.

The human blood stabilities of the several camptothecin analogs of clinical interest have also been compared. As was observed in the case of camptothecin, 9-aminocamptothecin (9-AC) was observed to hydrolyze almost completely (>99%) in PBS solution containing HSA. Although no attempt was made to spectroscopically quantify the relative binding affinities of the lactone and carboxylate forms of the 9-amino congener (because of the significantly reduced fluorescence quantum yields of 9-AC lactone and carboxylate species relative to camptothecin), HPLC data were consistent with HSA preferentially binding the carboxylate form of this agent over its lactone form. In plasma it was observed that >99.5% of the 9-amino analog of camptothecin converted to carboxylate, a finding which again closely parallels stability data obtained using camptothecin. In whole blood, <0.5% and 5.3% are the fractions of 9-aminocamptothecin and camptothecin, respectively, which remained in the lactone form at equilibrium. The approximately 10-fold higher level of lactone remaining at equilibrium for camptothecin relative to 9-aminocamptothecin may, in part, be accounted for by the enhanced lipophilicity and greater ability of camptothecin to transition from the aqueous environment and into erythrocyte membranes present in whole blood.

In contrast to the low levels of lactone remaining at equilibrium in whole human blood for camptothecin and 9-aminocamptothecin (<0.5% and 5.3%, respectively), topotecan (11.9%), CPT-11 (21.0%), and SN-38 (19.5%) all display improved blood stabilities. While lactone levels at equilibrium for topotecan are 20-fold greater than for 9-aminocamptothecin, the corresponding levels of lactone for CPT-11 and SN-38 are approximately 40-fold greater than in the case of 9-aminocamptothecin. The significant gains in the relative stabilities of topotecan, CPT-11, and SN-38 can be correlated to their favorable interactions with HSA. It is believed that structural substituents at the 7- and 9-positions hinder and prevent the preferential binding of the carboxylate drug forms by HSA. The technique of time-resolved fluorescence anisotropy has recently been used to demonstrate that, under experimental conditions where camptothecin carboxylate associates with HSA and tumbles in solution closely associated with the protein, the carboxylate forms of topotecan and CPT-11 do not associate with HSA. In the case of SN-38, direct spectroscopic evidence has been obtained which indicates that HSA preferentially binds the lactone form of this agent, thereby shifting the lactone-carboxylate equilibrium to the lactone.

These observations indicate that HSA plays an important role in determining the relative human blood stabilities of the camptothecins. In the cases of camptothecin and 9-aminocamptothecin, the protein acts as a sink for the carboxylate drug form, binding the opened ring species and thereby shifting the lactone-carboxylate equilibria to the right. However, in the cases of topotecan, CPT-11, and SN-38, no such preferential binding of the carboxylate drug form by HSA is observed. Opposite to the situation with camptothecin and its 9-amino analogue, HSA preferentially binds the lactone form of SN-38 which thereby promotes higher circulatory levels of this biologically active species.

The rapid and extensive loss of active drug that occurs with clinically relevant camptothecins indicates that it would be highly advantageous to identify camptothecins with improved human blood stabilities.

In the present studies we modified camptothecin in the A and B rings with the effect of: 1) reducing protein binding; 2) enhancing lipophilicity; and 3) producing both a concomitant reduction in carboxylate binding to human albumin while also enhancing lipophilicity. We also included an expanded E-ring in the design of the present compounds. Our studies have led to the design of novel A,B,E-ring modified camptothecins which are the most blood-stable and intrinsically potent camptothecin analogs yet to be identified, with blood stability parameters outcompeting the prior art compound homocamptothecin as well A,B-ring modified camptothecin analogs containing a conventional α-hydroxylactone functionality. The novel camptothecin analogs of the present invention display unique properties such as superior human blood stabilities in combination with high anticancer activities.

Figure 3:
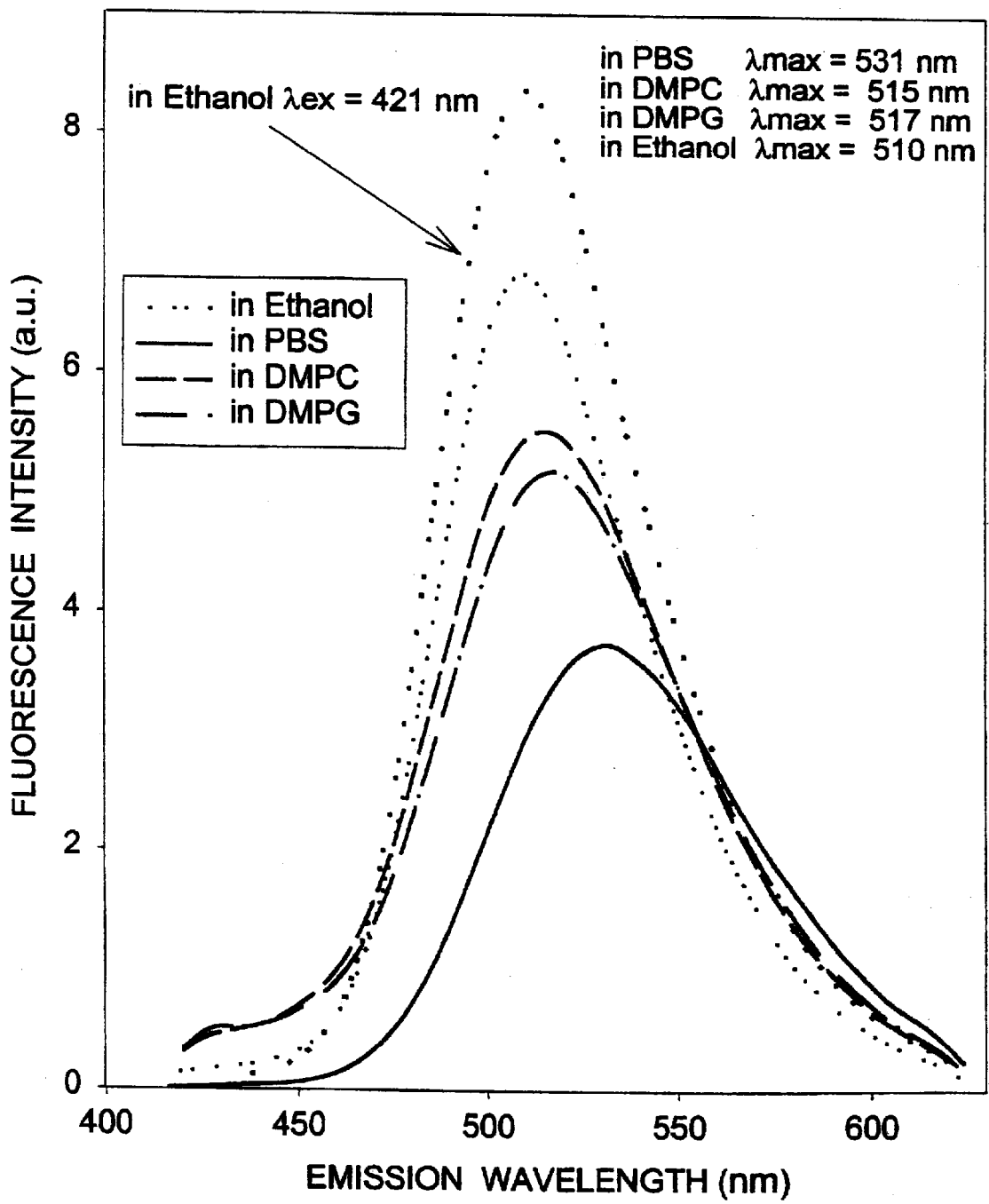
FIG. 3 illustrates a typical fluorescence fluorescence emission spectra for a homosilatecan (1 μM 7-trimethylsilyl-10-aminohomocamptothecin (DB-38)) in the presence and absence of lipid bilayer membranes.

Fluorescence Anisotropy Titration Demonstrates that the Novel Homosilatecans of the Present Invention Display a Broad Range of Equilibrium Association Constants for Lipid Vesicles and that E-Ring Expansion Enhances the Lipophilicity of Silatecans FIG. 3 depicts the fluorescence emission spectra of 1 $\mu$M DB-38 in phosphate buffered saline (PBS) and in lipid bilayers. The data indicate that upon introduction of lipid bilayers into the sample there is an increase in the fluorescence emission of the compound, indicative of an interaction between the drug and the membrane. Upon changing the solvent to ethanol the fluorescence also changes. In each case with membranes there is a marked increase in fluorescence intensity as the drug partitions into the lipid bilayer microenvironment. In each case there is also a prominent blue-shifting or shift in the emission spectra to lower wavelength upon drug interaction with membrane (see Table 1). The spectral data presented in FIG. 3 indicate that homosilatecans are fluorescent and that the spectral parameters of the drugs change upon addition of lipid bilayer membranes to the samples. Table 1 found below compares the maximum excitation and emission wavelengths of the new homosilatecan analogs. We also examined the membrane interactions of the ring-opened forms of DB-90 and DB-91, and our results indicate the similar spectral shifting for the ring-opened species.

TABLE 1

Fluorescence Spectral Parameters for Homosilatecans
(DB-38, DB-81, DB-90, DB-91) in Solution and Bound to
DMPC and DMPG SUVs.

| Compound (S) | Excitation (nm) PBS | Emission (nm) PBS | Emission (nm) DMPC | Emission (nm) DMPG |
|---|---|---|---|---|
| DB-38 | 410 | 531 | 515 | 517 |
| DB-81 | 380 | 452 | 443 | 442 |
| DB-90 | 402 | 535 | 513 | 512 |
| DB-91 | 394 | 554 | 441 | 426 |

The intrinsic fluorescent nature of the lactone and carboxylate forms of homosilatecans allows for the sensitive method of steady-state fluorescence anisotropy titration to be employed to determine the strength of the binding interactions of the various analogs with lipid bilayers.

A steady-state fluorescence anisotropy (a) measurement is related to the rotational rate of the fluorescent molecule through the Perrin Equation:

$$a_o/a = 1+(\tau/\phi)$$

where $a_o$ is the limiting fluorescence anisotropy in the absence of depolarizing rotations, $\tau$ is the excited-state lifetime, and $\phi$ is the rotational correlation time of the fluorophore. The above equation states that changes in either the $\tau$ or $\phi$ values of a fluorescent compound can modulate its steady-state anisotropy.

The excited-state lifetime values of camptothecin in PBS, glycerol, and methanol were examined at 37° C. The lifetime values were determined to be 4.7 ns, 3.8 ns, and 3.5 ns, respectively. Similarly, the lifetime value of camptothecin when associated with DMPC bilayers was measured at 37° C., and the average value for membrane-bound drug was found to be 3.7 ns.

Thus the lifetime measurements described above indicate that the excited-state lifetime of camptothecin is relatively insensitive to alterations in microenvironment (for example, a change in solvent or fluorophore relocation from an aqueous milieu to a phospholipid membrane). For a fluorophore having a $\tau$ value that remains relatively constant during a transition which strongly impacts on its rotational motion (such as a change in solvent viscosity or fluorophore binding to large macromolecular assemblies such as liposomal particles), the Perrin equation indicates a direct relationship between a and $\phi$ values will exist (that is, as the $\phi$ value of the fluorescent compound increases, then so too does its steady-state anisotropy value).

It has been shown that the steady-state fluorescence anisotropy values of camptothecin analogs and novel homosilatecans are highly sensitive to solvent viscosity and to associations with small unilamellar lipid vesicles. For example, topotecan has an a value of 0.008 in PBS, but its a value increases 9-fold and 40-fold in the viscous solvents octanol and glycerol, respectively. A 21-fold enhancement in the a value of camptothecin is observed upon binding of drug to vesicles composed of either DMPC or DMPG. Because of the sensitivity of a of the camptothecin drugs to membrane associations, the method of fluorescence anisotropy titration was employed to study the equilibrium binding of camptothecin analogs with lipid bilayers. The experiment includes determining the a values for a set of samples where the drug concentration in each was held constant (typically 1 or 2 $\mu$M), while the lipid concentration among the members of a set was varied from 0 to 0.29 M.

Figure 4:
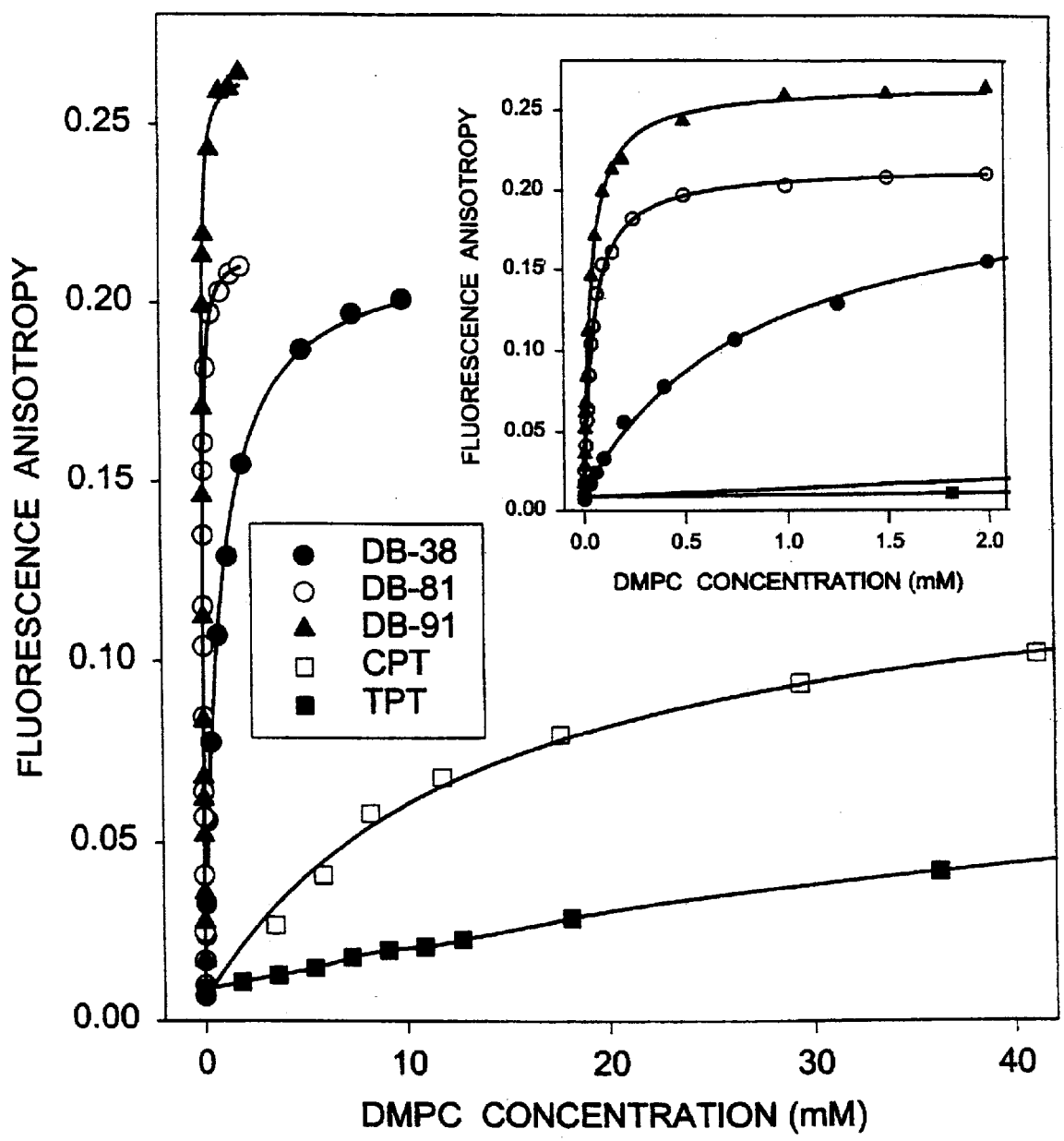
FIG. 4 illustrates a comparison of the equilibrium binding of four novel homosilatecans to SUVs composed of electroneutral dimyristoylphosphatidylcholine (DMPC) in PBS with data acquired for camptothecin (CPT) and topotecan (TPT) as well.

As a consequence of the brilliant fluorescence emissions from the newly synthesized homosilatecans (a summary of the spectral parameters can be found in Table 1), the lipid bilayer adsorption isotherms summarized in FIG. 4 were relatively free from any background signal. The method of fluorescence anisotropy titration was used to construct the adsorption isotherms. The experiments were conducted at drug concentrations of 1 $\mu$M in PBS buffer (37° C.). The anisotropy values of DB-38, DB-90 and DB-91 titrated much more rapidly than those of camptothecin or topotecan, indicating that the novel homosilatecans have much stronger interactions with these membranes than camptothecin and topotecan. Because of the potential of the lactone ring of the homosilatecans and camptothecins to hydrolyze in PBS, anisotropy values at each lipid concentration were determined immediately (approx. 1 min.) following the addition of the lactone form of each agent to the liposome suspension as to minimize any possibility of conversion to the carboxylate form. Using drug concentrations of 1 $\mu$M and long pass filters to isolate emitted light from background signal (that is, scattered exciting light and extraneous fluorescence signal resulting from the possible presence of impurities), signal levels from drugs dissolved in PBS buffer were typically 99.97% in the absence of membrane and greater than 98% in the presence of membrane. Adsorption isotherms were used to determine overall association constants for the homosilatecan, silatecan, and camptothecin drugs. Overall association constants are defined as:

$$K=[A_B]/[A_F][L]$$

where [$A_B$] represents the concentration of bound drug, [$A_F$] represents the concentration of free drug, and [L] represents the total lipid concentration in the vesicle suspension. This equation is valid when the concentration of free lipid is approximately equal to the concentration of total lipid (that is, the concentration of free lipid is in significant excess over the concentration of bound drug) Provided this condition is satisfied, K may be determined from the inverse of the slope of a double reciprocal plot. In such a double reciprocal plot, 1/fraction of the total drug bound is plotted vs. 1/lipid concentration, with a y-intercept value of 1 (for a system displaying binding site homogeneity). Such double-reciprocal plots for the associations of the new homosilatecans analogs (both lactone and carboxylate forms) with DMPC and DMPG small unilamellar vesicle (SUV) preparations were linear with good correlation coefficients. The linearity of these plots, as well as the corresponding plots for drug associations with other types of membrane preparations, indicates that fluorophore binding at these lipid concentrations is adequately described by the above equation.

The studies summarized in Table 2 examine the structural basis of homosilatecan associations for lipid bilayers. Two types of membranes were included in these studies which were conducted under near physiological conditions of pH and temperature; these membranes include fluid-phase and electroneutral L-α-dimyristoylphosphatidylcholine (DMPC); and fluid-phase and negatively-charged L-α-dimyristoylphosphatidylglycerol (DMPG). DMPC and DMPG have identical chain length but the charges on their head groups differ.

TABLE 2

Overall association constants for homosilatecans and camptothecin analogs interacting with unilamellar vesicles of electroneutral DMPC and negatively charged DMPG in PBS at pH 7.4 and 37° C.

| Compound | $K_{DMPC}$ ($M^{-1}$) | $K_{DMPG}$ ($M^{-1}$) |
|---|---|---|
| DB-38 | 1400 | 800 |
| DB-81 | 14400 | 18500 |
| DB-90 | 8600 | 9300 |
| DB-91 | 8000 | 4300 |
| DB-90 carboxylate form | 770 | 80 |
| DB-91 carboxylate form | 700 | 100 |
| Topotecan | 10 | 50 |
| Camptothecin | 100 | 100 |

In the studies of Table 2, binding isotherms were constructed using the method of fluorescence anisotropy titration as discussed above, and K values were determined from the slopes of the double-reciprocal plots. The K values are subject to 10% uncertainty. One of the most striking features of the data contained in Table 2 is the strong modulation which can be achieved through the creation of A,B,E-ring modified camptothecins (for example, the homosilatecans known as DB-38, DB-90, and DB-91) or B,E-ring modified camptothecins (for example, the homosilatecan known as DB-81). Homosilatecans containing either a sole substitution at the 7 position or dual substitution at the 7 and 10 positions have been created and found to display very high lipophilicities. Included in Table 2 are camptothecin compounds (topotecan and camptothecin). For DB-81, the lipophilicity for DMPC membranes relative to corresponding value for topotecan increases over 1,400-fold. Data for these agents were included to show the highly lipophilic nature of the new homocamptothecins relative to compounds such as topotecan and camptothecin. From Table 2, it is clear that the compounds of the present invention are much more lipophilic than either camptothecin or topotecan.

Other interesting and unexpected findings are apparent upon inspection of the data contained in Table 2. Comparison of the $K_{DMPC}$ values for two homosilatecan with their corresponding silatecan analogs (where the E-ring systems are β-hydroxylactone versus α-hydroxylactone moieties, respectively) indicate that the homocamptothecins display greater lipophilicity. For example, the $K_{DMPC}$ values of the silatecan counterparts of DB-38 (CHJ-792, $K_{DMPC}$=820 $M^{-1}$) and DB-91 (DB-67, $K_{DMPC}$=2,500 $M^{-1}$) are approximately 2-fold to 3-fold less than for the corresponding homosilatecans. Thus, for DB-38 and DB-91 the expanded E-ring is a favorable consideration for membrane binding which, in turn, promotes drug stability in human blood.

Another surprising trend was observed for the homosilatecans when the carboxylate forms of the drugs were studied. A 3-fold decrease in the affinity for DMPC upon the opening of the lactone ring of camptothecin has previously been observed. Burke, T. G., Mishra, A. K., Wani, M. C. and Wall, M. E., "Lipid bilayer partitioning and stability of camptothecin drugs," Biochemistry. 32: 5352–5364 (1993). For the DB-90 and DB-91 homocamptothecins, we observe a 10-fold decrease in DMPC binding upon ring opening. Hence, the homosilatecans not only display markedly enhanced lipophilicity but the levels of differential binding between the lactone and carboxylate forms appear to be significantly greater (10-fold versus 3-fold) relative to camptothecins containing α-hydroxylactone ring systems. The two considerations described above (high lipophilicity and higher differential binding of lactone over carboxylate forms) are contributing factors to the optimized blood stabilities which the homosilatecans display over camptothecin and homocamptothecin.

Figure 5:
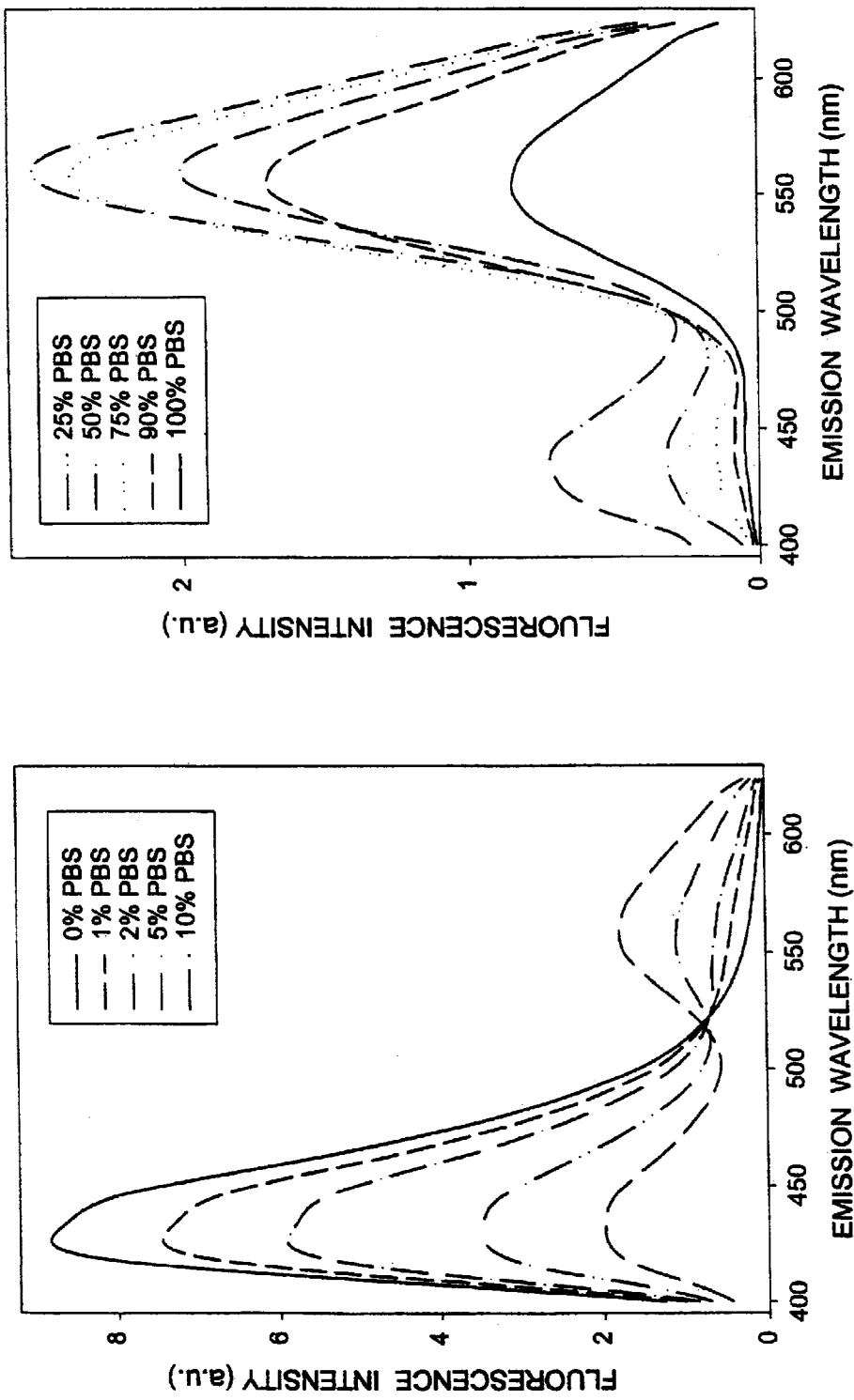
FIG. 5 illustrates the marked dependence of the the fluorescence emission spectra of 1 μM 7-t-butyldimethylsilyl-10-hydroxyhomocamptothecin (DB-91) on the presence of water.

Direct Fluorescence Spectral Assessment of the Extensive Membrane Interations of the DB-91 Homosilatecan With Red Blood Cells FIG. 5 illustrates the fluorescence emission spectra of 1 μM 7-t-butyldimethylsilyl-10-hydroxy-homocamptothecin (DB-91) in solutions of phosphate-buffered saline (PBS) at pH 7.4, ethanol, and admixtures thereof. All spectra were recorded using exciting light of 394 nm at 37° C. The emission maxima for DB-91 in PBS is 554 nm, but this value shifts significantly to a $\lambda_{max}$ of approximately 410 nm in anhydrous ethanol. Because DB-91 contains a 10-hydroxy functionality, the possibility exists that fluorescence can occur from two distinct species. In an aprotic solvent or non-aqueous microenvironment a protonated (with respect to the 10-hydroxy functionality) species predominates, while in protic solvents such as water a deprotonated excited-state complex predominates. The 554 nm peak is correlated with the deprotonated excited-state complex while the $\lambda_{max}$ of approximately 410 nm correlates with the protonated excited-state complex. The formation of the deprotonated excited-state complex is greatly facilitated by the presence of water; even at small amounts of water such as 1% a peak is apparent around 550 nm which correlates with the water-facilitated formation of the deprotonated excited-state complex. The spectral sensitivity of DB-91, and other members of the camptothecin family containing the 10-hydroxy functionality, provides a useful approach for studying the partitioning of drug from an aqueous environment into a hydrophobic environment such at the surface of a red blood cell.

Figure 6:
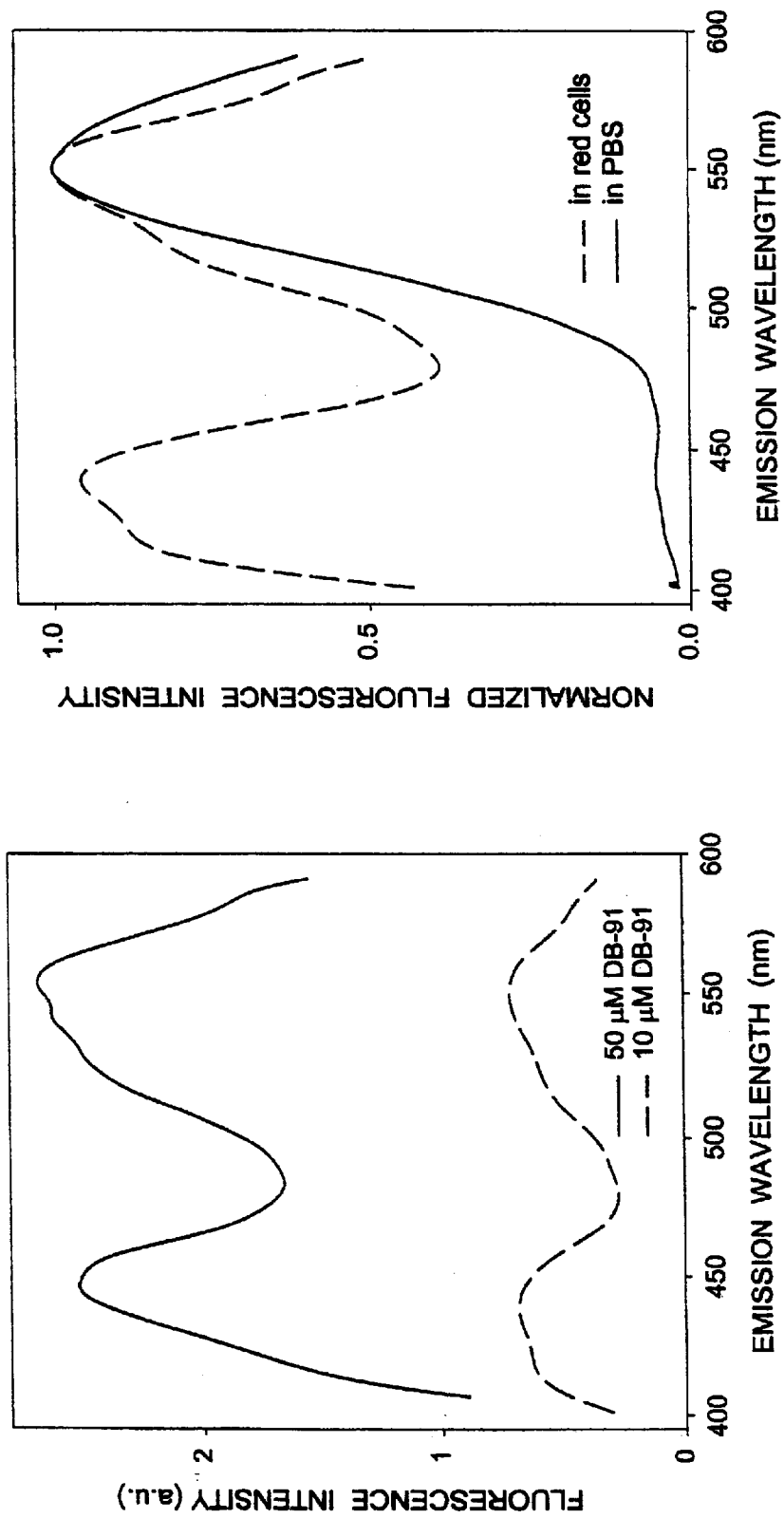
FIG. 6 illustrates the fluorescence emission spectra of 1 μM 7-t-butyldimethylsilyl-10-hydroxyhomocamptothecin (DB-91) in solutions of phosphate-buffered saline (PBS) at pH 7.4 and in PBS at pH 7.4 containing albumin-free red blood cells at a concentration of (10±1)×10$^6$ cell/μL.

FIG. 6 shows the fluorescence emission spectra of 1 μM 7-t-butyldimethylsilyl-10-hydroxy-homocamptothecin (DB91) in solutions of phosphate-buffered saline (PBS) at pH 7.4 and in PBS at pH 7.4 containing albumin-free red blood cells at a concentration of $(10\pm1)\times10^6$ cell/μL and provides direct evidence of the extensive interactions of a homosilatecan with red blood cells. Spectra were recorded in front-face cuvettes (to optimize fluorescence versus scatter levels) at 37° C. using a DB-91 concentration of 10 μM and exciting light of 370 nm.

Figure 7:
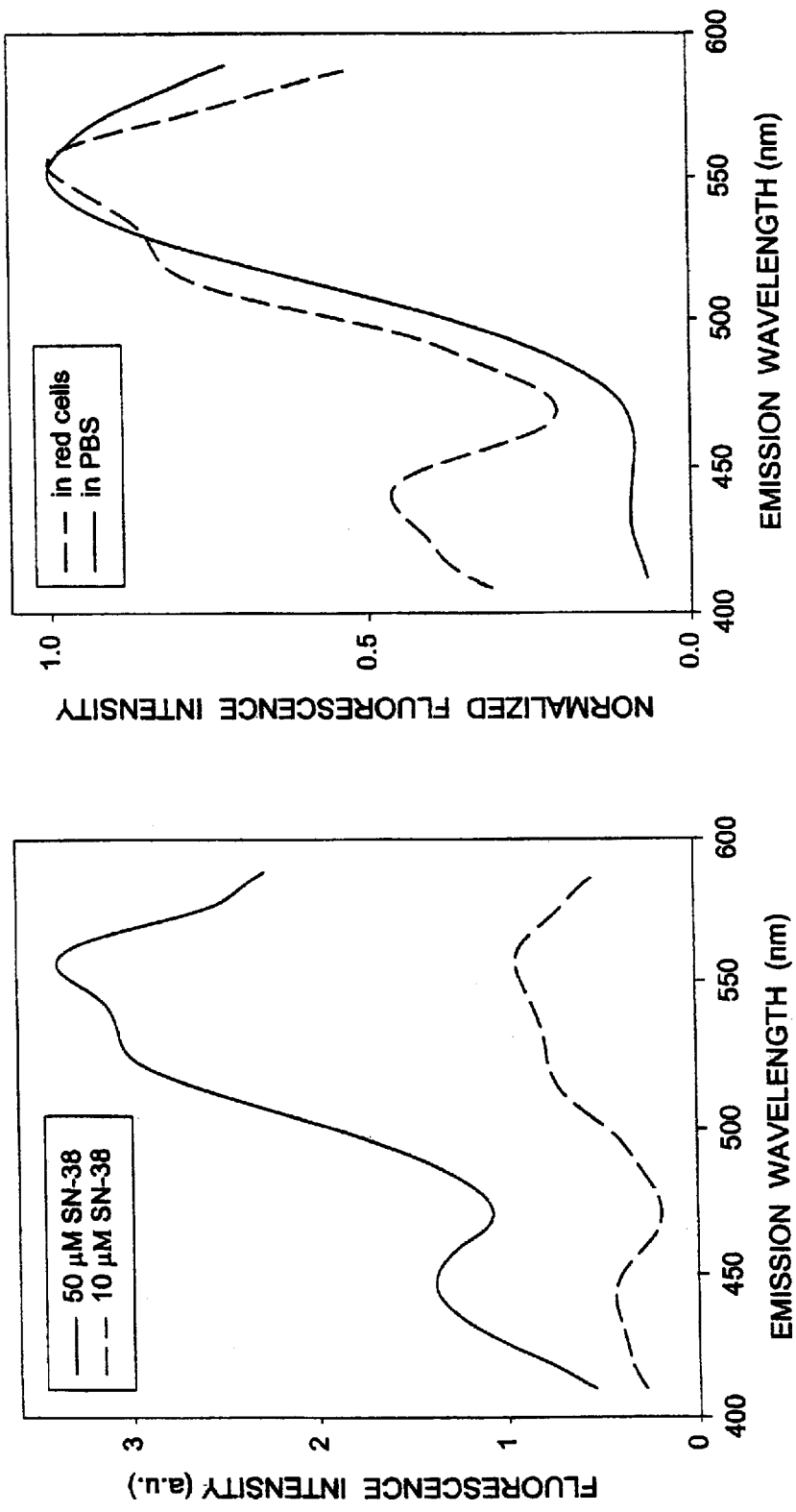
FIG. 7 illustrates the fluorescence emission spectra of prior art compound 7-ethyl-10-hydroxycamptothecin (SN-38) in solutions of phosphate-buffered saline (PBS) at pH 7.4 and in PBS at pH 7.4 containing albumin-free red blood cells at a concentration of (10±1)×10$^6$ cell/μL.
Figure 8:
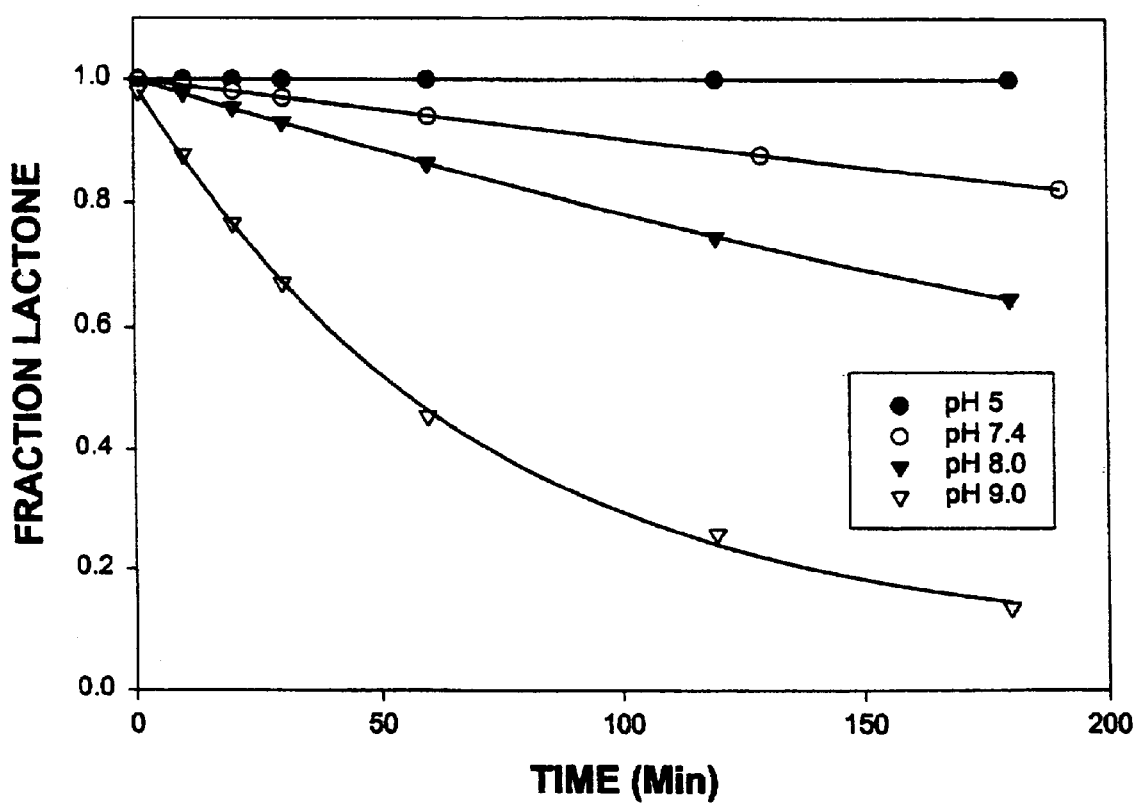
FIG. 8 illustrates the pH dependence of the stability of 1 μM 7-trimethylsilyl-10-aminohomocamptothecin (DB38) in solutions of phosphate-buffered saline (PBS) at pH values of 5.0, 7.4, 8.0, and 9.0 as determined using HPLC methods.
Figure 9:
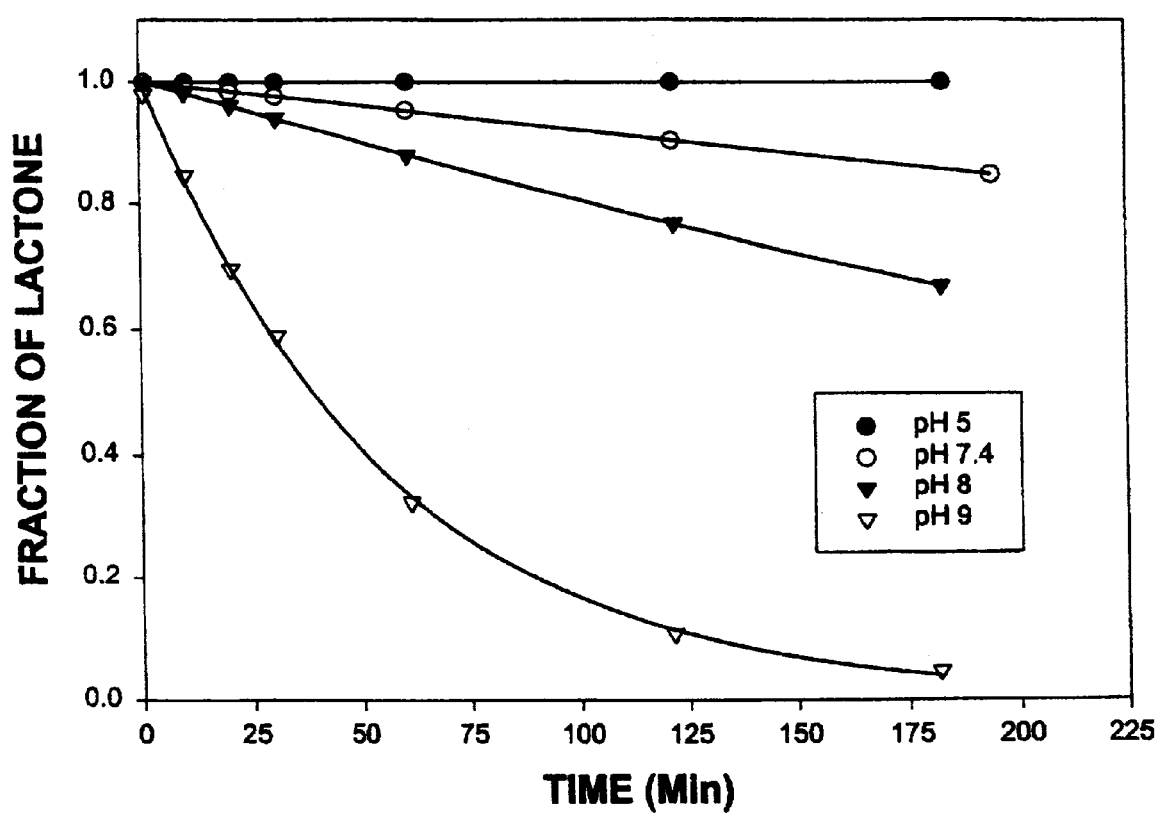
FIG. 9 illustrates the pH dependence of the stability of 1 μM 7-t-butyldimethylsilylhomocamptothecin (DB81) in solutions of phosphate-buffered saline (PBS) at pH values of 5.0, 7.4, 8.0, and 9.0 as determined using HPLC methods.
Figure 10:
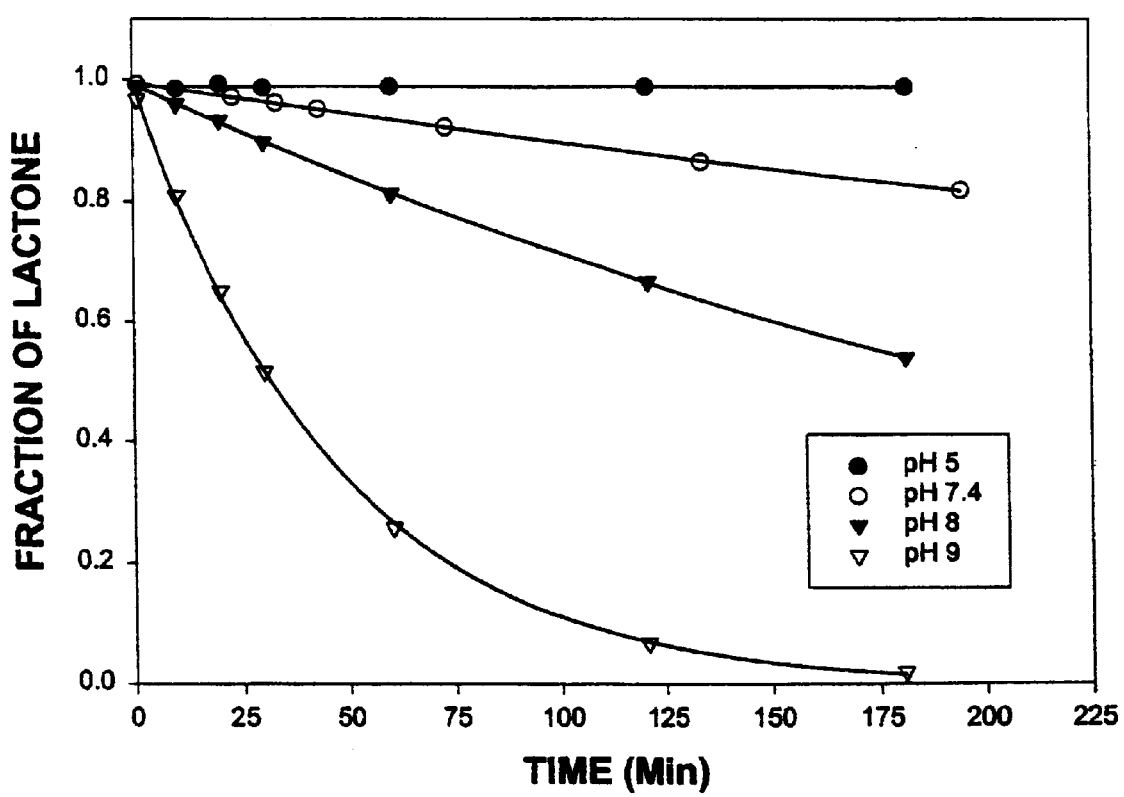
FIG. 10 illustrates the pH dependence of the stability of 1 μM 7-t-butyldimethylsilyl-10-aminohomocamptothecin (DB90) in solutions of phosphate-buffered saline (PBS) at pH values of 5.0, 7.4, 8.0, and 9.0 as determined using HPLC methods.
Figure 11:
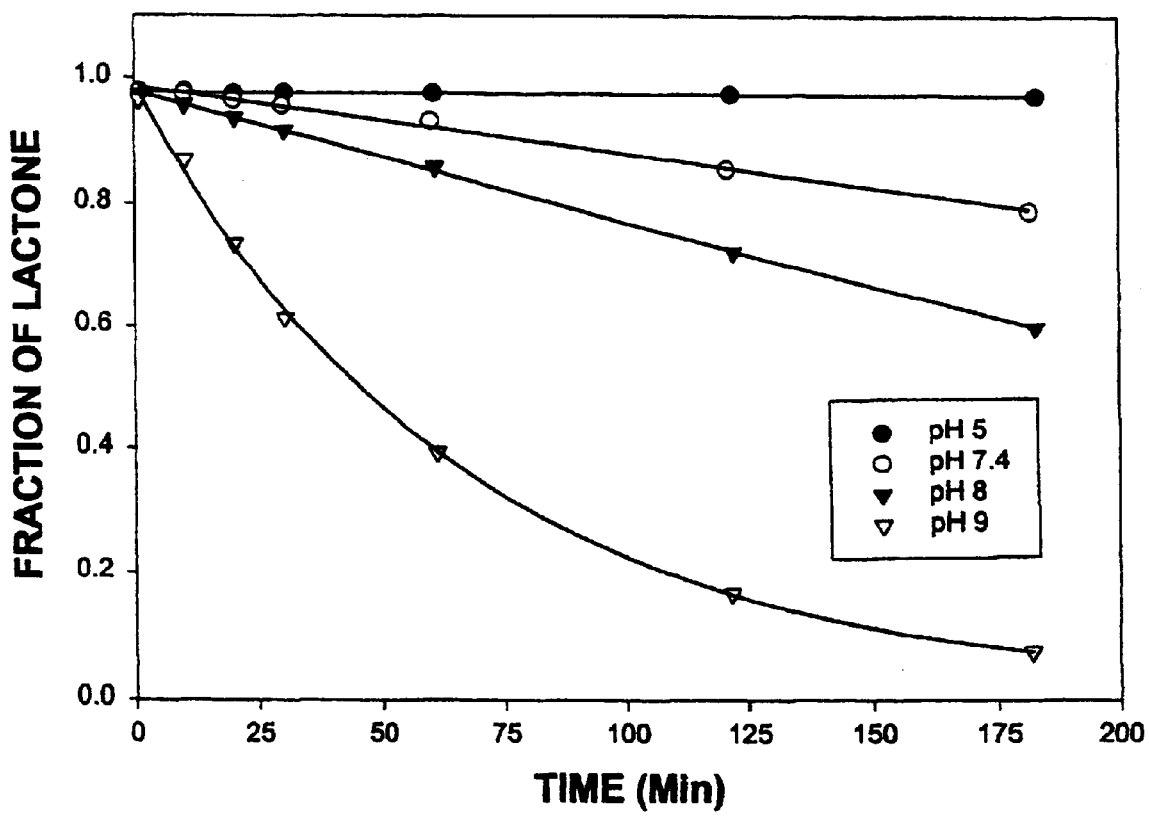
FIG. 11 illustrates the pH dependence of the stability of 1 μM of 7-t-butyldimethylsilyl-10-hydroxyhomocamptothecin (DB91) in solutions of phosphate-buffered saline (PBS) at pH values of 5.0, 7.4, 8.0, and 9.0 as determined using HPLC methods.

The emission maxima for DB-91 in PBS is 554 nm. In the presence of red blood cells, a peak with a significantly lower $\lambda_{max}$ value is observed indicating that the agent is capable of partitioning into the red blood cell membranes. The membranes of the red blood cells provide a hydrophobic microenvironment where the protonated excited-state complexes can form and fluoresce from. Comparison of the emission spectra of DB-91 in the presence of human erythrocytes with that of clinically relevant 7-ethyl-10-hydroxycamptothecin (SN-38), as illustrated in FIG. 7, indicate there is more extensive protonated excited-state complex formation in the case of DB-91. Similar to the studies of FIG. 6, the spectra of FIG. 7 were recorded in front-face cuvettes at 37° C. using an SN-38 concentration of 10 μM and exciting light of 370 nm These findings corroborate model membrane studies indicating the membrane binding of SN-38 is significantly less than the extensive interactions noted for DB-91 (SN-38 displays a $K_{DMPC}$ value of 300 $M^{-1}$ whereas DB-91 displays a $K_{DMPC}$ value of 8,000 $M^{-1}$). From our spectral studies we conclude the novel homosilatcan DB-91 is a more lipophilic, erythrocyte-interactive agent than the FDA-approved SN-38.

Homosilatecans Display Improved Stabilities in Aqueous Solution Relative to Camptothecins Containing α-hydroxyLactone Pharmacophores FIGS. 8 through 11 illustrate the pH dependence of the stability of 1 µM solutions of DB-38, DB-81, DB-90, and DB-91 in solutions of phosphate-buffered saline (PBS) at pH values of 5.0, 7.4, 8.0, and 9.0. The stability parameters for each drug were determined using HPLC methods. All experiments were conducted at 37° C. Hydrolysis is observed at pH values of 7.4, 8.0, and 9.0 with more extensive hydrolysis being noted at the higher pH values.

Although hydrolysis is observed at pH values of 7.4, 8.0, and 9.0, our data indicate that the lactone ring of homosilatecans is less labile (that is, significantly slower in undergoing hydrolysis) relative to both silatecans and camptothecins containing the conventional α-hydroxylactone ring moiety.

Figure 12:
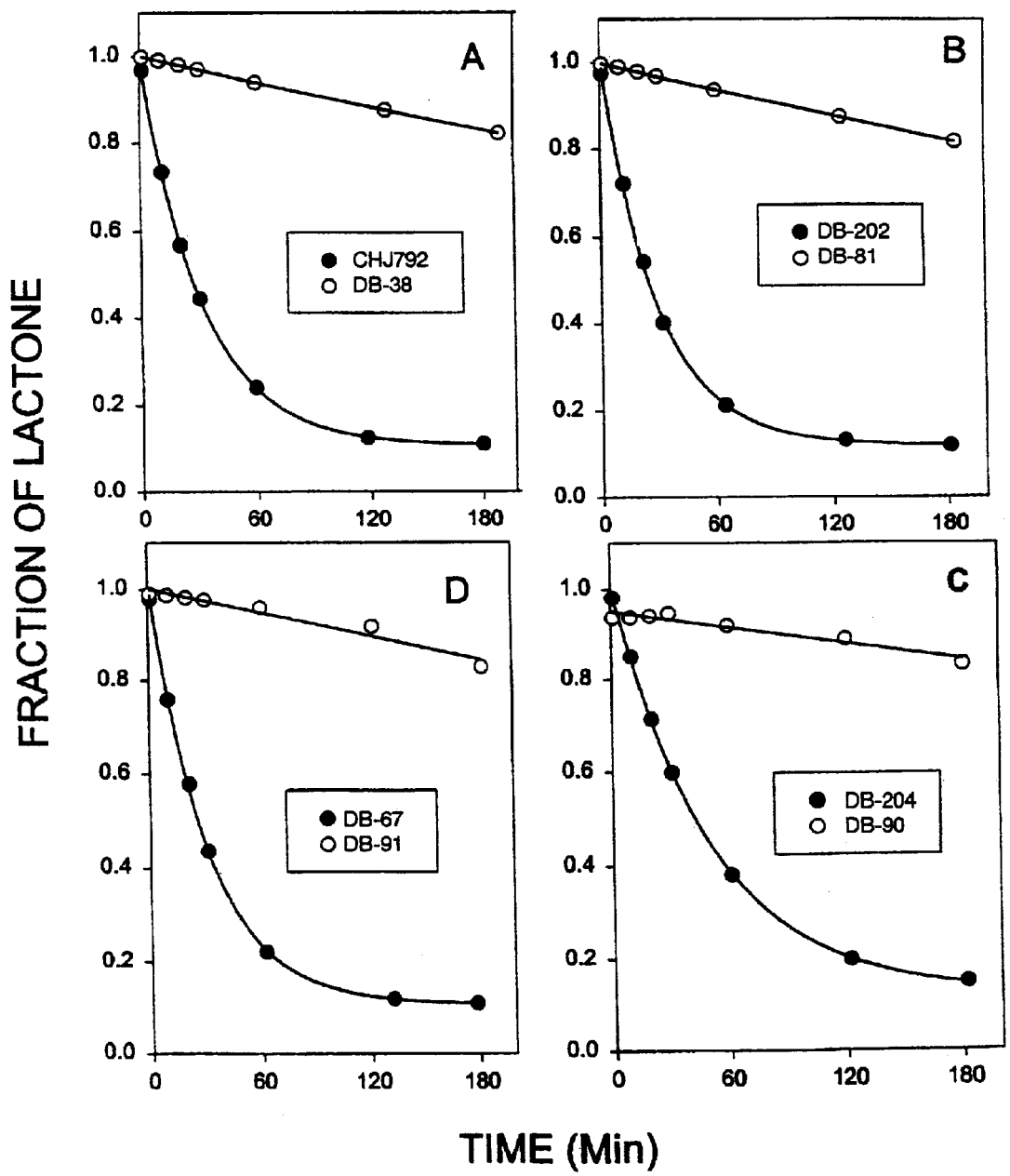
FIG. 12 illustrates the improved stabilities of four novel homosilatecans of the current invention in PBS solution as determined using HPLC methods.

FIG. 12 contrasts the improved stabilities of four novel homosilatecans of the present invention with their corresponding silatecan structure containing the α-hydroxylactone functionality. All the experiments of FIG. 12 were conducted in PBS at 37° C. Panels A through D each contain stability profiles for a novel homosilatecan (open circles) and its corresponding silatecan (solid circles) containing the conventional α-hydroxylactone ring moiety found in camptothecin and other clinically relevant camptothecin analogs such as topotecan, SN-38, CPT-11 and 9-aminocamptothecin.

In all cases, the agents containing the expanded E-ring or homosilatecan structures displayed markedly enhanced stability. The stability parameters for the homosilatecans are summarized in Table 3. The data indicate that the lactone ring of homosilatecans is less labile (that is, significantly slower in undergoing hydrolysis) relative to the α-hydroxylactone ring moiety contained in both silatecans and camptothecins. For silatecans and camptothecins such as topotecan and camptothecin, approximately 12% of lactone remains at equilibrium after 3 hours, whereas greater than 80% lactone remains for each of the homosilatecans under identical incubation conditions.

Figure 13:
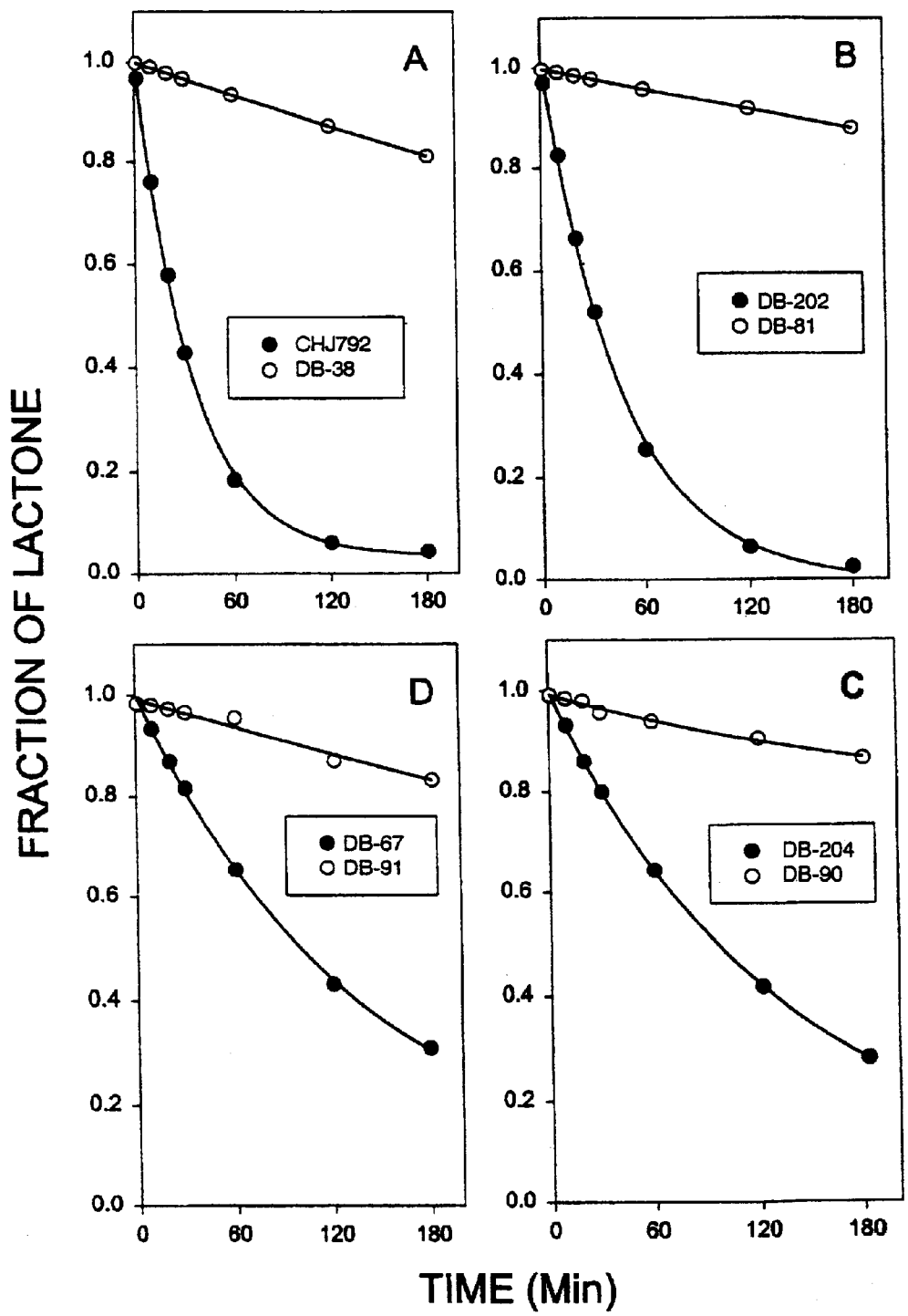
FIG. 13 depicts the improved stabilities of four novel homosilatecans of the current invention in PBS/HSA as determined by HPLC methods.
Figure 14:
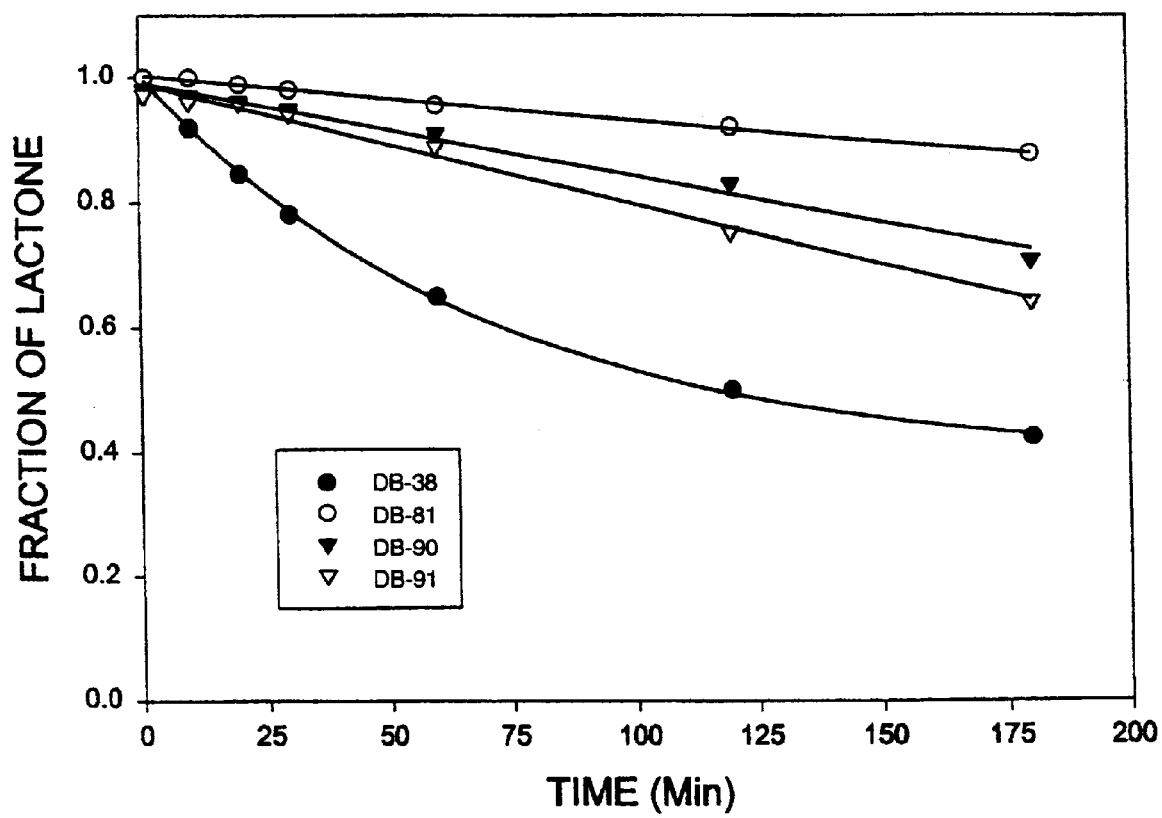
FIG. 14 depicts the human plasma stabilities of four novel homosilatecans of the current invention as determined using HPLC methods.

Determination of the Superior Stabilities of Homosilatecans in the Presence of Human Serum Albumin FIG. 13 depicts the improved stabilities of four novel homosilatecans of the current invention following incubation in PBS containing 30 mg/ml human serum albumin at 37° C. Panels A through D each contain stability profiles for a novel homosilatecan and its corresponding silatecan containing the conventional α-hydroxylactone ring moiety found in camptothecin and other clinically relevant camptothecin analogs such as topotecan, SN-38, CPT-11 and 9-aminocamptothecin. In all cases, the agents containing the expanded E-ring structures displayed markedly enhanced stabilities in the presence of HSA. The stability parameters for the homosilatecans are summarized in Table 3. As illustrated in FIG. 14, the homosilatecans of the current invention also displayed superior stabilities in human plasma than camptothecins such as topotecan, SN-38, and CPT-11. Of the homosilatecans, DB-81 displayed the highest stability in human plasma, followed by DB-90 and DB-91, with DB-38 (the least lipophilic of the homosilatecans studied) displaying the lowest stability in human plasma. All the experiments of FIG. 14 were conducted in human plasma at 37° C. Plasma samples were continuously aerated by a stream of blood gas resulting in the maintenance of pH at values of 7.5±0.1. In all cases, the agents containing the expanded E-ring or homosilatecan structures displayed markedly enhanced stabilities relative to the parent drug camptothecin containing the conventional α-hydroxylactone ring moiety. The stability parameters for the homosilatecans are summarized in Table 3.

Our studies demonstrate that both lipophilic as well as more water-soluble homosilatecans display improved stabilities over homocamptothecin that contains no substitutions in the A and B rings. See Lavergne et al. "Homocamptothecins: Synthesis and Antitumor Activity of Novel E-Ring-Modified Camptothecin Analogues" J. Med. Chem. 41: 5410–5419 (1998). Thus, the present invention indicates that substitution of the A and B ring of homocamptothecin is a favorable factor with respect to blood stabilities. The likely explanation is that the unsubstituted homocamptothecin carboxylate, like camptothecin carboxylate, binds HSA preferentially in the carboxylate form and effectively shifts the lactone-carboxylate equilibria to the right.

Our results indicate that dramatically improved human plasma stability can be realized by combining the β-hydroxylactone pharmacophore with the following concomitant structural changes: 1) B-ring modification such as a silyl or an silylalkyl functionality at position 7 (e.g. DB-81); 2) A-ring modification such as the structural modifications contained in topotecan (water-solublizing changes such as inclusion of 9-dimethylaminomethyl and 10-hydroxy functionalities disfavor carboxylate binding to HSA; and 3) combined substitution in both the A and the B ring that includes, for example, a silyl or silylalkyl substituent at position 7 (e.g. DB-90 and DB-91). See also Mi, Z., Malak, H., and Burke, T. G., "Reduced Albumin Binding Promotes the Stability and Activity of Topotecan in Human Blood," Biochemistry, 34, 13722–13728 (1995). The compounds of the latter example display high lipophilicities and reduced specific interactions between the carboxylate drug form and HSA, both factors contributing to improved plasma stability.

Markedly Enhanced Stabilities of the Novel Homosilatecans in Human Blood

Figure 15:
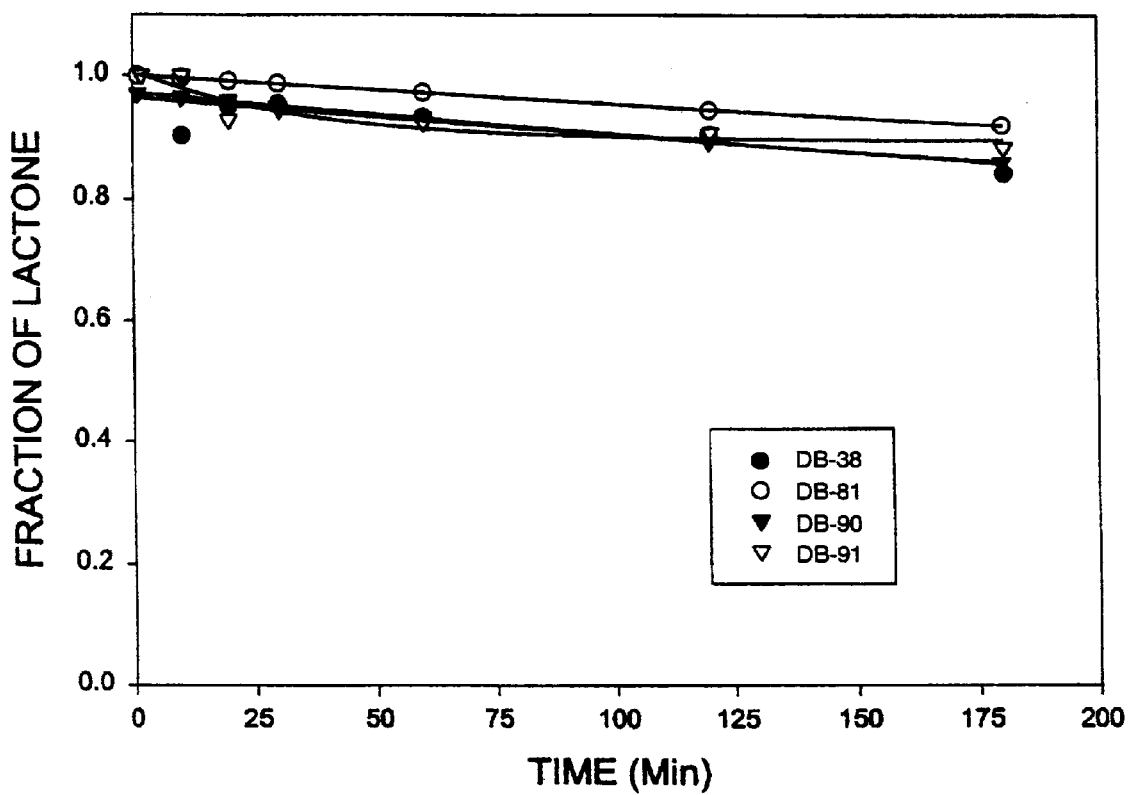
FIG. 15 depicts the stabilities of four novel homosilatecans of the current invention in PBS suspensions containing physiologically-relevant concentrations [(5±1)×10$^6$ cell/μL] of albumin-free red blood cells.

FIG. 15 depicts the stabilities of four novel homosilatecans of the current invention in PBS suspensions containing physiologically-relevant concentrations [$(5\pm1)\times10^6$ cell/µL] of albumin-free red blood cells. Stability characteristics were determined at 37° C. using HPLC methods. In all cases, the agents containing the expanded E-ring or homosilatecan structures displayed markedly enhanced stabilities in the presence of red blood cells relative to published literature values for camptothecin analogs containing the conventional α-hydroxylactone ring moiety (such as the clinically relevant agents SN-38, 9-aminocamptothecin, 9-nitrocamptothecin, GI-147211C, topotecan, etc. The stability parameters for the homosilatecans are summarized in Table 3.

Figure 16:
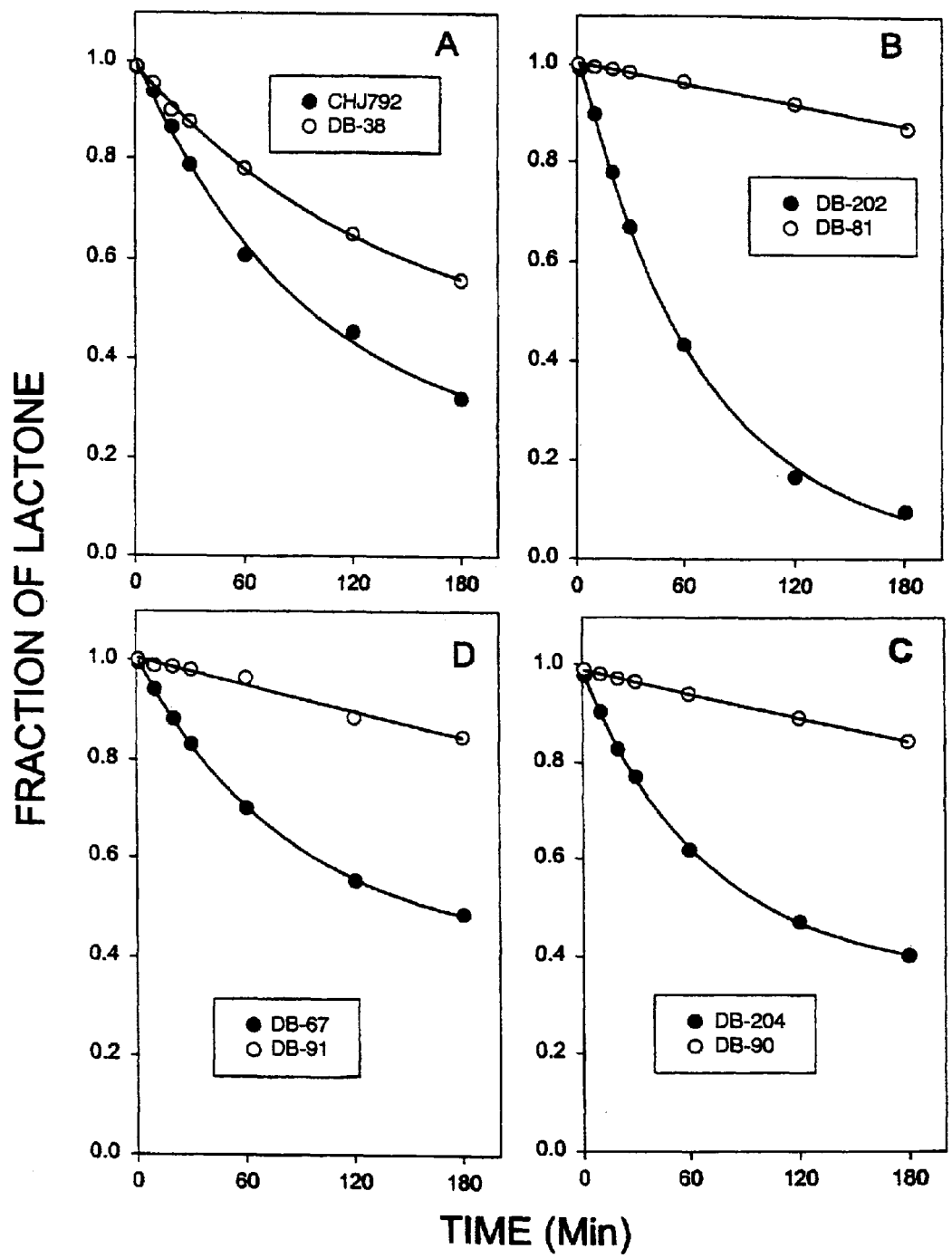
FIG. 16 illustrates the improved human blood stabilities of four novel homosilatecans of the current invention as determined using HPLC methods.
Figure 17:
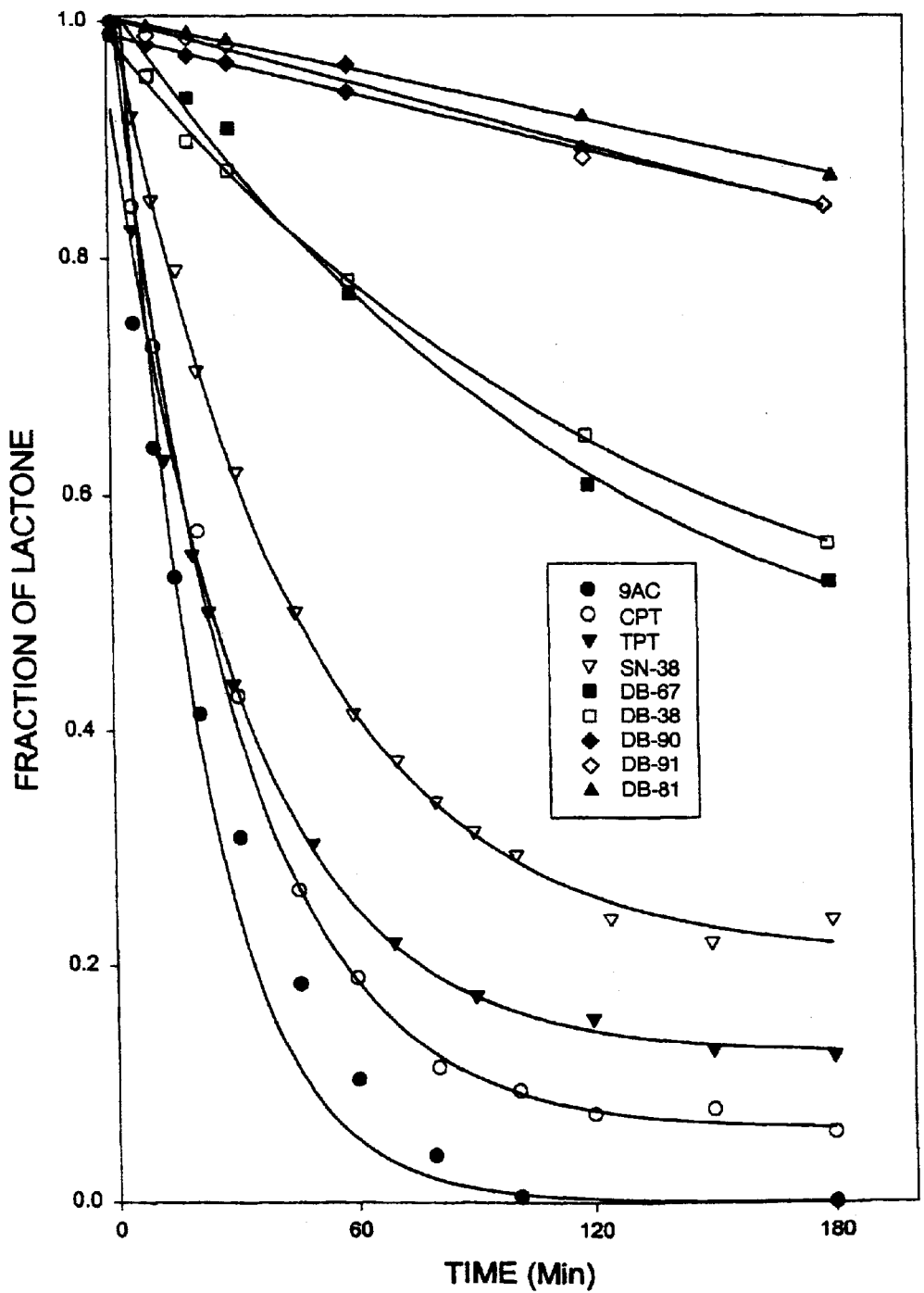
FIG. 17 illustrates the improved human blood stabilities of four novel homosilatecans of this invention relative to clinically-relevant agents of the prior art which include 9-aminocamptothecin (9AC), camptothecin (CPT), topotecan (TPT) and SN-38.

FIG. 16 and FIG. 17 depict the improved human blood stabilities of four novel homosilatecans of the present invention. All experiments were conducted at pH 7.4 and 37° C. In FIG. 16, panels A through D each contain stability profiles for a novel homosilatecan (open circles) and its corresponding silatecan (solid circles) containing the conventional α-hydroxylactone ring moiety found in camptothecin and other clinically relevant and camptothecin analogs such as topotecan, SN-38, CPT-11 and 9-aminocamptothecin and experimental agents as well. In all cases, the agents containing the expanded E-ring or homosilatecan structures displayed markedly enhanced human blood stabilities relative to camptothecin analogs such as topotecan and SN-38. FIG. 17 illustrates the improved human blood stabilities of the novel homosilatecans of the present invention compared to current clinically-relevant agents including 9-aminocamptothecin (9AC), camptothecin (CPT), topotecan (TPT) and SN-38 (SN38). The stability parameters of FIGS. 16 and 17 are summarized in Table 3.

The human blood stability values noted for DB-81, DB-90 and DB-91 are the highest yet to be measured for a intrinsically potent camptothecin analog. The greater than 80% lactone values following 3 hrs. of incubation compare very favorably relative to the corresponding percent lactone levels in whole human blood for 9-aminocamptothecin (approx. 0.3%), camptothecin (approx. 6%) topotecan (approx. 15%), CPT-11 (approx. 21.0%), and SN-38 (approx. 30%).

TABLE 3

Summary of Human Blood Stability Parameters for Homosilatecans

| DRUG NAME and FLUID | Incubation Time (Hours) | % Lactone |
|---|---|---|
| DB-38 | | |
| Whole Blood | 3 | 56.4 ± 0.6 |
| HSA | 3 | 81.4 ± 0.3 |
|  | 24 | 34.1 ± 2.2 |
| PBS | 3 | 82.8 ± 0.7 |
|  | 24 | 26.8 ± 2.3 |
| Plasma | 3 | 40.3 ± 2.1 |
| RBC | 3 | 84.8 ± 1.5 |
|  | 24 | 39.4 ± 1.2 |
| DB-81 | | |
| Whole Blood | 3 | 86.6 ± 0.5 |
|  | 24 | 27.0 ± 2.3 |
| HSA | 3 | 88.1 ± 0.2 |
|  | 24 | 42.5 ± 1.6 |
| PBS | 3 | 84.9 ± 0.3 |
|  | 24 | 30.9 ± 2.0 |
| Plasma | 3 | 85.0 ± 4.3 |
| RBC | 3 | 92.0 ± 0.0 |
|  | 24 | 55.8 ± 1.7 |
| DB-90 | | |
| Whole Blood | 3 | 85.2 ± 0.7 |
|  | 24 | 24.6 ± 1.3 |
| HSA | 3 | 86.8 ± 0.2 |
|  | 24 | 42.0 ± 2.7 |
| PBS | 3 | 83.7 ± 0.5 |
|  | 24 | 26.1 ± 1.0 |
| Plasma | 3 | 71.1 ± 3.5 |
| RBC | 3 | 85.5 ± 0.4 |
|  | 24 | 38.5 ± 1.4 |
| DB-91 | | |
| Whole Blood | 3 | 84.9 ± 0.3 |
|  | 24 | 37.1 ± 1.8 |
| HSA | 3 | 82.9 ± 0.3 |
|  | 24 | 33.2 ± 3.0 |
| PBS | 3 | 83.1 ± 0.3 |
|  | 24 | 32.2 ± 1.0 |
| Plasma | 3 | 61.5 ± 3.9 |
| RBC | 3 | 88.5 ± 0.2 |
|  | 24 | 42.6 ± 2.6 |

The Novel Homosilatecans of the Current Invention Overcome the Marked Interspecies Variations With Respect to Blood Stabilities that Have Been Observed in the Past for Clinically Relevant Camptothecins Such as 9-Aminocamptothecin, 9-Nitrocamptothecin and Camptothecin Camptothecin and 9-aminocamptothecin, anticancer agents renown for their novel mechanism of action and outstanding murine in vivo activity, have to date displayed only modest therapeutic utility against human cancers. The drugs contain the lactone ring moiety which, at pH 7.4, hydrolyzes to yield biologically-inactive carboxylate forms. Comparison of drug stabilities for 9-aminocamptothecin reveals that ring opening occurred to a much greater extent in human blood than mouse blood (see Table 4). Camptothecin has been shown previously to behave in a similar manner. Burke, T. G. Munshi, C. B., Mi, Z., and Jiang, Y., "The Important Role of Albumin in Determining the Relative Human Blood Stabilities of the Camptothecin Anticancer Drugs," *J. Pharma. Sci.* 84, 518–519 (1995); and Mi, Z. and Burke, T. G., "Marked Interspecies Variations Concerning the Interactions of Camptothecin with Serum Albumins: A Frequency-Domain Fluorescence Spectroscopic Study," *Biochemistry* 33, 12540–12545 (1994). We have used the technique of multifrequency phase-modulation spectroscopic analyses of the intrinsic fluorescence emissions of camptothecin lactone and carboxylate to provide a physical explanation for the extensive ring opening observed for camptothecin and 9-aminocamptothecin in the presence of human serum albumin (HSA). HSA exhibits a marked 200-fold binding preference for the carboxylate ($K=1.2 \times 10^6$ $M^{-1}$) relative to the lactone ($K \approx 5.5 \times 10^3$ $M^{-1}$). Serum albumins from other species were found to bind camptothecin carboxylate not nearly as tightly as HSA. Due to the unique capacity of human albumin to bind camptothecin carboxylate and 9-aminocamptothecin carboxylate resulting in extensive conversion of the drug to its biologically inactive form, it appears that the success of these agents in eradicating cancer in animal models may be inherently more difficult to duplicate in humans.

The data for the novel homosilatecans of the current invention show essentially only minor variations between lactone levels in mouse blood versus human blood. The noted changes in mouse versus animal blood are very small relative to the 100-fold difference in lactone levels observed for 9-aminocamptothecin. In mouse blood experiments for DB-81 and DB-91, the lactone levels actually observed in human blood are modestly underestimated by values of 6% and 20%, respectively. However, for 9-aminocamptothecin mouse blood overestimates by 100-fold the lactone levels actually observed in human blood. These results indicate that there are fundamental physiological reasons to think that the success of our novel homosilatecans in animal models can be more readily translated into humans relative to agents such as camptothecin and 9-aminocamptothecin.

TABLE 4

Comparison of the Marked Interspecies Variations in Blood Stabilities For Camptothecin and 9-Aminocamptothecin Versus the Relatively Minor Differences Observed for Novel, Highly Lipophilic Camptothecin Analogs.[a]

| Compound | Percent Lactone in Mouse Blood after 3 Hours of Incubation | Percent Lactone in Human Blood after 3 Hours of Incubation | Ratio of Lactone Level Mouse/Human |
|---|---|---|---|
| 9-Aminocamptothecin | 38 | 0.4 | 100 |
| Camptothecin | 20 | 7 | 3 |
| DB-38 | 72 | 56 | 1.3 |
| DB-81 | 80 | 87 | 0.9 |
| DB-90 | 61 | 85 | 0.7 |
| DB-91 | 70 | 85 | 0.8 |

[a]Experiments were conducted at pH 7.4 and 37° C. and lactone levels determined using HPLC methods. Blood samples were drawn and kept at 5° C. prior to the initiation of an experiment.

Highly Lipophilic Camptothecins Display High Anticancer Potency Even in the Presence Human Serum Albumin The cytotoxicities of various camptothecins against MDA-MB-435 tumorigenic metastatic human breast cancer cells are summarized in Table 5. The cytotoxicity values are for 72 hr. exposure times. Overall, we found DB-38 to be the most potent of the four novel homosilatecans which we studied, with an $IC_{50}$ value of 20 nM, while the $IC_{50}$ values for the other homosilatecans ranged from 20 nM to 115 nM. Our results clearly indicate that through novel homosilatecan development the stability of the agents in human and animal blood can be markedly improved and equilized without compromising the high intrinsic potency and cytotoxicity of this important class of anticancer drugs.

TABLE 5

$IC_{50}$ Values of Homosilatecans and Camptothecin Analogs Against MDA-MB-435 Tumorogenic Metastatic Human Breast Cancer Cells in the Absence and Presence of Human Serum Albumin.

| Compound | $IC_{50}$ (nM) (w/o HSA) |
| --- | --- |
| Camptothecin | 12 ± 4 |
| DB-38 | 20 ± 3 |
| DB-81 | 77 ± 13 |
| DB-90 | 73 ± 8 |
| DB-91 | 115 ± 5 |

EXAMPLES

Experimental Methods for the Qualitative and Quantitative Determination of Lipid Bilayer Partitioning (i.e. Lipophilicity) and Lactone Ring Stability of the Novel Homosilatecans of the Current Invention Chemicals Camptothecin and topotecan were in their 20(S)-configuration and were of high purity (>98%) as determined by HPLC assays with fluorescence detection. The preparation of the homosilatecans is described elsewhere in this application. All other agents were reagent grade and were used without further purification. High purity water was provided by a Milli-Q UV PLUS purification system (Bedford, Mass.) was utilized in all experiments.

Drug Stock Solution Preparation

Stock solutions of the drugs were prepared in dimethylsulfoxide (A.C.S. spectrophotometric grade, Aldrich, Milwaukee, Wis.) at a concentration of $2 \times 10^{-3}$ M and stored in the dark at 4° C. L-α-Dimyristoylphosphatidylcholine (DMPC) and L-α-dimyristoylphosphatidylglycerol (DMPG) were obtained from Avanti Polar Lipids, Alabaster, Ala., and were used without further purification. All other chemicals were reagent grade and were used without further purification.

Vesicle Preparation

Small unilamellar vesicle (SUV) suspensions were prepared the day of an experiment by a methodology reported previously Burke and Tritton, Biochemistry 24 5972–5980 (1985); and Burke, T. G., Mishra, A. K., Wani, M. C. and Wall, M. E. "Lipid bilayer partitioning and stability of camptothecin drugs," *Biochemistry.* 32: 5352–5364 (1993), the disclosures of which are incorporated herein by reference. Briefly, stock lipid suspensions containing known amount of lipid (200 mg/mL lipid or less) in phosphate buffered saline (PBS, pH 7.4) were prepared by Vortex mixing for 5–10 min above the $T_M$ of the lipid. The lipid dispersions were then sonicated using a bath-type sonicator (Laboratory Supplies Co., Hicksville, N.Y.) for 3–4 h until they became optically clear. A decrease in pH from 7.4 to 6.8 was observed for the SUV preparations of DMPG; therefore, the pH of these SUV suspensions was adjusted to 7.4 using small quantities of 2.5 M NaOH in PBS, followed by additional sonication. Each type of vesicle suspension was annealed for 30 min at 37° C. and then used in an experiment.

Fluorescence Instrumentation

Steady-state fluorescence measurements were obtained on a SLM Model 9850 spectrofluorometer with a thermostated cuvette compartment. This instrument was interfaced with an IBM PS/2 model 55 SX computer. Excitation and emission spectra were recorded with an excitation resolution of 8 nm and an emission resolution of 4 nm. In all cases spectra were corrected for background fluorescence and scatter from unlabeled lipids or from solvents by subtraction of the spectrum of a blank. Steady-state fluorescence intensity measurements were made in the absence of polarizers. Steady-state anisotropy (a) measurements were determined with the instrument in the "T-format" for simultaneous measurement of two polarized intensities. The alignment of polarizers was checked routinely using a dilute suspension of 0.25 μm polystyrene microspheres (Polysciences, Inc, Warrington, Pa.) in water and anisotropy values of >0.99 were obtained. Alternatively, polarizer orientation was checked using a dilute solution of glycogen in water. The anisotropy was calculated from $$a = (I_{VV} - GI_{VH})/(I_{VV} + GI_{VH}),$$

where $G = I_{VH}/I_{HH}$ and the subscripts refer to vertical and horizontal orientations of the excitation and emission polarizers, respectively.

Anisotropy measurements for homosilatecans and camptothecins were conducted using exciting light of 370 to 400 nm and long pass filters on each emission channel to isolate the drug's fluorescence signal from background scatter and/or residual fluorescence. All emission filters were obtained from Oriel Corp (Stamford, Conn.). The combination of exciting light and emission filters allowed adequate separation of fluorescence from background signal. The contribution of background fluorescence, together with scattered light, was typically less than 1% of the total intensity. Since the lactone rings of camptothecin and related congeners undergo hydrolysis in aqueous medium with half-lives of approximately 20 min., all measurements were completed within the shortest possible time (ca. 0.5 to 1 min) after mixing the drug stock solution with thermally pre-equilibrated solutions such that the experiments were free of hydrolysis product. In fluorescence spectroscopic experiments designed to provide information concerning the interactions of homosilatecans and camptothecins with red blood cells, drug concentrations of 10 μM were used. Experiments with red blood cells were carried out in front-face quartz cuvettes to optimize fluorescence signal and minimize scattered light.

Determination of Equilibrium Binding Constants

The method of fluorescence anisotropy titration as reported by Burke, T. C., Mishra, A. K., Wani, M. C. and Wall, M. E. "Lipid bilayer partitioning and stability of camptothecin drugs," *Biochemistry.* 32: 5352–5364 (1993), the disclosure of which is incorporated herein by reference, was employed to determine the concentrations of free and bound species of drug in liposome suspensions containing a total drug concentration of $1 \times 10^{-6}$ M and varying lipid concentrations. All experiments were conducted in glass tubes. The overall association constants are defined as $$K = [A_B]/[A_F][L]$$

where $[A_B]$ represents the concentration of bound drug, $[A_F]$ represents the concentration of free drug, and $[L]$ represents the total lipid concentration of the sample. Double-reciprocal plots of the binding isotherms {1/(bound fraction of drug) vs. 1/[lipid]} were linear and K values were determined from their slopes by the method of linear least squares analysis. A computer program based on the K=[$A_B$]/[$A_F$][L] relationship was written to predict bound drug levels for specified values of K and total drug.

Kinetics of Lactone Ring Opening of Homosilatecans, Silatecans, and Camptothecins The hydrolysis kinetics of camptothecins in the presence of different blood components were determined by a quantitative C18 reversed-phase high-performance liquid chromatography (HPLC) assay modified from methodologies described previously in the literature cited above. The preparation of whole blood and fractionated blood samples was carried out as described previously. Crystallized HSA of high purity (>97%) from Sigma Chemical (St. Louis, Mo.) was used. HSA stock solutions were prepared in PBS buffer with a final pH of 7.40±0.05. HSA concentrations were determined by UV absorbance at 278 nm using an extinction coefficient of 39,800 $M^{-1}cm^{-1}$ (Porter, 1992). All other agents were reagent grade and were used without further purification. High purity water provided by a Milli-Q UV PLUS purification system (Bedford, Mass.) was utilized in all experiments. HPLC solvents were from Fisher Scientific. Human plasma and red blood cells were obtained from Central Kentucky Blood Center. Whole blood was obtained from a male donor in heparinized tubes, stored at 5–10° C. and used as soon as possible (typically within 1 week). Blood from mice was collected in heparinized tubes and stored at 5–10° C. until use.

HPLC assays were performed either on a Waters Alliance 2690 HPLC system equipped with a temperature-controlled autosampler and Waters 474 scanning fluorescence detector. A second HPLC system was composed of a Waters HPLC system composed of 501 HPLC pumps, 717 Plus temperature-controlled autosampler and 470 scanning fluorescence detector. The HPLC assay procedures used for the homosilatecans are summarized below. Solvent A consisted of acetonitrile and Solvent B was 2% triethylammonium acetate, pH 5.5, with a flow rate of 1 ml/min. For DB-38 an isocratic elution was used: 33% Solvent A; 67% Solvent B; $\lambda_{ex}$:345 nm and $\lambda_{em}$:518 nm. For DB-81 an isocratic elution was used: 56% Solvent A; 44% Solvent B; and $\lambda_{ex}$:375 nm and $\lambda_{em}$:444 nm. For DB-90 an isocratic elution was used: 41% Solvent A; 59% Solvent B; $\lambda_{ex}$:412 nm and $\lambda_{em}$:526 nm. For DB-91 an isocratic elution of 42% Solvent A, 58% Solvent B, and $\lambda_{ex}$:392 nm and $\lambda_{em}$:562 nm.

To determine the stabilities of homosilatecans in PBS, an aliquot of each of the homosilatecans in DMSO was added to phosphate buffered saline (PBS), pH 7.4 in a HPLC autosampler vial maintained at 37° C. in a water bath to result in final drug concentration of 1 μM. The drug-containing vial was quickly transferred to the autosampler maintained at 37° C. and aliquots analyzed at various time points. All the determinations were done in triplicate. The data was collected and analyzed using Waters Millenium software. The fraction of lactone was calculated using the peak area of lactone and carboxylate peak and using the lactone/carboxylate ratio.

To determine drug stability in whole blood, whole blood was incubated at 37° C. for 30 min and pH determined. Blood pH was adjusted to 7.4+/−0.5 using either 0.1 M KOH or 0.1 M HCl. Blood samples were incubated at 37° C. for 30 min and pH remeasured to ensure that it is within the range before an individual assay was started. Aliquots of blood (2 ml each) were removed and placed in three disposable glass test tubes and the tubes were incubated at 37° C. An aliquot of drug in DMSO was then added to the blood to result in a final drug concentration of 1 μM. Incubation at 37° C. was continued and 150 μl aliquots were removed at different time points and added to 600 μl of cold methanol (−20° C.) in an eppendorf tube. The tube was then vortexed for 10 sec and centrifuged in a table top microcentrifuge at 8000 rpm for 45 sec. The Supernatant was removed and placed in an autosampler vial and the vial quickly added to the autosampler maintained at 4° C. The sample was analyzed immediately on the HPLC set-up. The data analysis was as described for the drug in PBS only samples.

To study the stabilities of homosilatecans in PBS containing human serum albumin (HSA), the HSA was dissolved in PBS, pH 7.4 at the concentration of 30 mg/ml and incubated at 37° C. The pH was measured and adjusted to 7.4+/−0.5 using 0.1 M KOH or 0.1 M HCl. Incubation continued until pH stabilized within the target range. An aliquot of PBS/HSA was removed and placed in an autosampler vial and maintained at 37° C. for 10 min. An aliquot of the drug in DMSO was added to the sample resulting in a final drug concentration of 1 μM. The vial was quickly added to the HPLC autosampler maintained at 37° C. and aliquots were injected and analyzed by HPLC at different time points. The data analysis was as described above for the drug in PBS only samples.

To characterize the stabilities of the novel silatecans of interest in human plasma, frozen plasma was incubated at 37° C. in order to thaw. Blood gas was bubbled through the plasma to adjust the pH close to 7.5. Aliquots of plasma (5 ml) were incubated at 37° C. in disposable glass test tubes and drug DMSO stock solutions added to result in a final drug concentration of 1 μM. The samples were then allowed to incubate further at 37° C. Aliquots (150 μl) were removed at different time points and added to 600 μl of cold methanol (−20° C.) in an eppendorf tube. Tubes were vortexed for 10 sec and centrifuged in a tabletop microcentrifuge at 8000 rpm for 45 sec. The supernatant was removed and placed in an autosampler vial and the vial was quickly added to the autosampler maintained at 4° C. The sample was analyzed by HPLC as soon as possible. The data analysis was as described for drug in PBS only samples as described above. Blood gas was continuously bubbled through the plasma samples to pH at 7.5+/−1.0.

To study the stabilities of the novel homosilatecans in the presence of physiologically relevant concentrations of red blood cells (RBC), the following experiments were performed. Packed Red blood cells obtained from the Central Kentucky Red Cross and were counted using a Coulter Cell Counter. The number of cells was adjusted to $5 \times 10^{12}$ Cells/L using PBS, pH 7.4 and incubated at 37° C. for 30 min. The pH of the samples was measured and adjusted to 7.4+/−0.5 using either 0.1 M KOH or 0.1 M HCl. RBCs were incubated at 37° C. for 30 min and the pH remeasured to ensure that it was within the same range as before the assays were started. Aliquot of RBCs (2 ml each) were removed and placed in three disposable glass test tubes and the tubes were incubated at 37° C. Aliquots of drug in DMSO were added to RBC suspensions in PBS to result in final drug concentration of 1 μM. Incubation at 37° C. was continued and 150 μl aliquots were removed at different time points and added to 600 μl of cold methanol (−20° C.) present in an eppendorf tube. The tubes were vortexed for 10 sec and centrifuged in a table top microcentrifuge at 8000 rpm for 45 sec. The supernatant was removed and placed in an autosampler vial and the vial was quickly added to the autosampler maintained at 4° C. The sample was analyzed on HPLC as soon as possible. The data analysis was as described for the drug in PBS only samples described above.

Fluorescence Spectral Changes Upon Homosilatecan Interactions With Lipid Bilayer Membranes Fluorescence emission data were recorded for homosilatecans in solutions of phosphate-buffered saline (PBS) at pH 7.4 and ethanol. Data were also acquired for the new agents in the presence of suspensions of small unilamellar vesicles (SUVs) composed of either electroneutral dimyristoylphosphatidylcholine (DMPC) in PBS or negatively-charged dimyristoylphosphatidylglycerol (DMPG) in PBS. Lipid concentrations of 5 mM were used. For DB-38 all spectra were recorded using exciting light of 410 nm at 37° C. The emission maxima for DB-38 in PBS is 531 nm and this value shifts to lower values in the presence of membranes ($\lambda_{max}$ of 515 nm in the presence of DMPC vesicles and $\lambda_{max}$ of 517 nm in the presence of DMPG vesicles). The spectral shifts of DB-38 which occur in the presence of membranes indicate that the agent is capable of binding both electroneutral and negatively-charged membranes. Spectral recordings were initiated and completed shortly after the addition of the lactone form of the agent to solution or suspension, thereby assuring that the detected signal originates predominantly from the lactone form of the agent (and not the ring-opened form).

Fluorescence emission spectra of 1 μM 7-t-butyldimethylsilylhomocamptothecin (DB-81) were also examined. Lipid concentrations of 10 mM were used. All spectra were recorded using exciting light of 380 nm at 37° C. The emission maxima for DB-81 in PBS buffer is 452 nm and this value shifts to lower values in the presence of membranes ($\lambda_{max}$ of 443 nm in the presence of DMPC vesicles and $\lambda_{max}$ of 442 nm in the presence of DMPG vesicles). The spectral shifts of DB-81 which occur in the presence of membranes indicate that the agent is capable of binding both electroneutral and negatively-charged membranes.

The fluorescence emission spectra of 1 μM 7-t-butyldimethylsilyl-10-aminohomocamptothecin (DB-90) was also examined. All spectra were recorded using exciting light of 430 nm at 37° C. The emission maxima for DB-90 in PBS is 535 nm and this value shifts to lower values in the presence of membranes ($\lambda_{max}$ of 513 nm in the presence of DMPC vesicles and $\lambda_{max}$ of 512 nm in the presence of DMPG vesicles).

The fluorescence emission spectra of 1 μM 7-t-butyldimethylsilyl-10-hydroxy-homocamptothecin (DB-91) was also studied. Lipid concentrations of 10 mM were used. All spectra were recorded using exciting light of 394 nm at 37° C. The emission maxima for DB-91 in PBS is 554 nm and this value shifts to lower values in the presence of membranes ($\lambda_{max}$ of 441 nm in the presence of DMPC vesicles and $\lambda_{max}$ of 434 nm in the presence of DMPG vesicles.

The fluorescence emission spectra of 1 μM of the carboxylate form of 7-t-butyl-dimethylsilyl-10-aminohomocamptothecin (DB90 carboxylate) was also studied. Lipid concentrations of 0.15 mM were used. The concentration of lipid used in these experiments was greater than in the experiments conducted using the corresponding lactone form of DB-90; the higher lipid concentrations were used because of the reduced membrane associations of the opened-ring form of the drug relative to the closed-ring lactone form of the drug. All spectra were recorded using exciting light of 430 nm at 37° C. The emission maxima for DB-90 carboxylate in PBS is 529 nm and this value shifts to lower values in the presence of membranes ($\lambda_{max}$ of 512 nm in the presence of DMPC vesicles and $\lambda_{max}$ of 512 nm in the presence of DMPG vesicles.

The fluorescence emission spectra of 1 μM of the ring-opened or carboxylate form of 7-t-butyldimethylsilyl-10-hydroxyhomocamptothecin (DB-91 carboxylate) were also acquired. Lipid concentrations of 0.15 M were used (the higher concentration of lipid required in these experiments to promote binding was necessitated by the reduced membrane associations of the opened-ring form of the agent relative to the closed-ring lactone form of the agent. The emission maxima for DB-91 carboxylate in PBS is 549 nm and this value shifts to lower values ($\lambda_{max}$ of 450 nm in the presence of DMPC vesicles and $\lambda_{max}$ of 446 nm in the presence of DMPG vesicles).

Normalized fluorescence emission spectra of 1 μM of the lactone versus carboxylate forms of 7-t-butyldimethylsilyl-10-aminohomocamptothecin (DB-90 and DB-90 carboxylate, respectively) in PBS at 37° C. were studied. Fluorescence emission spectral data indicate that upon ring opening there is a slight shifting of the spectra to the shorter wavelength region (or shifting of the spectra more towards the blue region of light). The two spectra were recorded using exciting light of 402 nm.

Normalized fluorescence emission spectra of 1 μM of the lactone versus carboxylate forms of 7-t-butyldimethylsilyl-10-hydroxylhomocamptothecin (DB-91 and DB-91 carboxylate, respectively) in PBS at 37° C. were acquired. Fluorescence emission spectral data indicate that upon ring opening there is a slight shifting of the spectra to the shorter wavelength region (or shifting of the spectra more towards the blue region of light) The two spectra were recorded at 394 nm.

Direct Observation of Fluorescence Spectral Changes Upon Homosilatecan Partitioning in Red Blood Cells Spectral recordings were initiated and completed shortly after the addition of the lactone form of the agent to solution, thereby assuring that the detected signal originates predominantly from the lactone form of the agent (and not the ring-opened form). The emission maxima for DB-91 in PBS is 554 nm but this value shifts significantly to a $\lambda_{max}$ of approximately 410 nm in anhydrous ethanol. Because DB-91 contains a 10-hydroxy functionality, the possibility exists that fluorescence can occur from two distinct species. In an aprotic solvent or non-aqueous microenvironment a protonated (with respect to the 10-hydroxy functionality) species predominates, while in protic solvents such as water a deprotonated excited-state complex predominates. The 554 nm peak is correlated with the deprotonated excited-state complex while the $\lambda_{max}$ of approximately 410 nm correlates with the protonated excited-state complex. The formation of the deprotonated excited-state complex is greatly facilitated by the presence of water; even at small amounts of water such as 1% a peak is apparent around 550 nm which correlates with the water-facilitated formation of the deprotonated excited-state complex. In FIGS. 6 and 7 we study the extent of protonated excited-state complex formation and use this parameter as a relative measure of lipophilicity for two 7-modified camptothecins (DB-91 and SN-38) with each containing the 10-hydroxy functionality. Spectral recordings were initiated and completed shortly after the addition of the lactone form of the agent to solution, thereby assuring that the detected signal originates predominantly from the lactone form of the agent (and not the ring-opened form). The emission maxima for DB-91 in PBS is 554 nm. In the presence of red blood cells, a peak with a significantly lower $\lambda_{max}$ value is observed indicating that the agent is capable of partitioning into the red blood cell membranes. The membranes of the red blood cells provide a hydrophobic microenvironment from which the protonated excited-state complexes can form and fluoresce from. Comparison of the emission spectra of DB-91 in the presence of human erythrocytes with that of clinically relevant 7-ethyl-10-hydroxycamptothecin (FIG. 7) indicate there is more extensive protonated excited-state complex formation in the case of DB-91. These findings corroborate model membrane studies indicating the membrane binding of SN-38 is significantly less than the extensive interactions noted for DB-91 (SN-38 displays a $K_{DMPC}$ value of 300 $M^{-1}$ whereas DB-91 displays a $K_{DMPC}$ value of 8,000 $M^{-1}$). The novel homosilatecan DB-91 is a more lipophilic, erythrocyte-interactive agent relative to the known compound 7-ethyl-10-hydroxycamptothecin (SN-38). The emission maxima for SN-38 in PBS is approximately 550 nm. The SN-38 agent, like DB-91, also contains a 10-hydroxy functionality and, as a consequence, SN-38 also displays fluorescence spectral characteristics which are sensitive to the presence of water. In the presence of red blood cells, a peak with a significantly lower $\lambda_{max}$ value (approximately 440 nm) is observed for SN-38 indicating that the agent is capable of partitioning into the red blood cell membranes. However, the peak at the lower $\lambda_{max}$ value is reduced for SN-38 relative to the situation observed for DB-91 (see FIG. 6). These results indicate there is more extensive protonated excited-state complex formation in the case for DB-91, corroborating that the novel homosilatecan DB-91 is a more lipophilic, erythrocyte-interactive agent relative to the known compound 7-ethyl-10-hydroxycamptothecin (SN-38).

Anticancer Activities of Homosilatecans as Determined By In Vitro Cell Culture Experiments Cytotoxicity measurements were conducted using MDA-MB-435 tumorigenic human breast cancer cells. The cells were exposed to a range of drug concentrations for 72 hr exposure periods and then viability was assessed using a sulphorrhodamine B (SRB) assay. The SRB measures the total protein levels in the living cells. Proteins from dead cells are lysed and removed in the washing step before TCA fixation. However, it is possible that cells in the early stage of death still have their membrane integrity and therefore retain the protein contents inside. As a result, the optical density at 490 nm can sometimes be overestimated and the cytotoxicity underestimated. To validate the SRB assay, a diverse range of chemotherapeutic agents have been tested across multiple panels of tumor cell lines, and close correlations have been found with standard tetrazolium (MIT) assay and clonogenic assays. The SRB assay is now a well regarded assay and was recently approved by NCI as a standard assay for anticancer drug screening. Using the SRB assay, the cytotoxicity values for cells exposed to our novel homosilatecans for 72 hrs. were determined. Cytotoxicities of homosilatecans and camptothecin against MDA-MB-435 tumorigenic metastatic human breast cancer cells in the absence and presence of human serum albumin were determined and are summarized in Table 5. Each $IC_{50}$ value represents the average of three separate trials with each dosage level studied in triplicate.

(+/−) 4-Ethyl-8-methoxy-6-trimethylsilanyl-3,4-dihydro-1H-pyrano[3,4-c]pyridine-3,4-diol (4)

To a round bottom flask was added N-Methylmorpholine N-oxide (0.89 g, 7.6 mmol) followed by $H_2O$ (10 mL) and t-BuOH (10 mL). A 2.5 weight percent solution of $OsO_4$ in t-BuOH (0.5 mL) was added followed by enol ether (3) (0.5 g, 1.9 mmol). After 12 hours, at 22° C., $Na_2SO_3$ (1.0 g) was added to the mixture. After 30 minutes the mixture was diluted with $H_2O$ (100 mL) and extracted with $CH_2Cl_2$ (2×100 mL). The organic layer was dried ($MgSO_4$) and the crude residue was chromatographed (hexanes:EtOAc 3:1) to yield lactol (4) 0.55 g (98%) as a white solid: IR ($CHCl_3$, $cm^{-1}$) 3602, 3569, 3398, 3022, 2950, 1579, 1456, 1351; $^1H$ NMR (300 MHz, $CDCl_3$) δ 0.22 (s, 9H), 0.83 (t, J=7 Hz, 3H), 1.71–1.79 (m, J=7 Hz, 2H), 2.91 (s, 1H), 3.90 (s,3H), 4.19 (d, J=5 Hz, 1H), 4.53 (d, J=16 Hz, 1H), 4.70 (d, J=16 Hz, 1H), 5. 06 (d, J=5 Hz, 1H), 7.25 (s, 1H); $^{13}C$ NMR (75 MHz, $CDCl_3$) δ −1.7, 7.8, 31.5, 53.1, 58.8, 70.9, 93.8, 115.1, 119.7, 145.8, 158.0, 162.8; HRMS (EI) m/z calcd for $C_{14}H_{23}NO_4Si$ ($M^+$) 473.0519, found 473.0507 LRMS (EI) m/z 473 ($M^+$), 458, 386, 360, 346, 139, 73, 57.

Formic acid 2-methoxy-4-propionyl-6-trimethylsilanyl-pyridin-3-yl methyl ester (5)

To a round bottom flask was added lactol (4) (0.100 g, 0.34 mmol) followed by AcOH (9 mL) and lead tetraacetate (0.18 g, 0.406 mmol). After 3 hours at 50° C. the mixture was poured into ice cold sat. $NaHCO_3$ and extracted with ether (3×75 mL). The organic layer was dried ($MgSO_4$) and chromatographed (hexanes:EtOAc 95:5) to yield keto-formate ester (5) 91 mg (91%) as a clear oil: IR (neat, $cm^{-1}$) 2963, 2902, 1733, 1556, 1455, 1345; $^1H$ NMR (300 MHz, $CDCl_3$) δ 0.30 (s, 9H), 1.21 (t, J=7 Hz,3H), 2.75–2.95 (m, J=7 Hz, 2H), 4.02 (s, 3H), 5.28 (s, 2H), 7.07 (s, 1H), 8.05 (s, 1H); $^{13}C$ NMR (75 MHz, $CDCl_3$) δ −1.8, 7.9, 35.9, 54.0, 57.6, 112.9, 118.7, 148.5, 160.8, 162.2, 167.6, 205.6; HRMS (EI) m/z calcd for $C_{14}H_{21}NO_4Si$ ($M^+$) 295.1240, found 295.1239 LRMS (EI) m/z 295 ($M^+$), 280, 267, 250, 234, 222, 206, 176, 162, 103, 89, 79, 73, 57.

(+/−) 3-Hydroxy-3-(3-hydroxymethyl-2-methoxy-6-trimethylsilanyl-pyridin-4-yl)-pentanoic acid tert-butyl ester (6)

To a flame dried flask was added keto-formate ester (5) (0.5 g, 1.69 mmol) followed by dioxane (20 mL). α-Bromo-tert-butylacetate (0.9 mL, 6.08 mmol) was added followed by activated Zn (0.59 g, 9.1 mmol). The Zn was activated by the Cava method as set forth in the *J. Organic. Chem.*, 47, p. 5030 (1982), the disclosure of which is incorporated herein by reference. Next $I_2$ (0.16 g, 0.63 mmol) was added and the mixture was sonicated for 3.2 hours. After sonication the mixture was diluted with $H_2O$ (100 mL) and ether (100 mL). The resulting emulsion was filtered through a pad of celite, the phases were separated and the aqueous layer was extracted with ether (2×100 mL). The combined ether extracts were dried ($MgSO_4$) and chromatographed (hexanes:EtOAc 85:15) to yield beta-hydroxy ester (6) 0.50 g (78%) as a clear oil: IR (neat, $cm^{-1}$) 3469, 2980, 1705, 1575, 1545, 1447, 1342, 1248, 1153; $^1H$ NMR (300 MHz, $C_6D_6$) δ 0.38 (s, 9H), 0.79 (t, J=7 Hz, 3H), 1.15 (s, 9H), 1.75–1.92 (m, J=7 Hz, 2H), 2.52 (d, J=16 Hz, 1H), 2.79 (d, J=16 Hz, 1H), 3.03 (t, J=7 Hz, 2H), 3.74 (s, 3H), 5.18 (d, J=7 Hz, 2H), 5.19 (s, 1H), 7.18 (s, 1H); $^{13}C$ NMR (75 MHz, $C_6D_6$) δ −1.9, 8.1, 27.6, 35.5, 45.6, 53.0, 57.0, 77.3, 81.5, 120.9, 121.8, 152.3, 162.6, 163.3, 172.3; HRMS (EI) m/z calcd for $C_{19}H_{31}NO_4Si$ ($M-H_2O$) 365.2022, found 365.2028 LRMS (EI) m/z 383 ($M^+$), 365, 336, 309, 280, 262, 250, 208, 89, 73, 57.

(+/−) 5-Ethyl-4,5-dihydro-5-hydroxy-7-trimethylsilyl-9-methoxyoxepino[3,4-c]pyridin-3(1H)-one (7)

To a 100 mL flask was added the beta hydroxy ester (6) (0.75 g, 1.9 mmol) followed by trifluoroacetic acid (150 mL). After 24 hours, the mixture was poured into sat. $NaHCO_3$ (pH 8) and extracted with ether (3×100 mL). The organic phase was dried ($MgSO_4$) and chromatographed (hexanes:EtOAc 2:1) to give beta-hydroxy lactone (7) 0.48 g (79%) as a white solid: IR ($CHCl_3$, $cm^{-1}$) 3020, 2978, 2873, 1742, 1561, 1448, 1384, 1348, 1110, 909, 842; $^1H$ NMR (300 MHz, $CDCl_3$) δ 0.22 (s, 9H), 0.83 (t, J=7 Hz, 3H), 1.81–1.88 (m, J=7 Hz, 2H), 1.37 (br s, 1H), 3.00 (d, J=14 Hz, 1H), 3.32 (d, J=14 Hz, 1H), 3.91 (s, 3H), 5.18.(d, J=15 Hz, 1H), 5.42 (d, J=15 Hz, 1H), 7.26 (s, 1H); $^{13}$C NMR (75 MHz, CDCl$_3$) δ −1.9, 8.4, 33.9, 42.9, 53.8, 62.2, 73.8, 114.7, 121.2, 151.6, 159.8, 165.9, 172.3; HRMS (EI) m/z calcd for C$_{15}$H$_{23}$NO$_4$Si (M$^+$) 309.1396, found 309.1399 LRMS (EI) m/z 309 (M$^+$), 294, 266, 252, 238, 89.

(+/−) 5-Ethyl-4,5-dihydro-5-hydroxy-7-iodo-9-methoxyoxepino[3,4-c]pyridin-3(1H)-one (8)

To a flame dried flask at 0° C. was added beta hydroxy lactone (7) (0.94 g, 3.0 mmol) followed by dry CH$_2$Cl$_2$ (25 mL). ICl (3.2 g, 19.7 mmol), was added to a flame dried flask at −78° C. The flask was taken out of the bath, warmed slightly, excess moisture was wiped from the outside and it was quickly weighed under nitrogen. After weighing it was returned to the −78° C. bath and diluted with ice cold CCl$_4$ (16 mL) to give a 1.2 M solution of ICl. The resulting ICl solution was transferred to an ice bath and allowed to equilibrate to 0° C. A portion of the ICl solution (10.1 mL) was transferred to the mixture dropwise in the dark. After 16 hours in the dark, the mixture was poured into a 1:1 solution (100 mL) of 5% Na$_2$SO$_3$ and sat. Brine and extracted with EtOAc (3×100 mL). The organic layer was dried (MgSO$_4$) and chromatographed (hexanes:EtOAc 3:1) to give beta hydroxy lactone (7) 0.43 g (46%) and iodolactone (8) 0.41 g (37%): IR (CHCl$_3$, cm$^{-1}$) 2974, 2951, 1747, 1573, 1554, 1359, 1278, 1212, 1054, 870; $^1$H NMR (300 MHz, CDCl$_3$) δ 0.84 (t, J=7 Hz, 3H), 1.78–1.85 (m, J=7 Hz, 2H), 2.98 (br d, J=14 Hz, 2H), 3.30 (d, J=14 Hz, 1H), 3.90 (s, 3H), 5.10 (d, J=15 Hz, 1H), 5.35 (d, J=15 Hz, 1H), 7.51 (s, 1H); $^{13}$C NMR (75 MHz, CDCl$_3$) δ 8.4, 37.4, 42.7, 55.0, 61.8, 73.4, 114.0, 114.9, 127.3, 155.3, 159.8, 171.9; HRMS (EI) m/z calcd for C$_{12}$H$_{14}$INO$_4$ (M$^+$) 362.9967, found 362.9955 LRMS (EI) m/z 363 (M$^+$), 334, 326, 317, 302, 292, 262, 234, 162, 137, 120, 57.

(+/−) 5-Ethyl-1,4,5,8-tetrahydro-5-hydroxy-7-iodooxepino[3,4-c]pyridine-3,9-dione (9)

To a flame dried flask was added iodolactone (8) (0.33 g, 0.90 mmol) followed by dry acetonitrile (12 mL). Sodium iodide (0.22 g, 1.44 mmol) was added followed by chlorotrimethylsilane (0.18 mL, 1.44 mmol). The resulting mixture was stirred at 22° C. for 15 minutes at which point H$_2$O (7.6 μL, 0.42 mmol) was added and the mixture was heated at 60° C. After 5 hours at 60° C. the mixture was poured into a 1:1 solution of 5% Na$_2$SO$_3$/Brine (75 mL) and then quickly extracted with EtOAc (6×75 mL). The organic layer was dried (MgSO$_4$) and chromatographed (CH$_2$Cl$_2$:MeOH 95:5) to yield iodopyridone (9) as a white solid 0.19 g (61%): $^1$H NMR (300 MHz, CDCl$_3$/CD$_3$OD) δ 0.62 (t, J=7 Hz, 3H), 1.45–1.54 (m, J=7 Hz, 2H), 2.80 (d, J=14 Hz, 1H), 2.97 (d, J=14 Hz, 1H), 4.93 (d, J=15 Hz, 1H), 5.06 (d, J=15 Hz, 1H), 6.66 (s, 1H); $^{13}$C NMR (75 MHz, CDCl$_3$) δ 7.5, 35.6, 41.9, 61.6, 72.5, 94.4, 118.3, 121.1, 156.5, 162.6, 172.7; HRMS (EI) m/z calcd for C$_{11}$H$_{12}$INO$_4$ (M$^+$) 348.9811, found 348.9815 LRMS (EI) m/z 349 (M$^+$), 331, 320, 303, 289, 278, 264, 250, 162, 150, 122, 94, 57.

Preparation of N-Alkylated iodopyridones (+/−) 5-Ethyl-1,4,5-trihydro-5-hydroxy-7-iodo-8-(3-trimethylsilyl-2-propynyl)-oxepino[3,4-c]pyridine-3,9-dione (10a)

To a flame dried flask was added iodopyridone (9) (0.16 g, 0.46 mmol) followed by dry DME (3.8 mL) and DMF (0.95 mL). This solution was lowered to 0° C. and NaH, 60% dispersion in oil, (19.3 mg, 0.483 mmol) was added portionwise. After 15 minutes 2 eq of vacuum flame dried LiBr (81 mg, 0.92 mmol) was added and the mixture was raised to 22° C. After 25 minutes at 22° C., the trimethylsilylpropargyl bromide (0.130 mL, 0.92 mmol) was added and the mixture was heated at 65° C. After 16 hours, the mixture was poured into brine (50 mL) and extracted with EtOAc (8×30 mL). The EtOAc layer was dried (MgSO$_4$) and chromatographed (CH$_2$Cl$_2$:EtOAc 80:20) to give the desired N alkylated pyridone (10a) 134 mg (63%) as a white foam: $^1$H NMR (300 MHz, CDCl$_3$) δ 0.005 (s, 9H), 0.80 (t, J=7 Hz, 3H), 1.60–1.74 (m, J=7 Hz, 2H), 2.94 (d, J=14 Hz, 1H), 3.11 (d, J=14 Hz, 1H), 3.60 (br s, 1H), 4.82 (d, J=17 Hz, 1H), 5.01 (d, J=17 Hz, 1H), 5.09 (d, J=15 Hz, 1H), 5.26 (d, J=15 Hz, 1H), 7.01 (s, 1H); $^{13}$C NMR (75 MHz, CDCl$_3$/CD$_3$OD) δ −0.44, 7.9, 35.7, 42.2, 45.2, 62.3, 72.6, 90.7, 98.1, 99.2, 119.9, 122.3, 155.1, 160.6, 172.6; HRMS (EI) m/z calcd for C$_{17}$H$_{22}$INO$_4$Si (M$^+$) 459.0363, found 459.0366 LRMS (EI) m/z 459 (M$^+$), 444, 388, 306, 111, 96, 83, 73, 57.

(+/−) 5-Ethyl-1,4,5-trihydro-5-hydroxy-7-iodo-8-(3-tert-butyldimethylsilyl-2-propynyl)-oxepino[3,4-c]pyridine-3,9-dione (10b)

Following the procedure outlined above iodopyridone (7) (0.16 g, 0.46 mmol) was N alkylated with the TBDMS propargyl bromide (0.21 g, 0.92 mmol). Flash chromatography (CH$_2$Cl$_2$:EtOAc 9:1) gave iodopyridone (8b) 134 mg (58%) as a white foam: $^1$H NMR (300 MHz, CDCl$_3$) δ 0.097 (s, 6H), 0.92 (br s, 12H), 1.82–1.89 (br m, 2H), 3.01 (d, J=14 Hz, 1H), 3.33 (d, J=14 Hz, 1H), 3.48 (br s, 1H), 5.07 (s, 2H), 5.12 (d, J=15 Hz, 1H), 5.47 (d, J=15 Hz, 1H), 7.10 (s, 1H); $^{13}$C NMR (75 MHz, CDCl$_3$) δ −4.7, 8.3, 16.6, 26.3, 36.0, 42.6, 45.3, 62.8, 73.5, 89.4, 98.6, 99.5, 119.5, 122.9, 154.1, 160.4, 172.0; HRMS (EI) m/z calcd for C$_{20}$H$_{28}$INO$_4$Si (M$^+$) 501.0832, found 501.0843 LRMS (EI) m/z 501 (M$^+$), 444, 402, 335, 318, 169, 121, 96, 57.

(+/−) 5-Ethyl-1,4,5,13-tetrahydro-5-hydroxy-12-trimethylsilyl-3H,15H-oxepino[3',4':6,7]indolizino[1,2-b]quinoline-3,15-dione (1 h)(7-trimethylsilylhomocamptothecin)

To an oven dried pressure tube under Ar was added the iodopyridone (10a) (15 mg, 0.033 mmol) followed by benzene (0.25 mL) and t-BuOH (0.5 mL). Next phenylisonitrile (13.6 mg, 0.13 mmol) and hexamethylditin (16.0 mg, 0.049 mmol) were added and the tube was flushed with Ar, sealed and placed in front of a 275W GE sunlamp. After 12 hours of irradiation, the mixture was concentrated and chromatographed (CH$_2$Cl$_2$:acetone 5:1) to yield homocamptothecin (1 h) 5.2 mg (36%) as a tan solid: $^1$H NMR (300 MHz, CDCl$_3$/CD$_3$OD) δ 0.64 (s, 9H), 0.96 (t, J=7 Hz, 3H), 1.96–2.05 (m, J=7 Hz, 2H), 3.19 (d, J=14 Hz, 2H), 3.46 (d, J=14 Hz, 1H), 5.34 (s, 2H), 5.44 (d, J=15 Hz, 1H), 5.63 (d, J=15 Hz, 1H), 7.65–7.71 (m, 2H), 7.78–7.84 (m, 1H), 8.18 (d, J=8 Hz, 1H), 8.27 (d, J=8 Hz, 1H); HRMS (EI) m/z calcd for C$_{24}$H$_{26}$N$_2$O$_4$Si (M$^+$) 434.1662, found 434.1679 LRMS (EI) m/z 434 (M$^+$), 419, 388, 374, 363, 347, 335, 320, 303, 289, 275, 261, 247, 231, 219, 174, 149, 73.

(+/−) 5-Ethyl-1,4,5,13-tetrahydro-5-hydroxy-10-(tert-butyloxy carbonylamino)-12-trimethylsilyl-3H,15H-oxepino[3',4':6,7]indolizino[1,2-b]quinoline-3,15-dione (1c)(10-tert-butyloxycarbonylamino-7-trimethylsilylhomocamptothecin)

Following the procedure described above, iodopyridone (10a) (30 mg, 0.065 mmol) was reacted with para-bocaminophenylisonitrile (57 mg, 0.26 mmol) and hexamethylditin (32.2 mg, 0.1 mmol) in benzene (0.5 mL) and t-BuOH (1 mL). Chromatography (CH$_2$Cl$_2$:Acetone 7:1) gave compound (1c) 18.8 mg (53%) as a brown solid: IR (CHCl$_3$, cm$^{-1}$) 3022, 3007, 1736, 1655, 1594, 1528, 1155, 1062; $^1$H NMR (500 MHz, CDCl$_3$) δ 0.70 (s, 9H), 0.96 (t, J=7 Hz, 3H), 1.61 (s, 9H), 1.85–2.10 (m, J=7 Hz, 2H), 3.31 (d, J=13 Hz, 1H), 3.41 (d, J=13 Hz, 1H), 5.11 (d, J=19 Hz, 1H), 5.34–5.41 (m, 2H), 5.61 (d, J=15 Hz, 1H), 6.96 (s, 1H), 7.19–7.40 (m, 1H), 7.62 (s, 1H), 8.37 (s, 1H); $^{13}$C NMR (125 MHz, CDCl$_3$) δ 1.43, 8.3, 28.4, 35.8, 42.6, 52.4, 62.3, 73.9, 81.2, 100.3, 115.1, 122.2, 123.0, 130.7, 132.6, 134.8, 137.1, 143.4, 143.6, 145.1, 148.2, 152.6, 156.5, 159.8, 171.8; HRMS (EI) m/z calcd for C$_{29}$H$_{35}$N$_3$O$_6$Si (M$^+$) 549.2295, found 549.2274 LRMS (EI) m/z 549 (M$^+$), 493, 475, 449, 433, 415, 404, 389, 378, 350, 304, 260, 195, 182, 73.

(+/−) 5-Ethyl-1,4,5,13-tetrahydro-5-hydroxy-10-acetoxy-12-trimethylsilyl-3H,15H-oxepino[3',4':6,7]indolizino[1,2-b]quinoline-3,15-dione(10-acetoxy-7-trimethylsilylhomocamptothecin)

Following the procedure described above, iodopyridone (10a) (30 mg, 0.065 mmol) was reacted with para-acetoxyphenylisonitrile (42 mg, 0.26 mmol) and hexamethylditin (32.2 mg, 0.1 mmol) in benzene (0.5 mL) and t-BuOH (1 mL). Chromatography (CH$_2$Cl$_2$:Acetone 5:1) gave the product 6.6 mg (21%) as a tan solid: IR (CHCl$_3$, cm$^{-1}$) 3025, 2992, 2953, 1753, 1657, 1600, 1504, 1193; $^1$H NMR (300 MHz, CDCl$_3$) δ 0.67 (s, 9H), 0.98 (t, J=7 Hz, 3H), 1.99–2.07 (m, 2H), 2.42 (s, 3H), 3.26 (d, J=14 Hz, 1H), 3.45 (d, J=14 Hz, 1H), 3.66 (br s, 1H), 5.18 (d, J=19 Hz, 1H), 5.35 (d, J=15 Hz, 1H), 5.39 (d, J=19 Hz, 1H), 5.66 (d, J=15 Hz, 1H), 7.38 (dd, J$_1$=9 Hz, J$_2$=2 Hz, 1H), 7.40 (s, 1H), 7.88 (d, J=9 Hz, 1H), 7.92 (d, J=2 Hz, 1H); $^{13}$C NMR (125 MHz, CDCl$_3$) δ 1.6, 8.3, 21.5, 35.9, 42.6, 52.2, 62.2, 74.0, 100.5, 118.9, 122.9, 124.7, 131.3, 132.2, 135.0, 144.1, 144.8, 145.0, 148.9, 150.0, 156.0, 159.7, 169.1, 171.5; HRMS (EI) m/z calcd for C$_{26}$H$_{28}$N$_2$O$_6$Si (M$^+$) 492.1717, found 492.1707 LRMS (EI) m/z 492 (M$^+$), 477, 459, 450, 432, 421, 403, 393, 379, 365, 351, 336, 147.

(+/−) 5-Ethyl-1,4,5,13-tetrahydro-5-hydroxy-12-tert-butyldimethylsilyl-3H,15H-oxepino[3',4':6,7]indolizino[1,2-b]quinoline-3,15-dione (1g) (7-tert-butyldimethylsilylhomocamptothecin)

Following the procedure described above, iodopyridone (10b) (25 mg, 0.05 mmol) was reacted with phenylisonitrile (15.5 mg, 0.15 mmol) and hexamethylditin (25 mg, 0.075 mmol) in benzene (0.75 mL). Chromatography (CH$_2$Cl$_2$:Acetone 7:1) gave compound (1g) 6.4 mg (27%) as a tan solid: IR (CHCl$_3$, cm$^{-1}$) 3027, 2958, 2932, 2859, 1745, 1655, 1600, 1269, 1065; $^1$H NMR (300 MHz, CDCl$_3$) δ 0.69 (s, 3H), 0.70 (s, 3H), 0.92 (t, J=7 Hz, 3H), 1.00 (s, 9H), 1.92–2.02 (m, J=7 Hz, 2H), 3.23 (d, J=13 Hz, 1H), 3.39 (d, J=13 Hz, 1H), 3.90(br s, 1H), 5.11 (d, J=19 Hz, 1H), 5.31 (d, J=15 Hz, 1H), 5.40 (d, J=19 Hz, 1H), 5.60 (d, J=15 Hz, 1H), 7.35 (s, 1H), 7.39–7.49 (m, 2H), 7.70 (d, J=8 Hz, 1H), 8.07 (d, J=8 Hz, 1H); $^{13}$C NMR (75 MHz, CDCl$_3$) δ −0.5, −0.3, 8.3, 19.4, 27.3, 35.9, 42.7, 52.9, 62.3, 74.0, 100.3, 122.8, 126.9, 129.4, 130.3, 132.7, 136.0, 143.3, 145.3, 147.6, 150.1, 156.1, 159.9, 171.5; HRMS (EI) m/z calcd for C$_{27}$H$_{32}$N$_2$O$_4$Si (M$^+$) 476.2131, found 476.2118 LRMS (EI) m/z 476 (M$^+$), 458, 430, 419, 405, 389, 377, 361, 345, 319, 304, 275, 149, 117, 91, 73, 56.

(+/−) 5-Ethyl-1,4,5,13-tetrahydro-5-hydroxy-10-(tert-butyloxycarbonyl amino)-12-tert-butyldimethylsilyl-3H,15H-oxepino[3',4':6,7]indolizino[1,2-b]quinoline-3,15-dione (1a)(10-tert-butyloxycarbonylamino-7-tert-butyldimethylsilylhomocamptothecin)

Following the procedure described above, iodopyridone (10b) (45 mg, 0.089 mmol) was reacted with para-bocaminophenylisonitrile (58 mg, 0.27 mmol) and hexamethylditin (45 mg, 0.13 mmol) in benzene (1.3 mL). Chromatography (CH$_2$Cl$_2$:Acetone 10:1) gave compound (1a) 7.8 mg (15%) as a tan solid: IR (CHCl$_3$, cm$^{-1}$) 3435, 3022, 2931, 2859, 1738, 1654, 1563, 1528, 1156; $^1$H NMR (300 MHz, CDCl$_3$) δ 0.76 (s, 3H), 0.77 (s, 3H), 0.96 (t, J=7 Hz, 3H), 1.10 (s, 9H), 1.62 (s, 9H), 1.91–2.07 (m, J=7 Hz, 2H), 3.34 (d, J=14 Hz, 1H), 3.41 (d, J=14 Hz, 1H), 4.42 (br s, 1H), 5.09 (d, J=19 Hz, 1H), 5.38 (d, J=15 Hz, 1H), 5.47 (d, J=19 Hz, 1H), 5.62 (d, J=15 Hz, 1H), 6.99 (br s, 1H), 7.21–7.25 (m, 2H), 7.45 (d, J=9 Hz, 1H), 8.37 (d, J=2 Hz, 1H); $^{13}$C NMR (125 MHz, CDCl$_3$) δ −0.9, −0.5, 8.3, 19.6, 27.4, 28.4, 35.5, 42.7, 53.0, 62.2, 73.8, 81.1, 100.0, 116.2, 122.2, 123.0, 130.3, 133.5, 136.3, 136.9, 144.4, 145.2, 148.2, 152.6, 156.4, 160.0, 171.5; HRMS (EI) m/z calcd for C$_{32}$H$_{41}$N$_3$O$_6$Si (M$^+$) 591.2765, found 591.2751 LRMS (EI) m/z 534 (M-57), 516, 488, 477, 459, 435, 417, 393, 375, 111, 97, 83, 69, 57.

(+/−) 5-Ethyl-1,4,5,13-tetrahydro-5-hydroxy-10-acetoxy-12-tert-butyldimethylsilyl-3H,15H-oxepino[3',4':6,7]indolizino[1,2-b]quinoline-3,15-dione (1e) (10-acetoxy-7-tert-butyldimethylsilylhomocamptothecin)

Following the procedure described above, iodopyridone (10b) (45 mg, 0.089 mmol) was reacted with para-acetoxyphenylisonitrile (43 mg, 0.27 mmol) and hexamethylditin (45 mg, 0.13 mmol) in benzene (1.3 mL). Chromatography (CH$_2$Cl$_2$:Acetone 10:1) gave compound (1e) 9.6 mg (20%) as a tan solid: $^1$H NMR (300 MHz, CDCl$_3$) δ 0.73 (s, 3H), 0.74 (s, 3H), 0.97 (t, J=7 Hz, 3H), 1.07 (s, 9H), 1.94–2.08 (m, J=7 Hz, 2H), 2.42 (s, 3H), 3.29 (d, J=14 Hz, 1H), 3.44 (d, J=14 Hz, 1H), 4.05 (br s, 1H), 5.16 (d, J=19 Hz, 1H), 5.37 (d, J=15 Hz, 1H), 5.48 (d, J=19 Hz, 1H), 5.65 (d, J=15 Hz, 1H), 7.31 (dd, J$_1$=9 Hz, J$_2$=2 Hz, 1H), 7.36 (s, 1H), 7.70 (d, J=9 Hz, 1H), 7.97 (d, J=2 Hz, 1H); $^{13}$C NMR (125 MHz, CDCl$_3$) δ −0.7, −0.5, 8.3, 19.3, 21.5, 27.2, 35.8, 42.7, 52.9, 62.2, 73.9, 100.4, 120.1, 122.8, 124.7, 131.1, 133.0, 136.5, 143.0, 145.0, 145.4, 148.9, 149.9, 156.2, 159.9, 169.0, 171.5; HRMS (EI) m/z calcd for C$_{29}$H$_{34}$N$_2$O$_6$Si (M$^+$) 534.2186, found 534.2188 LRMS (EI) m/z 534 (M$^+$), 516, 488, 477, 459, 435, 417, 393, 375, 335, 320, 291, 275, 234, 164, 137, 125, 111, 97, 83, 69, 57.

(+/−) 5-Ethyl-1,4,5,13-tetrahydro-5-hydroxy-10-hydroxy-12-tert-butyldimethylsilyl-3H,15H-oxepino[3',4':6,7]indolizino[1,2-b]quinoline-3,15-dione (1f) (10-hydroxy-7-tert-butyldimethylsilylhomocamptothecin)

Compound (1e) (11.9 mg, 0.022 mmol) was dissolved in H$_2$O (0.3 mL) and MeOH (0.3 mL). Next K$_2$CO$_3$ (7.5 mg, 0.054 mmol) was added and the mixture was stirred at 22° C. After 4 h the solvent was evaporated and the residue was dissolved in CH$_2$Cl$_2$ (2 mL) and TFA (2 mL). After stirring at 22° C. for 16 h sat. NaHCO$_3$ was carefully added until pH 5 was attained. At this point the solution was extracted with EtOAc (3×10 mL) and the organic layer was dried (Na$_2$SO$_4$) and concentrated. The residue was chromatographed twice (1:CH$_2$Cl$_2$:MeOH:AcOH 94:5:1) (2:CH$_2$Cl$_2$:Acetone 5:1) to give compound (1f) 8.6 mg (79%) as a yellow solid: $^1$H NMR (300 MHz, CDCl$_3$/CD$_3$OD) δ 0.65 (s, 6H), 0.90–0.99 (m, 12H), 1.89–2.05 (m, 2H), 3.14 (d, J=14 Hz, 1H), 3.34 (d, J=14 Hz, 1H), 5.23 (s, 2H), 5.35 (d, J=15 Hz, 1H), 5.57 (d, J=15 Hz, 1H), 7.42 (dd, J$_1$=9 Hz, J$_2$=2 Hz, 1H), 7.58 (d, J=2 Hz, 1H), 7.70 (s, 1H), 8.16 (d, J=9 Hz, 1H); 13C NMR (125 MHz, CDCl$_3$/CD$_3$OD) δ −1.1, 8.1, 19.2, 26.9, 36.1, 42.1, 52.8, 62.1, 73.5, 101.8, 111.5, 122.7, 123.6, 127.5, 129.0, 135.0, 136.6, 139.8, 143.1, 145.5, 156.7, 156.9, 159.6, 172.8; HRMS (EI) m/z calcd for C$_{27}$H$_{32}$N$_2$O$_5$Si (M$^+$) 492.2080, found 492.2087 LRMS (EI) m/z 492 (M$^+$), 474, 446, 435, 421, 393, 375, 346, 335, 315, 291, 273, 259, 231, 183, 155.

(+/−) 5-Ethyl-1,4,5,13-tetrahydro-5-hydroxy-10-amino-12-tert-butyldimethylsilyl-3H,15H-oxepino[3',4':6,7]indolizino[1,2-b]quinoline-3,15-dione (1b) (10-amino-7-tert-butyldimethylsilylhomocamptothecin)

Trifluoroacetic acid (0.1 mL) was added to a solution containing CH$_2$Cl$_2$ (0.5 mL) and compound (1a) (8.1 mg, 0.014 mmol) and the contents were stirred at 22° C. After 5 h the mixture was poured into sat. NaHCO$_3$ (2 mL) and extracted with EtOAc (6×2 mL). The EtOAc was dried (Na$_2$SO$_4$), concentrated and chromatographed (CH$_2$Cl$_2$:MeOH 96:4) to give (1b) 6 mg (89%) as a yellow solid: $^1$H NMR (300 MHz, CDCl$_3$/CD$_3$OD) δ 0.28 (s, 6H), 0.78–0.88 (m, 12H), 1.78–1.90 (m, 2H), 3.04 (d, J=14 Hz, 1H), 3.24 (d, J=14 Hz, 1H), 5.02–5.11 (m, 2H), 5.24 (d, J=15 Hz, 1H), 5.46 (d, J=15 Hz, 1H), 7.20 (s, 1H), 7.26 (dd, J$_1$=9 Hz, J$_2$=2 Hz, 1H); $^{13}$C NMR (125 MHz, CDCl$_3$/CD$_3$OD) δ −1.0, 8.0, 19.1, 26.9, 36.1, 42.1, 52.7, 62.1, 73.4, 100.7, 122.0, 123.2, 130.5, 134.3, 136.8, 141.8, 144.2, 147.1, 156.7, 159.7, 172.8; HRMS (EI) m/z calcd for C$_{27}$H$_{33}$N$_3$O$_4$Si (M$^+$) 491.2240, found 491.2242 LRMS (EI) m/z 491 (M$^+$), 434, 392, 376, 319, 279, 262, 223, 178, 167, 149, 136, 121, 107, 91, 77, 57.

(+/−) 5-Ethyl-1,4,5,13-tetrahydro-5-hydroxy-10-amino-12-trimethylsilyl-3H,15H-oxepino[3',4':6,7]indolizino[1,2-b]quinoline-3,15-dione (1d) 10-amino-7-trimethylsilylhomocamptothecin)

Trifluoroacetic acid (0.1 mL) was added to a solution containing CH$_2$Cl$_2$ (0.5 mL) and compound (1c) (6.6 mg, 0.012 mmol) and the contents were stirred at 22° C. After 5 h the mixture was poured into sat. NaHCO$_3$ (2 mL) and extracted with EtOAc (6×2 mL). The EtOAc was dried (Na$_2$SO$_4$), concentrated and chromatographed (CH$_2$Cl$_2$:MeOH 95:5) to give (1d) 2.5 mg (45%) as an orange-red solid: $^1$H NMR (300 MHz, CDCl$_3$/CD$_3$OD) δ 0.60 (s, 9H), 0.94 (t, J=7 Hz, 3H), 1.92–2.05 (m, 2H), 3.16 (d, J=14 Hz, 1H), 3.46 (d, J=14 Hz, 1H), 5.24 (s, 2H), 5.40 (d, J=15 Hz, 1H), 5.61 (d, J=15 Hz, 1H), 7.25–7.32 (m, 2H), 7.52 (s, 1H), 7.89 (d, J=9 Hz, 1H); $^{13}$C NMR (125 MHz, CDCl$_3$/CD$_3$OD) δ −0.12, 7.1, 35.7, 41.5, 51.6, 61.3, 72.8, 99.3, 107.0, 120.4, 121.7, 129.9, 133.6, 134.4, 139.5, 141.0, 144.7, 145.2, 146.4, 156.2, 159.3, 172.6; HRMS (EI) m/z calcd for C$_{24}$H$_{27}$N$_3$O$_4$Si (M$^+$) 449.1771, found 449.1791 LRMS (EI) m/z 449 (M$^+$), 434, 402, 389, 374, 350, 335, 304, 178, 73. (+/−).

5-Ethyl-1,4,5-trihydro-5-hydroxy-7-iodo-8-(5-trimethylsilyl-2-pentynyl)oxepino[3,4-c]pyridine-3,9-dione (10c)

Following the procedure outlined above iodopyridone (9) (0.106 g, 0.92 mmol) was N-alkylated with the 2-trimethylsilylethyl propargyl bromide (0.43 g, 1.84 mmol). Flash chromatography (CH$_2$C$_{12}$:EtOAc 10:1) gave iodopyridone (10c) 68 mg (46%) as a light yellow foam: $^1$H NMR (300 MHz, CDCl$_3$) δ −0.069 (s, 9H), 0.72 (t, J=8 Hz, 2H), 0.87 (t, J=7 Hz, 3H), 1.70–1.88 (m, 2H), 2.10–2.20 (m, 2H), 2.96 (d, J=14 Hz, 1H), 3.15 (br s, 1H), 3.27 (d, J=14 Hz, 1H), 4.90–5.00 (m, 2H), 5.07 (d, J=15 Hz, 1H), 5.41 (d, J=15 Hz, 1H), 7.02 (s, 1H); $^{13}$C NMR (75 MHz, CDCl$_3$) δ −1.6, 8.2, 13.5, 15.7, 35.9, 42.5, 45.3, 62.7, 72.5, 73.4, 88.0, 99.7, 119.2, 122.8, 153.9, 160.4, 171.8; HRMS (EI) m/z calcd for C$_{19}$H$_{26}$INO$_4$Si (M$^+$) 487.0676, found 487.0676 LRMS (EI) m/z 487 (M$^+$), 472, 400, 374, 346, 96, 73.

(+/−) 5-Ethyl-1,4,5,13-tetrahydro-5-hydroxy-12-(2-trimethylsilylethyl)-3H,15H-oxepino[3',4':6,7]indolizino[1,2-b]quinoline-3,15-dione (1i) (7-(2-trimethylsilylethyl)homocamptothecin)

To an oven dried pressure tube under Ar was added the iodopyridone (10c) (16 mg, 0.033 mmol) followed by Benzene (0.5 mL). Next phenylisonitrile (10.2 mg, 0.1 mmol) and hexamethylditin (16.7 mg, 0.051 mmol) were added and the tube was flushed with Ar, sealed and placed in front of a 275W GE sunlamp. After 12 hours of irradiation, the mixture was concentrated and chromatographed (CH$_2$Cl$_2$:acetone 4:1) to yield the desired homocamptothecin (1i) 3.6 mg (24%) as a tan solid: $^1$H NMR (300 MHz, CDCl$_3$) δ 0.184 (s, 9H), 0.85–1.05 (m, 5H), 1.98–2.10 (m, 2H), 3.00–3.12 (m, 2H), 3.18 (d, J=14 Hz, 2H), 3.48 (d, J=13 Hz, 1H), 5.14 (d, J=19 Hz, 1H), 5.24 (d, J=19 Hz, 1H), 5.34 (d, J=15 Hz, 1H), 5.71 (d, J=15 Hz, 1H), 7.53 (s, 1H), 7.57–7.63 (m, 1H), 7.70–7.77 (m, 1H), 7.94 (d, J=8 Hz, 1H), 8.10 (d, J=8 Hz, 1H) ; HRMS (EI) m/z calcd for C$_{26}$H$_{30}$N$_2$O$_4$Si (M$^+$) 462.1975, found 462.1976 LRMS (EI) m/z 462 (M$^+$), 447, 415, 402, 391, 377, 363, 348, 317, 289, 243, 231, 73, 59.

(+/−) 5-Ethyl-1,4,5,13-tetrahydro-5-hydroxy-10-(tert-butyloxycarbonylamino)-12-(2-trimethylsilylethyl)-3H,15H-oxepino[3',4':6,7]indolizino[1,2-b]quinoline-3,15-dione (1j) (10-tert-butyloxycarbonylamino-7-(2-trimethylsilylethyl)homocamptothecin)

Following the procedure described above, iodopyridone (10c) (16 mg, 0.033 mmol) was reacted with para-Bocaminophenylisonitrile (21.6 mg, 0.1 mmol) and hexamethylditin (16.7 mg, 0.051 mmol) in benzene (0.5 mL). Chromatography (CH$_2$Cl$_2$:Acetone 7:1) gave compound (1j) 10.7 mg (56%) as a brown solid: $^1$H NMR (300 MHz, CDCl$_3$) δ 0.20 (s, 9H), 0.83–0.93 (m, 2H), 0.99 (t, J=7 Hz, 3H), 1.60 (s, 9H), 1.93–2.10 (m, 2H), 2.90–3.05 (m, 2H), 3.24 (d, J=14 Hz, 1H), 3.44 (d, J=14 Hz, 1H), 3.74 (br s, 1H), 5.03 (d, J=19 Hz, 1H), 5.20 (d, J=19 Hz, 1H), 5.33 (d, J=15 Hz, 1H), 5.67 (d, J=15 Hz, 1H), 6.85 (s, 1H), 7.35–7.44 (m, 2H), 7.85 (d, J=9 Hz, 1H), 8.11 (br s, 1 H) ; HRMS (EI) m/z calcd for C$_{31}$H$_{39}$N$_3$O$_6$Si (M$^+$) 577.2608, found 577.2611 LRMS (EI) m/z 577 (M$^+$), 521, 477, 462, 434, 417, 378, 304, 260, 178, 108, 73.

(+/−) 5-Ethyl-1,4,5,13-tetrahydro-5-hydroxy-10-acetoxy-12-(2-trimethylsilylethyl)-3H, 15H-oxepino[3',4':6,7]indolizino[1,2-b]quinoline-3,15-dione (1k) (10-acetoxy-7-(2-trimethylsilylethyl)homocamptothecin)

Following the procedure described above, iodopyridone (10c) (16 mg, 0.033 mmol) was reacted with para-acetoxyphenylisonitrile (16 mg, 0.1 mmol) and hexamethylditin (16.7 mg, 0.051 mmol) in benzene (0.5 mL) Chromatography (CH$_2$Cl$_2$:Acetone 5:1) gave compound (1k) 7.1 mg (41%) as a tan solid: $^1$H NMR (300 MHz, CDCl$_3$) δ 0.19 (s, 9H), 0.82–0.89 (m, 2H), 0.99 (t, J=7 Hz, 3H), 1.95–2.06 (m, 2H), 2.42 (s, 3H), 2.94–2.98 (m, 2H), 3.23 (d, J=14 Hz, 1H), 3.46 (d, J=14 Hz, 1H), 3.59 (br s, 1H), 5.08 (d, J=19 Hz, 1H), 5.24 (d, J=19 Hz, 1H), 5.35 (d, J=15 Hz, 1H), 5.68 (d, J=15 Hz, 1H), 7.41–7.49 (m, 2H), 7.60 (d, J=2 Hz, 1H), 7.96 (d, J=9 Hz, 1H); HRMS (EI) m/z calcd for C$_{28}$H$_{32}$N$_2$O$_6$Si (M$^+$) 520.2030, found 520.2017 LRMS (EI) m/z 520 (M$^+$), 491, 478, 463, 449, 431, 421, 406, 393, 379, 333, 305, 261, 178, 109, 73.

(+/−) 5-Ethyl-1,4,5,13-tetrahydro-5-hydroxy-10-hydroxy-12-(2-trimethylsilylethyl)-3H,15H-oxepino[3',4':6,7]indolizino[1,2-b]quinoline-3,15-dione (1l) (10-hydroxy-7-(2-trimethylsilylethyl)homocamptothecin)

Following the procedure outlined above, compound (1k) (7.1 mg, 0.014 mmol) was reacted with K$_2$CO$_3$ (4 mg, 0.028 mmol) in a MeOH/H$_2$O solution. The residue was chromatographed (CH$_2$Cl$_2$:Acetone 7:1) to give compound (1l) 2.6 mg (39%) as a yellow solid: $^1$H NMR (300 MHz, CDCl$_3$/CD$_3$OD) δ 0.042 (s, 9H), 0.68–0.92 (m, 5H), 1.80–1.95 (m, 2H), 2.83–2.95 (m, 2H), 3.07 (d, J=14 Hz, 1H), 3.28 (d, J=14 Hz, 1H), 5.05 (s, 2H), 5.29 (d, J=15 Hz, 1H), 5.51 (d, J=15 Hz, 1H), 7.22 (d, J=2 Hz, 1H), 7.26–7.34 (m, 1H), 7.40 (s, 1H), 7.89 (d, J=9 Hz, 1H); HRMS (EI) m/z calcd for C$_{26}$H$_{30}$N$_2$O$_5$Si (M$^+$) 478.1924, found 478.1915 LRMS (EI) m/z 478 (M$^+$), 463, 431, 418, 393, 379, 364, 305, 261, 153, 117, 105, 91, 73, 59.

(+/−) 5-Ethyl-1,4,5,13-tetrahydro-5-hydroxy-10-amino-12-(2-trimethylsilylethyl)-3H,15H-oxepino[3',4':6,7]indolizino

[1,2-b]quinoline-3,15-dione (1m) (10-amino-7-(2-trimethylsilylethyl)homocamptothecin)

Trifluoroaceticacid (0.1 mL) was added to a solution containing $CH_2Cl_2$ (0.5 mL) and compound (1i) (10.7 mg, 0.018 mmol) and the contents were stirred at 22° C. After 5 h, the mixture was poured into sat. $NaHCO_3$ (2 mL) and extracted with EtOAc (6×2 mL). The EtOAc was dried ($Na_2SO_4$), concentrated and chromatographed ($CH_2Cl_2$:MeOH 96:4) to give (1m) 6.7 mg (78%) as a yellow solid: $^1$H NMR (300 MHz, $CDCl_3$/$CD_3OD$) δ 0.059 (s, 9H), 0.70–0.92 (m, 5H), 1.82–1.98 (m, 2H), 2.80–2.92 (m, 2H), 3.08 (d, J=14 Hz, 1H), 3.29 (d, J=14 Hz, 1H), 5.00 (s, 2H), 5.29 (d, J=15 Hz, 1H), 5.52 (d, J=15 Hz, 1H), 6.95 (d, J=2 Hz, 1H), 7.18 (dd, $J_1$=9 Hz, $J_2$=2 Hz, 1H), 7.38 (s, 1H), 7.83 (d, J=9 Hz, 1H).

Although the present invention has been described in detail in connection with the above examples, it is to be understood that such detail is solely for that purpose and that variations can be made by those skilled in the art without departing from the spirit of the invention except as it may be limited by the following claims.

What we claim is:

1. A compound having the formula

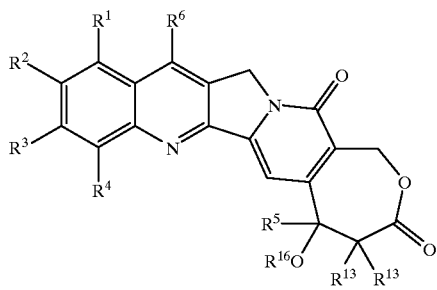

(1)

in racemic form, enantiomerically enriched form or enantiomerically pure form;
wherein $R^1$ and $R^2$ are independently the same or different and are hydrogen, —C(O)$R^f$ wherein $R^f$ is an alkyl group, an alkoxy group, an amino group or a hydroxy group, an alkyl group, an alkenyl group, an alkynyl group, an alkoxy group, an aryloxy group, an acyloxy group, —OC(O)O$R^d$, wherein $R^d$ is an alkyl group, —OC(O)N$R^aR^b$ wherein $R^a$ and $R^b$ are independently the same or different, H, —C(O)$R^f$, an alkyl group or an aryl group, a halogen, a hydroxy group, a nitro group, a cyano group, an azido group, a formyl group, a hydrazino group, an amino group, —$SR^c$, wherein $R^d$ is hydrogen, —C(O)$R^f$, an alkyl group or an aryl group; or $R^1$ and $R^2$ together form a chain of three or four members selected from the group of CH, $CH_2$, O, S, NH, or $NR^{15}$, wherein $R^{15}$ is an $C_1$–$C_6$ alkyl group;

$R^3$ is H, a halogen atom, a nitro group, an amino group, a hydroxy group, or a cyano group; or $R^2$ and $R^3$ together form a chain of three or four members selected from the group of CH, $CH_2$, O, S, NH, or $NR^{15}$;

$R^4$ is H, F, an amino group, a $C_{1-3}$ alkyl group, a $C_{2-3}$ alkenyl group, a $C_{2-3}$ alkynyl group, a trialkylsilyl group or a $C_{1-3}$ alkoxy group;

$R^5$ is a $C_{1-10}$ alkyl group, an alkenyl group, an alkynyl group, or a benzyl group;

$R^6$ is —Si($R^8R^9R^{10}$) or —($R^7$)Si($R^8R^9R^{10}$), wherein $R^7$ is an alkylene group, an alkenylene group, or an alkynylene group; and $R^8$, $R^9$ and $R^{10}$ are independently a $C_{1-10}$ alkyl group, a $C_{2-10}$ alkenyl group, a $C_{2-10}$ alkynyl group, an aryl group or a —($CH_2$)$_N R^{11}$ group, wherein N is an integer within the range of 1 through 10 and $R^{11}$ is a hydroxy group, an alkoxy group, an amino group, an alkylamino group, a dialkylamino group, a halogen atom, a cyano group, —$SR^c$ or a nitro group;

$R^{13}$ is H, F or —$CH_3$;

$R^{16}$ is —C(O)$R^f$ or H; and
pharmaceutically acceptable salts thereof.

2. The compound of claim 1 wherein $R^{16}$ is H.

3. The compound of claim 2 wherein $R^2$ and $R^3$ together form a group of the formula —O($CH_2$)$_n$O— wherein n represents the integer 1 or 2.

4. The compound of claim 2 wherein $R^5$ is an ethyl group, an allyl group, a benzyl group or a propargyl group.

5. The compound of claim 2 wherein $R^{13}$ is H.

6. The compound of claim 5 wherein $R^5$ is an ethyl group.

7. The compound of claim 6 wherein $R^4$ is H.

8. The compound of claim 7 wherein $R^8$ and $R^9$ are methyl groups, $R^{10}$ is a tert-butyl group or a methyl group, $R^1$ is H and $R^3$ is H.

9. The compound of claim 8 wherein $R^2$ is H, $NH_2$ or OH.

* * * * *